United States Patent [19]
Eastvold et al.

[11] Patent Number: 5,745,268
[45] Date of Patent: Apr. 28, 1998

[54] VASCULAR PORTABLE ASSISTANT COMPUTER SYSTEM

[75] Inventors: Roger Eastvold, Newport Beach; Tim Peeler, Mission Viego; Dimitrios Loumakis, Lake Forrest; Milutin Nikolic, Santa Marguarita; Jyoti Lachhwani, San Clemente; Dan Durick, Newport Beach; Hatem El-Sebaaly, Lake Forest; Lech Molga, Laguna Niguel, all of Calif.

[73] Assignee: Toshiba America Medical Systems, Inc., Tustin, Calif.

[21] Appl. No.: 477,297

[22] Filed: Jun. 7, 1995

[51] Int. Cl.$^6$ .................................................. H04B 10/08
[52] U.S. Cl. .................... 359/110; 379/241; 379/247; 395/183.02
[58] Field of Search ................... 357/110, 125, 357/118, 164, 167; 370/13, 16.1, 14, 247, 241, 248, 251, 242; 364/483, 491; 371/20.1; 395/183.01, 183.02, 183.04, 183.03, 183.06

[56] References Cited

U.S. PATENT DOCUMENTS

| 4,937,825 | 6/1990 | Ballard et al. | 371/70.1 |
|---|---|---|---|
| 5,301,050 | 4/1994 | Czerwiec et al. | 359/125 |
| 5,325,223 | 6/1994 | Bears | 359/125 |
| 5,375,159 | 12/1994 | Williams | 370/13 |
| 5,381,403 | 1/1995 | Maher et al. | 370/13 |
| 5,416,623 | 5/1995 | Dawson et al. | 359/110 |
| 5,442,472 | 8/1995 | Skrobko | 359/110 |
| 5,459,777 | 10/1995 | Bassa et al. | 370/13 |
| 5,471,459 | 11/1995 | Gut | 370/13 |

OTHER PUBLICATIONS

D. Lyons, "Hyperlinking Service Manuals," Tech Wra, VARBusiness, Aug. 1994, pp. 206 and 180.
D.J. Long, "Advanced Technologies Pave the Road to Service and Support Excellence in the 90s," AFSM Intnernational, Apr. 1994, pp. 16–18.
C. Curran, "Diagnostics and the Future of Field Service Engineers," Medical Imaging, Mar. 1994, pp. 44–51.
S. Wallace, "Experts in the Field," Byte, Oct. 1994, pp. 86–96.
M. Ben–Bassat, Ph.D. et al., "Different Approaches to Fault Isolation Support Software," Part II: Analysis, AFSM International, Mar. 1995, pp. 11–21.
K.K. Teague, "A Remote Advantage," Second Source Imaging, Apr. 1992, four pages.
Article: R. Eastvold, "Accelerated Testing and Automated Result Interpretation for Imaging Systems," 1989, 14 pages.

*Primary Examiner*—Wellington Chin
*Assistant Examiner*—Rafael Bacares
*Attorney, Agent, or Firm*—Ronald L. Yin; Limbach & Limbach LLP

[57] ABSTRACT

The present invention comprises an apparatus for communicating, monitoring, and gathering data from and with a plurality of electrical devices connected to predetermined points on a network of equipment. The present invention is particularly suitable for x-ray and vascular systems which have multiple pieces of equipment which require maintenance, repair, and adjustment. The apparatus of the present invention provides for faster repair and maintenance of vascular or x-ray systems through the use of an expert system which provides diagnostic and troubleshooting assistance to the field service engineer.

22 Claims, 52 Drawing Sheets

Microfiche Appendix Included
(1 Microfiche, 28 Pages)

| Programmable In/Out | FPGA I/O | 1A | 1B | FPGA I/O | Programmable In/Out |
|---|---|---|---|---|---|
| Programmable In/Out | FPGA I/O | 2A | 2B | FPGA I/O | Programmable In/Out |
| Programmable In/Out | FPGA I/O | 3A | 3B | FPGA I/O | Programmable In/Out |
| Programmable In/Out | FPGA I/O | 4A | 4B | FPGA I/O | Programmable In/Out |
| Programmable In/Out | FPGA I/O | 5A | 5B | FPGA I/O | Programmable In/Out |
| Programmable In/Out | FPGA I/O | 6A | 6B | FPGA I/O | Programmable In/Out |
| Programmable In/Out | FPGA I/O | 7A | 7B | FPGA I/O | Programmable In/Out |
| Programmable In/Out | FPGA I/O | 8A | 8B | FPGA I/O | Programmable In/Out |
| Programmable In/Out | FPGA I/O | 9A | 9B | FPGA I/O | Programmable In/Out |
| Programmable In/Out | FPGA I/O | 10A | 10B | FPGA I/O | Programmable In/Out |
| Programmable In/Out | FPGA I/O | 11A | 11B | FPGA I/O | Programmable In/Out |
| Programmable In/Out | FPGA I/O | 12A | 12B | GND | Ground |
| Programmable In/Out | FPGA I/O | 13A | 13B | FPGA I/O | Programmable In/Out |
| Programmable In/Out | FPGA I/O | 14A | 14B | FPGA I/O | Programmable In/Out |
| Programmable In/Out | FPGA I/O | 15A | 15B | FPGA I/O | Programmable In/Out |
| Programmable In/Out | FPGA I/O | 16A | 16B | FPGA I/O | Programmable In/Out |
| Port A bit 2 from uP | PA2 | 17A | 17B | FPGA I/O | Programmable In/Out |
| Port A bit 3 from uP | PA3 | 18A | 18B | FPGA I/O | Programmable In/Out |
| Analog Input 3 (+12V) | AIN3 | 19A | 19B | FPGA I/O | Programmable In/Out |
| Analog Input 2 (Battery 2) | AIN2 | 20A | 20B | FPGA I/O | Programmable In/Out |
| Analog Input 1 (Battery 1) | AIN1 | 21A | 21B | FPGA I/O | Programmable In/Out |
| Analog Input 0 (+5V) | AIN0 | 22A | 22B | FPGA I/O | Programmable In/Out |
| Power +5V | VCC | 23A | 23B | VCC | Power +5V |
| Power +5V | VCC | 24A | 24B | VCC | Power +5V |
| Ground | GND | 25A | 25B | GND | Ground |
| Ground | GND | 26A | 26B | GND | Ground |
| Wake up from RTC | WAKEup-_- | 27A | 27B | FPGA I/O | Programmable In/Out |
| Programmable In/Out | FPGA I/O | 28A | 28B | RESET_BUTTON | RESET from uP |
| Programmable In/Out | FPGA I/O | 29A | 29B | AIN7 | Analog Input 7 (+kVmA) |
| Programmable In/Out | FPGA I/O | 30A | 30B | AIN6 | Analog Input 6 (-kVmA) |
| Programmable In/Out | FPGA I/O | 31A | 31B | AIN5 | Analog Input 5 (NC) |
| Programmable In/Out | FPGA I/O | 32A | 32B | AIN4 | Analog Input 4 (NC) |
| Programmable In/Out | FPGA I/O | 33A | 33B | M2 | M2 from FPGA |
| Programmable In/Out | FPGA I/O | 34A | 34B | HDC | HDC from FPGA |
| Programmable In/Out | FPGA I/O | 35A | 35B | LDC- | LDC from FPGA |
| Power Fail/XIRQ from uP | PWR_FAIL | 36A | 36B | +9V | +9V from PM |
| Spare Connection | SPARE | 37A | 37B | +9V | +9V from PM |
| Spare Connection | SPARE | 38A | 38B | SPARE | Spare Connection |
| Spare Connection | SPARE | 39A | 39B | SPARE | Spare Connection |
| Spare Connection | SPARE | 40A | 40B | SPARE | Spare Connection |
| Programmable In/Out | FPGA I/O | 1A | 1B | FPGA I/O | Programmable In/Out |
| Programmable In/Out | FPGA I/O | 2A | 2B | FPGA I/O | Programmable In/Out |
| Programmable In/Out | FPGA I/O | 3A | 3B | FPGA I/O | Programmable In/Out |
| Programmable In/Out | FPGA I/O | 4A | 4B | FPGA I/O | Programmable In/Out |
| Programmable In/Out | FPGA I/O | 5A | 5B | FPGA I/O | Programmable In/Out |

MASTER MULTI PIN CONNECTOR ASSIGNMENTS

FIGURE 9

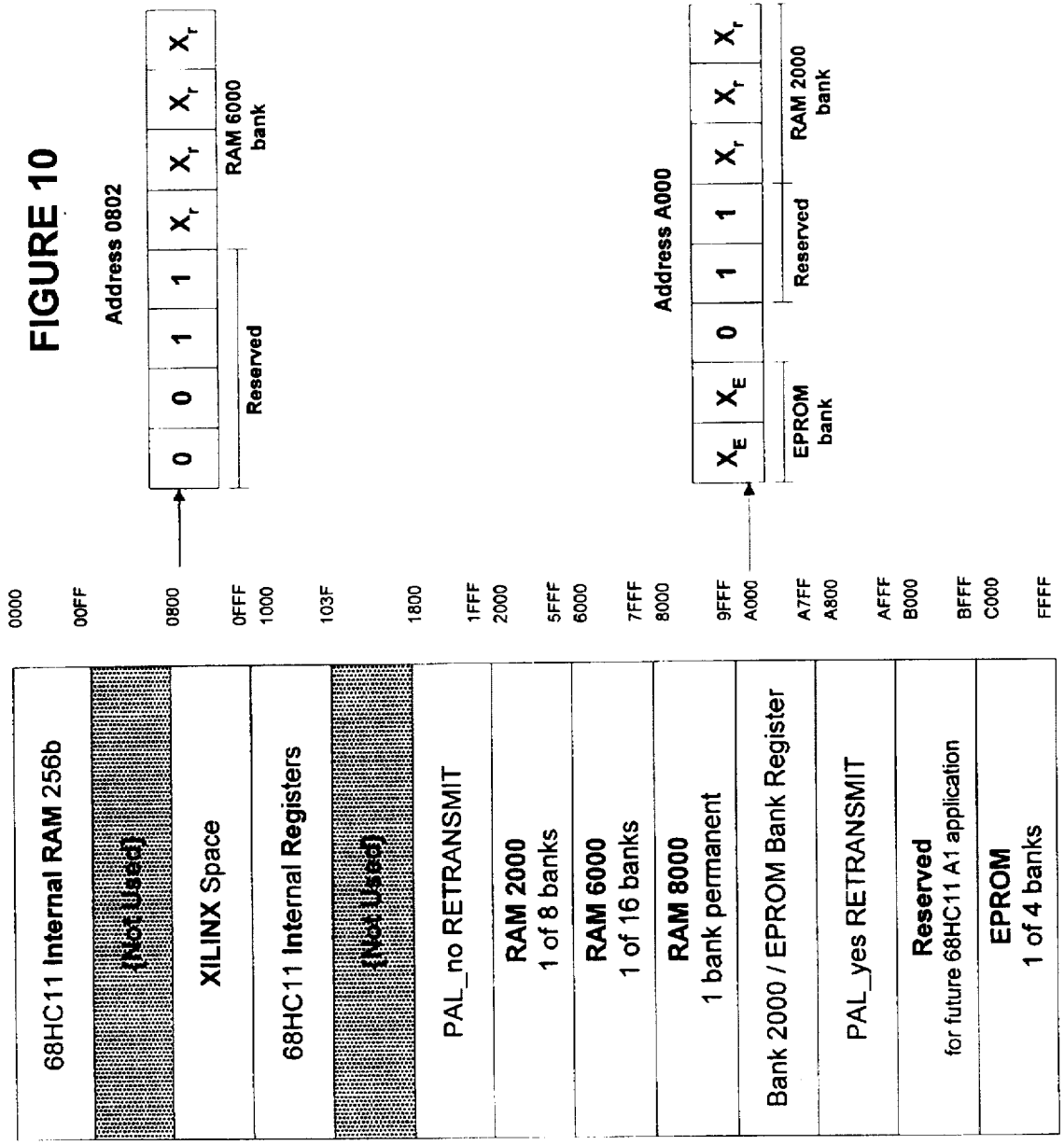

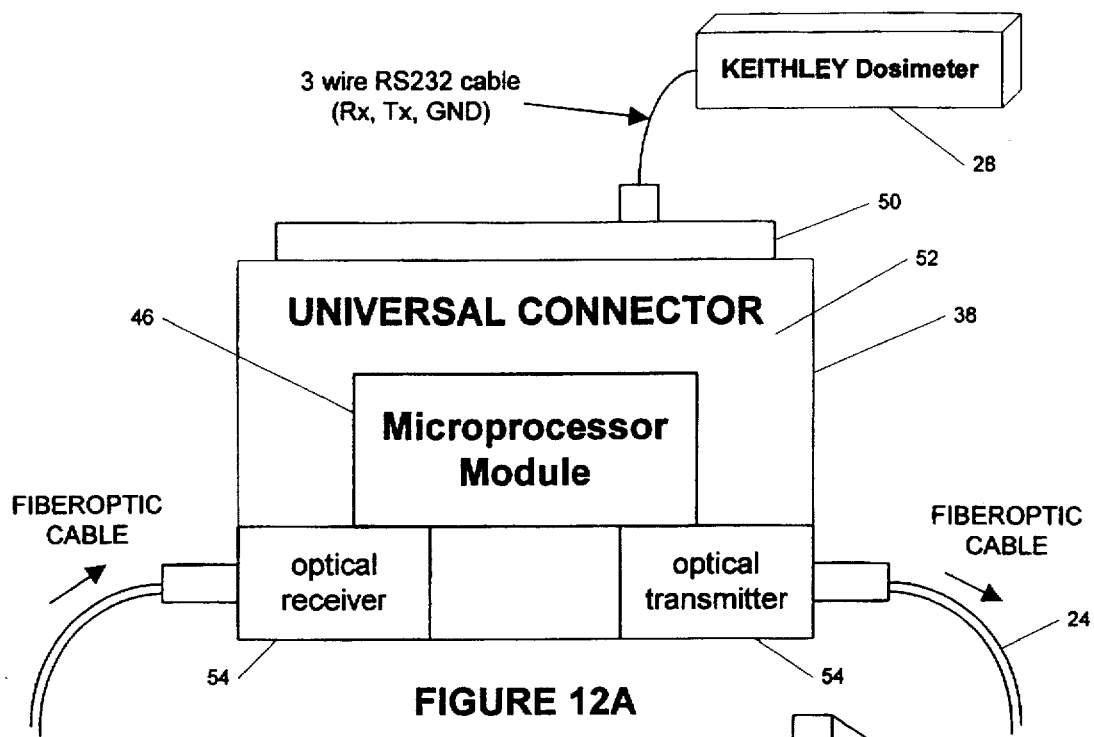
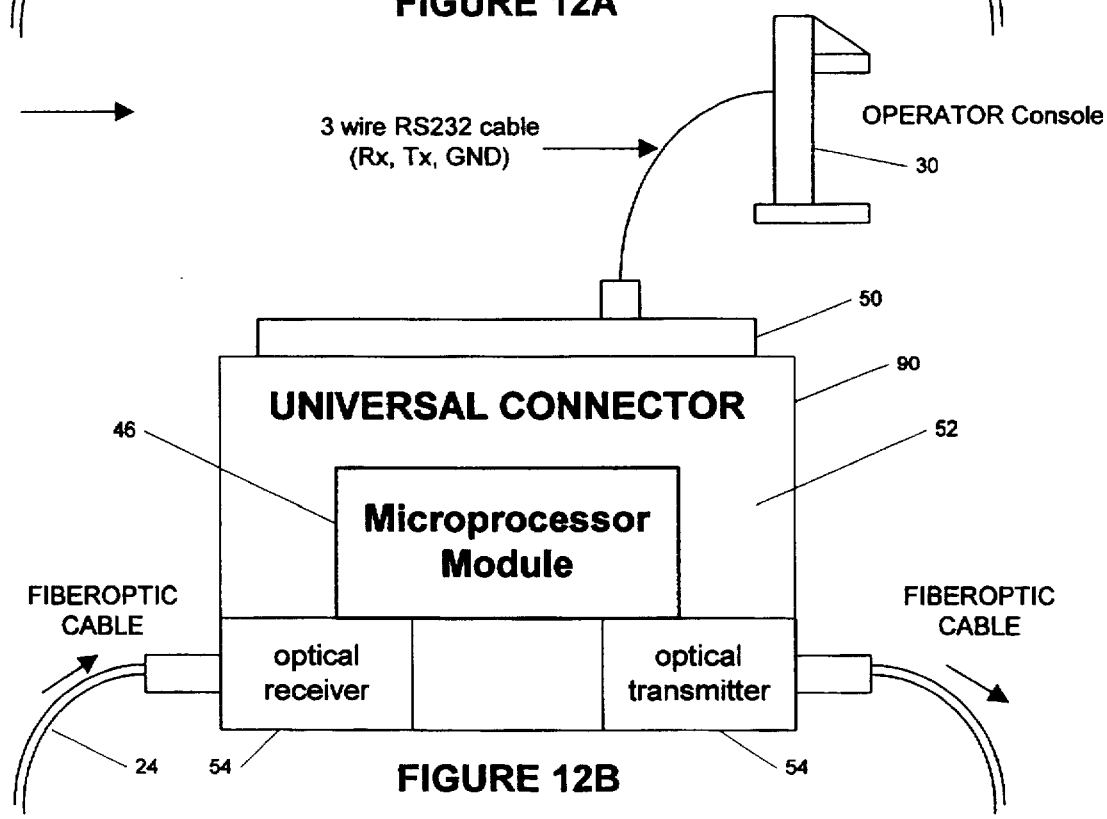

FIGURE 15A

```
    if  (iTop < lMinzeroConAC)
        iMinZeroConAC = iTop;

if  (iBottom > iMaxZeroConAC)
            iMaxZeroConAc = iBottom;

if  (iLeft < iMinZeroConTransverse)
            iMinZeroConTransverse = iLeft;

if  (iRight > iMaxZeroConTransverse)
            iMaxZeroConTransverse = iRight;

Iterator++;
}
// Following is in pixels
int iZeroSeperationAC = iMaxZeroConAc - iMinZeroConAC;
int iZeroSeperationTransverse = iMaxZeroConTransverse -
iMinZeroConTransverse;

if  (dPixPerMM == 0.0) // cannot allow divisno by zero.
    return FALSE;
// Following is in Millimeters
double dMeasuredDiameter = (double)pOuterStar->AvgDiameter() /
            dPixPerMM;   // dPixPerMN is in INI file double dZeroContrastAC = (double)iZeroSeperationAC / dPixPerMM;

double dZeroContrastTransverse = (double)iZeroSeperationTransverse
/
            dPixPerMM;

char units () = * Millimeters*;
LogEntry(PAppName, FuncName, PLogEntryType[ELog], ELog,
    "ACZeroConstrastDistance = %4.1f %s", dZeroContrastAC, units);

LogEntry(PAppName, FuncName, PLogEntryType[ELog], ELog,
    "TransverseZeroContrastDistance = %4.1f %s",
dZeroContrasTransverse,  units);

double dMagnification = dMeasuredDiameter / dActualDiameter;
LogEntry (PAppName, FuncName, PLogEntryType [ELog], ELog,
    "Magnification = %4.2f*, dMagnification);

dFocalSpotAC = (dAngle/57.3) *
    dZeroContrastAC/(dMagnification - 1.0);
LogEntry (PAppName, FuncName, PLogEntryType [ELog], ELog,
    "ACFocalSpot = %d.1f %s", dFocalSpotAC, units);

dFocalSpotTransverse = (dAngle/57.3) *
    dZeroContrastTransverse/ (dMagnification - 1.0);
LogEntry \(PAppName, FuncName,PLogEntryType [ELog], ELog,
    "TransverseFocalSpot = %d.1f %s", dFocalSpotTransverse, units);
return TRUE;
```

FIGURE 15B

```
        return FALSE;
    if (!AverageFrames())
        return FALSE;
    if (!FindBackground())
        return FALSE;
    if (!FindStar())
        return FALSE;
    if (!FindInner())
        return FALSE;
    if (!pImgPrc->ReLoad())
        return FALSE;
    if (!pImgPrc->FindQuadrants(pQuadrants)
        return FALSE;
    if (!pImgPrc->ReLoad())
        return FALSE;
    if (!pImgPrc->FindZerosInQuadrants(pQuadrants,pZeroContrastSet))
        return FALSE;
    if (!FindFocalSpot())
        return FALSE;

BOOL
StarPhan:=findFocalSpot ()
(
    char FuncName [] = "StarPhan::FindFocalSpot':
    LogEntry(PAppName, FuncName, PLogEntryType[EDebug], EDebug,
        LogMsg([EntryToFunction]);

TISArrayAsVectorIterator<ImgObj> Iterator(*pZeroContrastSet);
    Iterator.Restart();
    int iMinZeroConAC = MAXINT;
    int iMaxZeroConAC = MAXINT * -1;
    int iMinZeroConTransverse = MAXINT;
    int iMinZeroConTransverse = MAXINT * -1;
    while (Iterator) {
        ImgObj *pImgObj = Iterator.Current();

int iTop = pImgObj->TopBound();
        int iBottom = pImgObj->BottomBound();

int iLeft = pImgObj->LeftBound();
        int iRight = pImgObj->RightBound();
```

Half Value Test

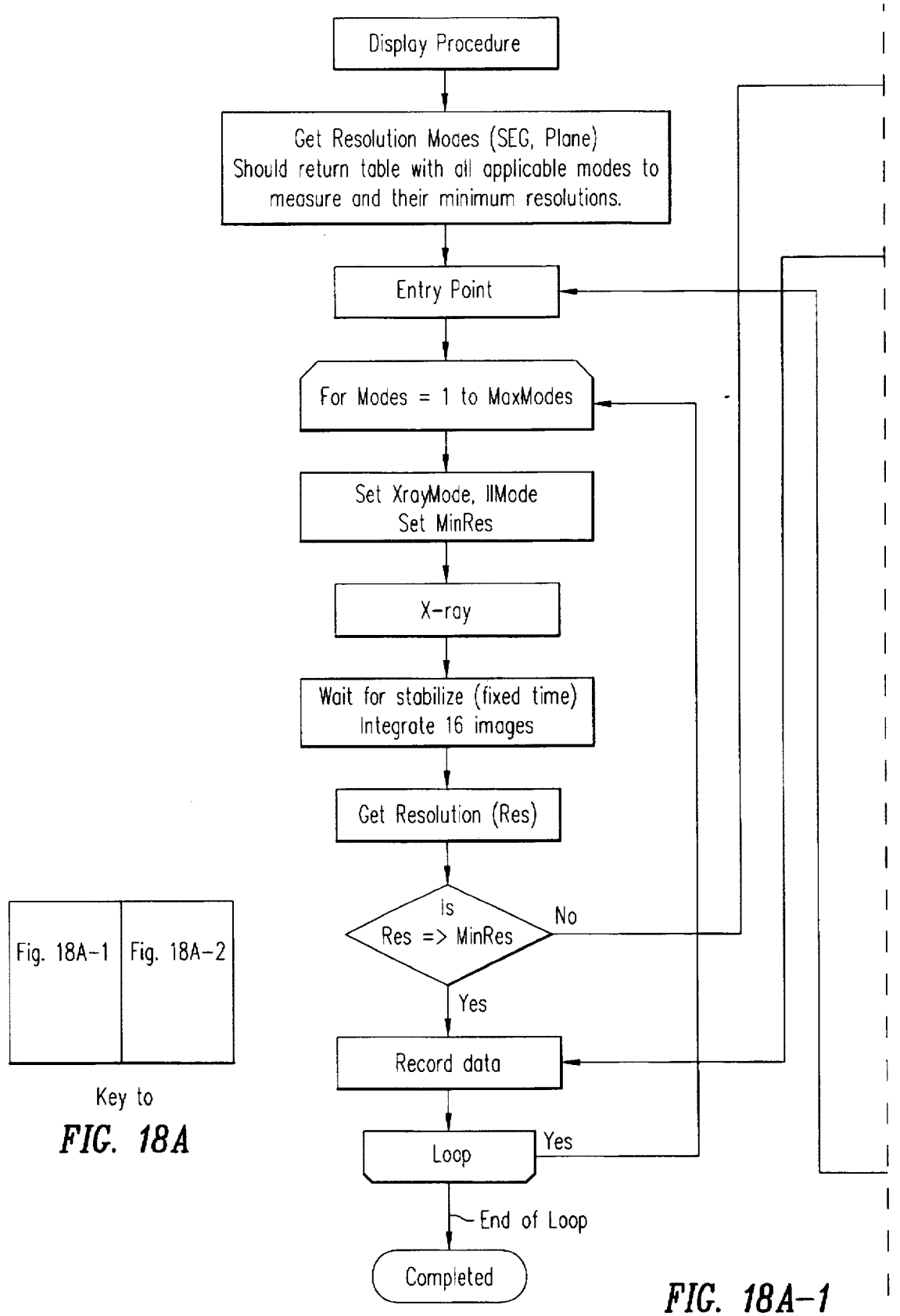

Quick Tube Calibration Check

Check Max ERR (Entrance Exposure Rate)

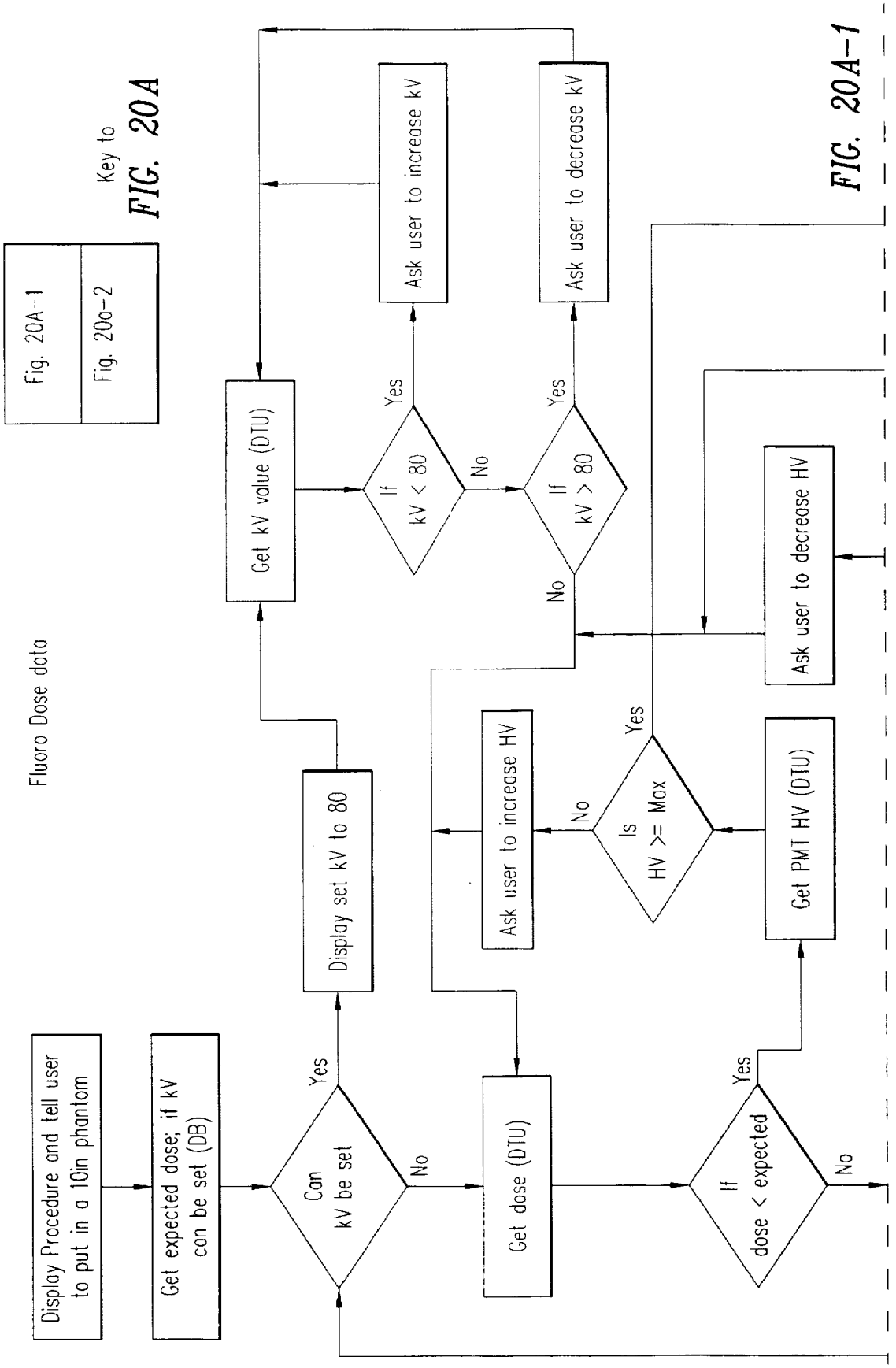

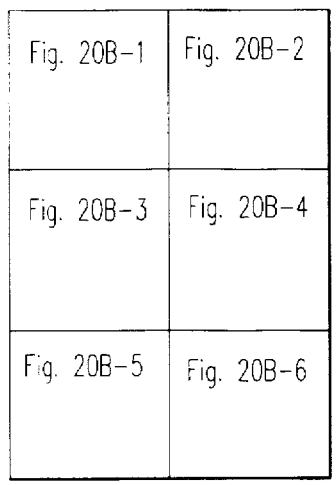
Key to
*FIG. 20B*
*FIG. 20B-1*
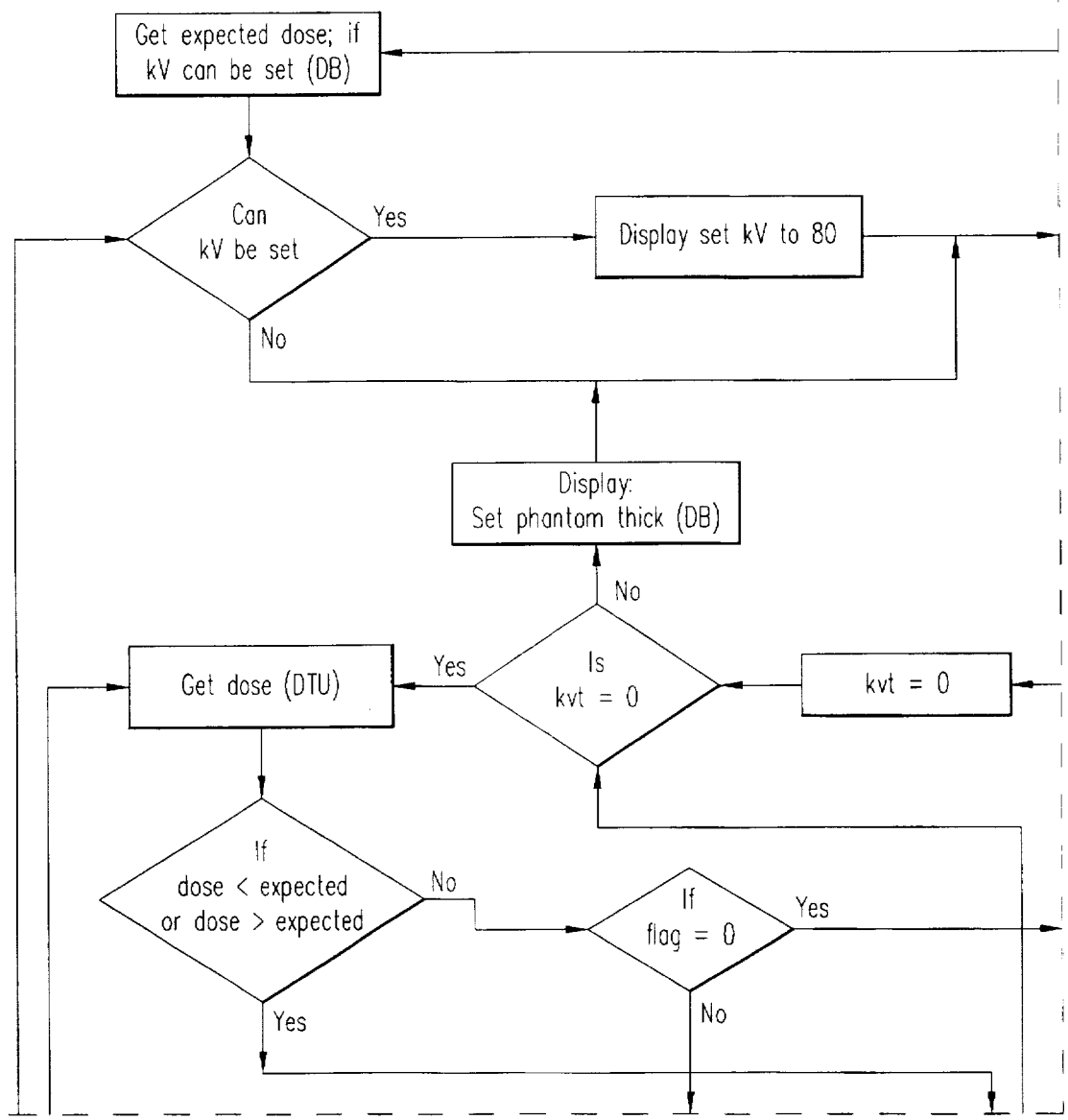

RECEIPT OF EACH PACKET ACKNOWLEDGED
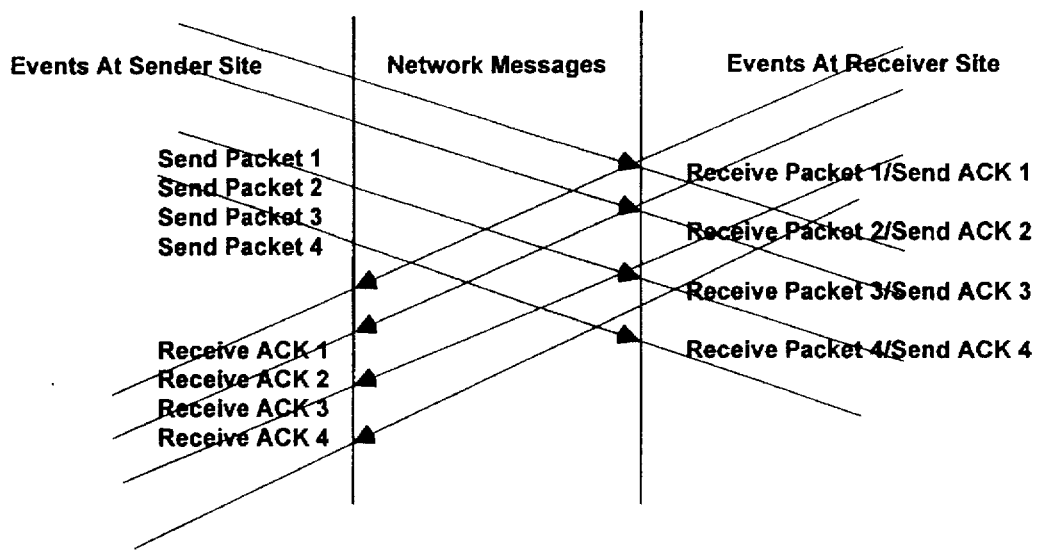
A protocol using sliding window.
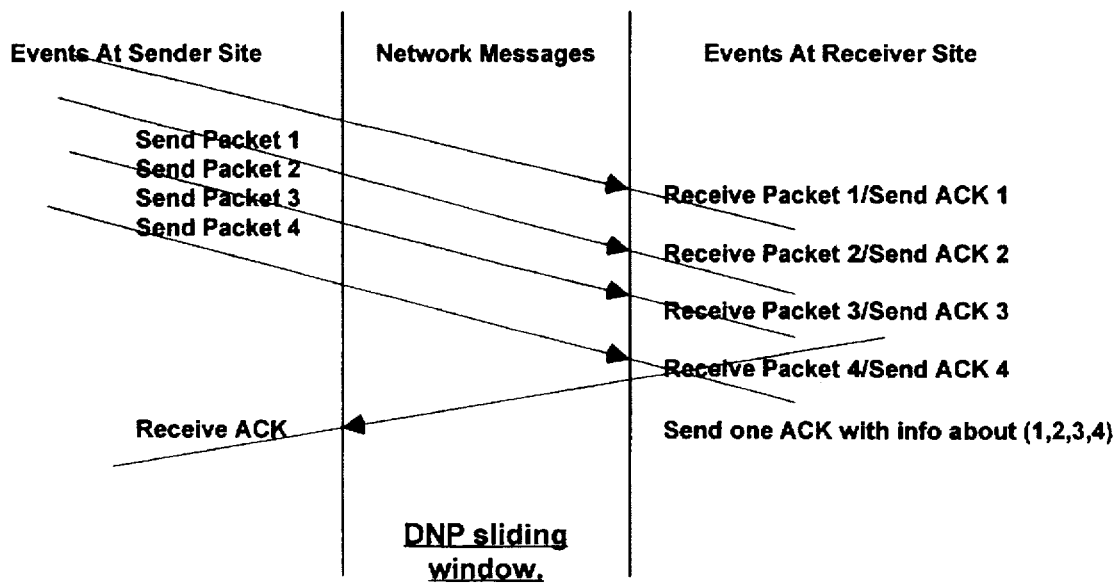
DNP sliding window.
FIGURE 25A

START-UP PSEUDOCODE

- Disable all interrupts
- Select the first bank in the EPROM chip.
- Initialize the FPGA
- Download the FPGA program from EPROM to the mapped address of the XILINX
- Perform diagnostics:
  - Test RAM2000
  - Test RAM6000
- Failures are reported via the LED.
- Initialize the SCI (Serial Communication Interface)
  - Select the first bank of the RAM2000 and RAM6000.
  - Set up the Timer output capture to interrupt every 10 milliseconds. (Start Clock)
  - Allocate and initialize the network receive and send buffers.
  - Initialize the SCI interface. Verify that the interface is attached to the optics and not the SCM.
- Enable interrupts.
- Enable the transmitter on the SCI and enable the receiver interrupt.

- \* Wait for Packets ForEver (continuous loop) If Packet is received, process the packet.
   Loop Again\*

FIGURE 26

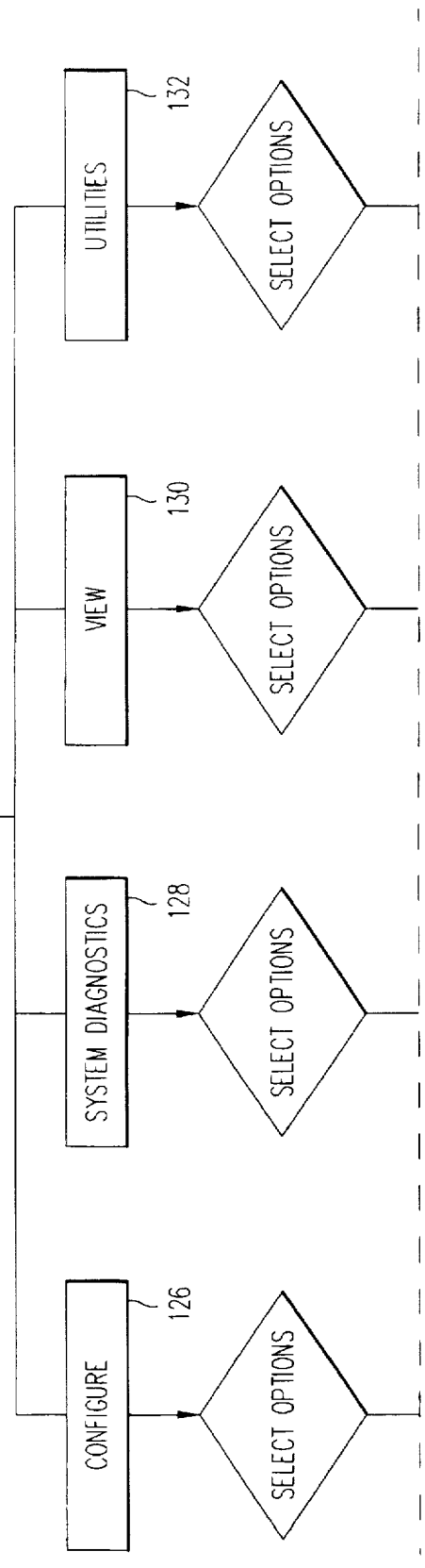

TROUBLESHOOT PROCESS

VASCULAR PORTABLE ASSISTANT COMPUTER SYSTEM

MICROFICHE APPENDIX

This application is submitted with a microfiche appendix consisting of one (1) microfiche with twenty-eight (28) frames.

TECHNICAL FIELD

The invention described herein relates to the monitoring, maintenance, and repair of vascular x-ray imaging systems or any similar system in which a number of distinct equipment modules are interconnected to form a functioning system.

BACKGROUND OF THE INVENTION

A typical vascular system consists of a patient table, an operator console, a control panel, and a high tension transformer. These components are costly to service. The increased costs are a direct result of the trend toward modular systems. A modular design allows the buyer to customize a system to meet his individual requirements, but at an increased cost since repair and maintenance is more complex and must also be tailored to the individual system. The cost factor alone makes vascular systems primary candidates for development of cost saving diagnostic techniques and systems.

Repair and maintenance requires that the field service engineer must have the technical manuals and repair procedures immediately available to him or her at the site to research any eventuality that may occur. Again, however, modularity becomes a factor. Since a variety of modules may be used in a typical vascular system, technical manuals and procedures for each module must be on-hand. This can represent a substantial amount of paper.

Diagnosing system problems can also be a hit or miss proposition. To diagnose a problem the field service engineer has to run a procedure and often needs to refer to a technical manual to do so. Quite frequently, the first procedure which is run does not solve the problem; therefore, additional procedures need to be performed. This becomes extremely time consuming and costly. In some cases, a procedure may indicate that a part needs to be replaced, but once the part is replaced, the system still does not operate properly.

More than one procedure may be required to identify the problem. Once the cause of the problem has been determined, more procedures must be run to determine how to fix or replace the faulty component. While more experienced field service engineers may be able to more easily identify the problem and know what steps to take to resolve it, some problems occur rarely enough that even experienced field service engineers may misdiagnose the cause.

A second cost factor is "Optimum" performance. "Optimum" performance is often in the eye of the beholder. Each doctor who uses the images produced by the system has specific performance parameters which are "Optimum" to that individual. It is important to be able to easily recreate "Optimum" performance and return the system to the settings that provide the performance characteristics that individual users prefer.

On-line monitoring of system performance is also a desirable objective. This objective is often complicated in vascular systems because the various system components are generally located in different rooms and may be powered by different power supplies. Problems of electrical safety, grounding and distance are typically presented.

SUMMARY OF THE INVENTION

The present invention is an apparatus for communicating with a plurality of devices comprising a plurality of distributed test units ("DTUs") each communicating with an associated one of the plurality of devices, a master DTU, a network which permits communication of information among the master DTU and plurality of DTUs, and a system monitor unit communicating with the plurality of DTUs by way of the master DTU. The system monitor unit includes a control unit which gathers information from the plurality of DTUs, a data base compiled from the information gathered from the plurality of DTUs, and a diagnostic unit which analyzes the gathered information and identifies conditions in one or more of the plurality of devices which may require servicing.

Using the network of DTUs, connected to selected vascular devices, such as the dosimeter and control console, the DTUs gather and transfer data to the system monitor. The field service engineer connects a field service notebook (laptop computer) to the system monitor to access data gathered from the DTUs. Using the gathered data, accurate measures of system performance are developed which can easily be monitored and recreated, yielding "optimum" performance levels based on preset benchmarks. Through the electronic database storage capabilities of the system monitor, the field service engineer is provided with a support system and reference materials, including component lists, manuals, and current software releases, that allow for quicker, less cumbersome and more accurate repair of the vascular system.

The present invention further provides an automated system which reduces the probability of errors occurring during manual data transfer, decreases hard copy support and technical data which the field service engineer has to carry to the site, and, allows the system monitor to perform the highly accurate performance data analysis required, thus reducing human error in diagnosis and repair.

Such a diagnostic system enhances the efficiency of troubleshooting and repair and leads to shorter down times, thereby reducing costs and improving customer satisfaction. The system is also non-invasive so that it can collect data from the test points while the vascular system is in use. This allows field service engineers to proactively detect and correct system performance deterioration before the system fails.

An offsite Technical Assistance Center (TAC) can also contact the system monitor remotely to access the DTU network to check system operations, and to update the information stored in the system monitor.

The present invention also shortens evaluation time through automation. The diagnostic system of the present invention employs an expert system which comprises software in the system monitor processor which analyzes data gathered and stored from the DTUs. The expert system can refer more quickly to similar problem situations in the past and recall resolutions. The expert system is therefore able to provide the field service engineer with suggestions on how and where to work on the system. The expert system also anticipates when an incorrect procedure is run, and directs the field service engineer to alternative correct solutions. As a result, time consuming guesswork, and trial and error, normally associated with the repair process are reduced, thereby allowing faster repair or adjustment of the vascular system.

BRIEF DESCRIPTION OF THE DRAWINGS

FIG. 9 is a table of the master pin assignments for the multi pin connector used in the DTUs.

FIG. 10 is a diagram of the DTU microprocessor memory map consisting of RAM and EPROM memory.

FIG. 12A is a block diagram of a dosimeter DTU.

FIG. 12B is a block diagram of an operator console DTU connected to the operator console.

FIG. 15A and 15B is the problem isolation algorithm used for the resolution procedure.

FIGS. 25A and 25B are diagrams showing the "sliding window" technique of increasing the reliability of data transmission.

FIG. 26 illustrates a start-up pseudo code for the DTUs.

DETAILED DESCRIPTION OF THE INVENTION

Figure 1:
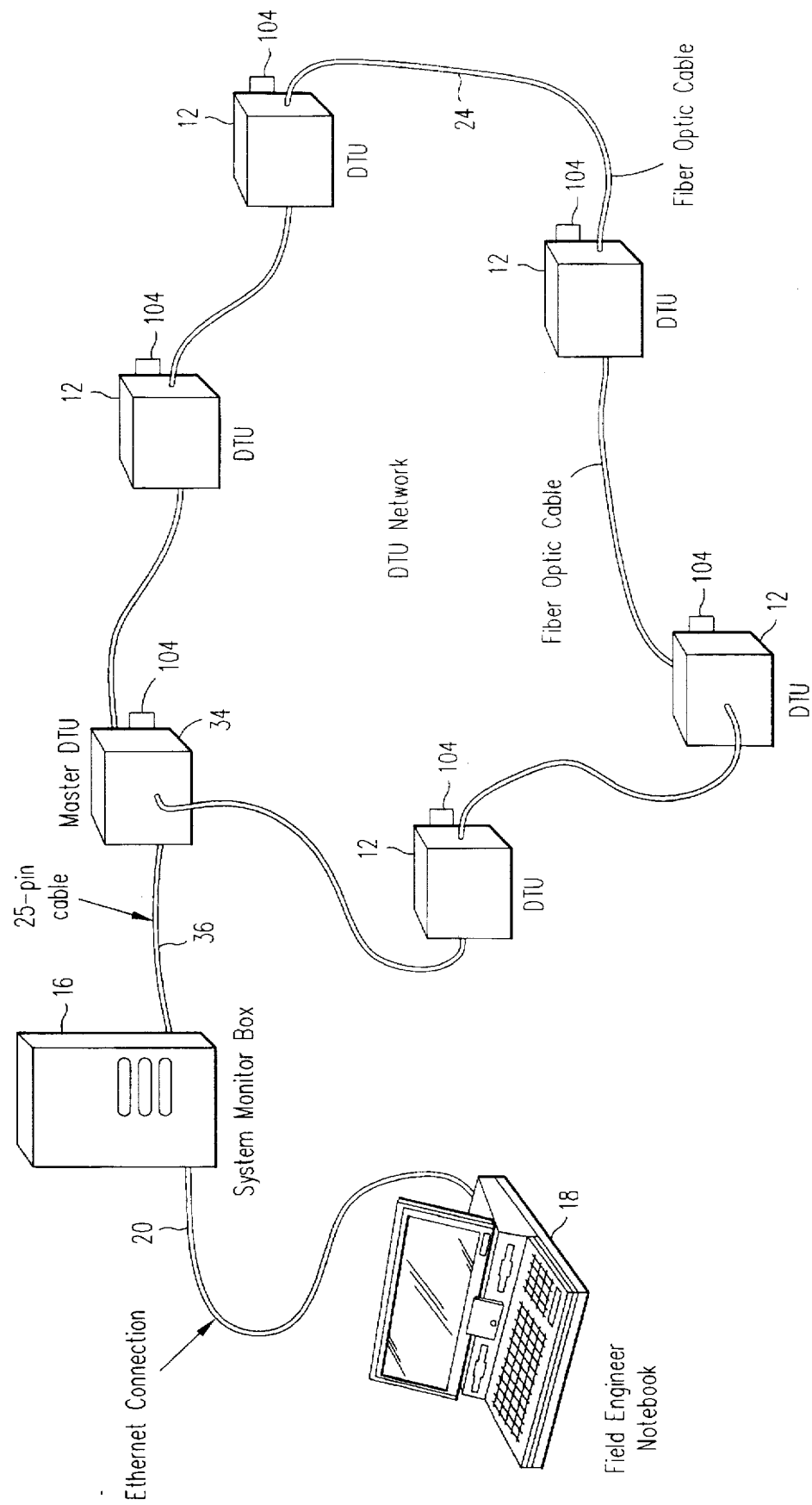
FIG. 1 is a diagram showing an example of the diagnostic system of the present invention.

As shown in FIG. 1, the diagnostic system of the present invention 10 comprises three major components: 1) a hardware network of distributed test units (DTUs) 12 that can be attached to predefined test points on the various modules which make up the vascular system 14; 2) a system monitor 16 that receives and manipulates data from the DTUs 2; and 3) a field service notebook 18 (a conventional laptop computer) that serves as the field service engineer interface with the system monitor 16 and enables the user to access the diagnostic system of the present invention. A Technical Assistance Center (TAC) 19, conceptually shown in FIG. 3, is a further component of the present invention.

System Architecture

Figure 2:
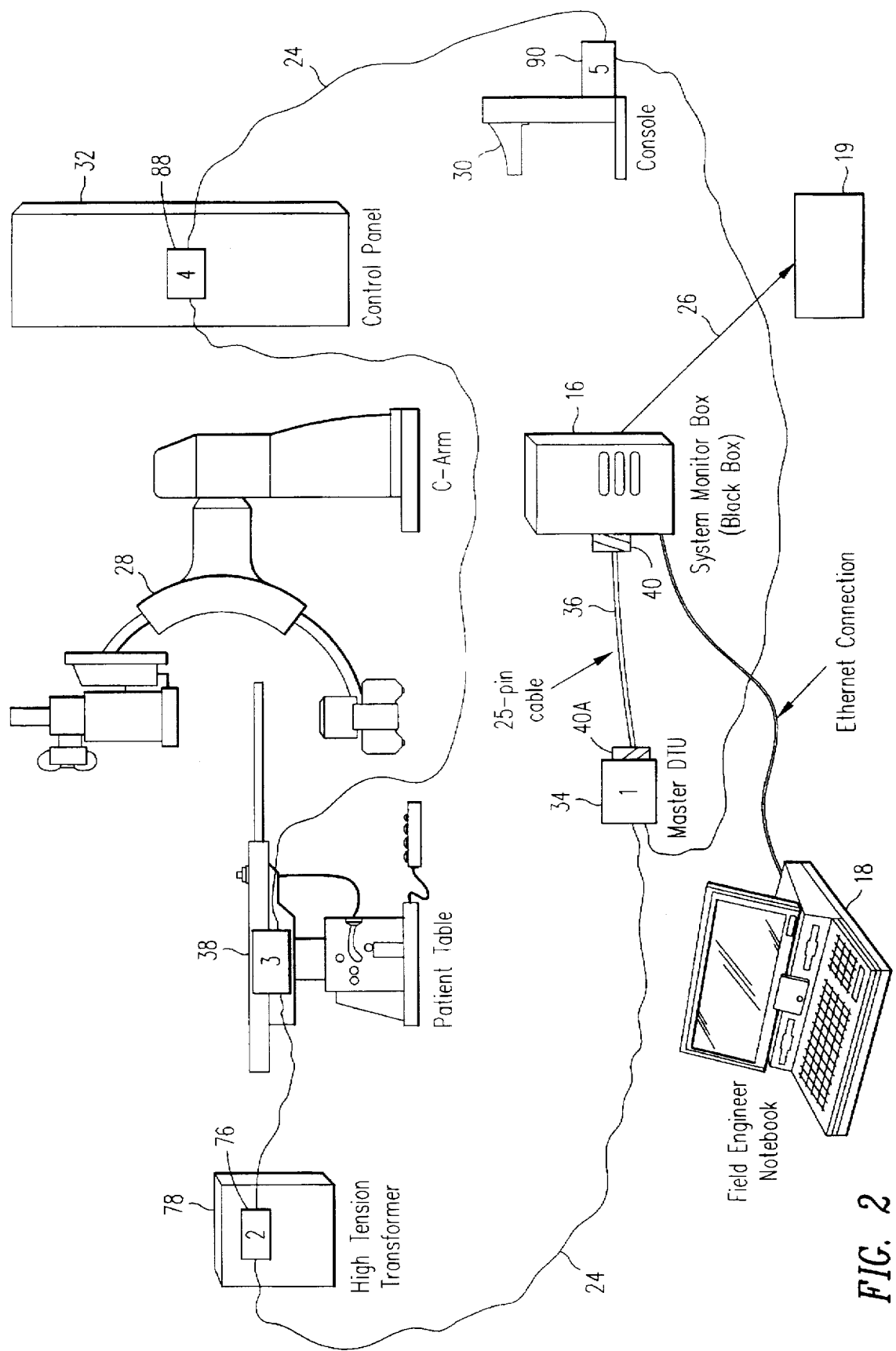
FIG. 2, is a diagram of an example of the diagnostic system of the present invention as connected to a vascular system.

As shown in FIGS. 1 and 2, the preferred embodiment of the diagnostic system of the present invention 10 in its simplest form is a series of DTUs 12 continuously gathering performance data at specified test points on the vascular system 14 and feeding that information back to the system monitor 16. As shown in FIG. 2, a vascular system 14 used for x-ray procedures may include a collection of modular equipment such as a high voltage tension transformer 78, a patient table 17, a control panel 32, and a console 30. The DTU Network 13 and the system monitor 16 are located on-site and are connected to the equipment in the vascular system 14. The DTUs 12 are connected to each other by a fiber optic network 24. In the preferred embodiment, the fiber optic network 24 uses TOTX173/TORX173 and TOCP172 fiber optic cable available from Toshiba America Electronic Components, Inc. located in Irvine, Calif. The maximum length of the fiber optic network 24 between each DTU 12, is ten meters. A field service notebook 18 is brought to the site by the field service engineer and is connected to the system monitor 16 by an ethernet connection 20. A graphical user interface (GUI) 22 is provided on the field service notebook 18 which enables the field service engineer to communicate directly with the DTU Network 13.

Figure 3:
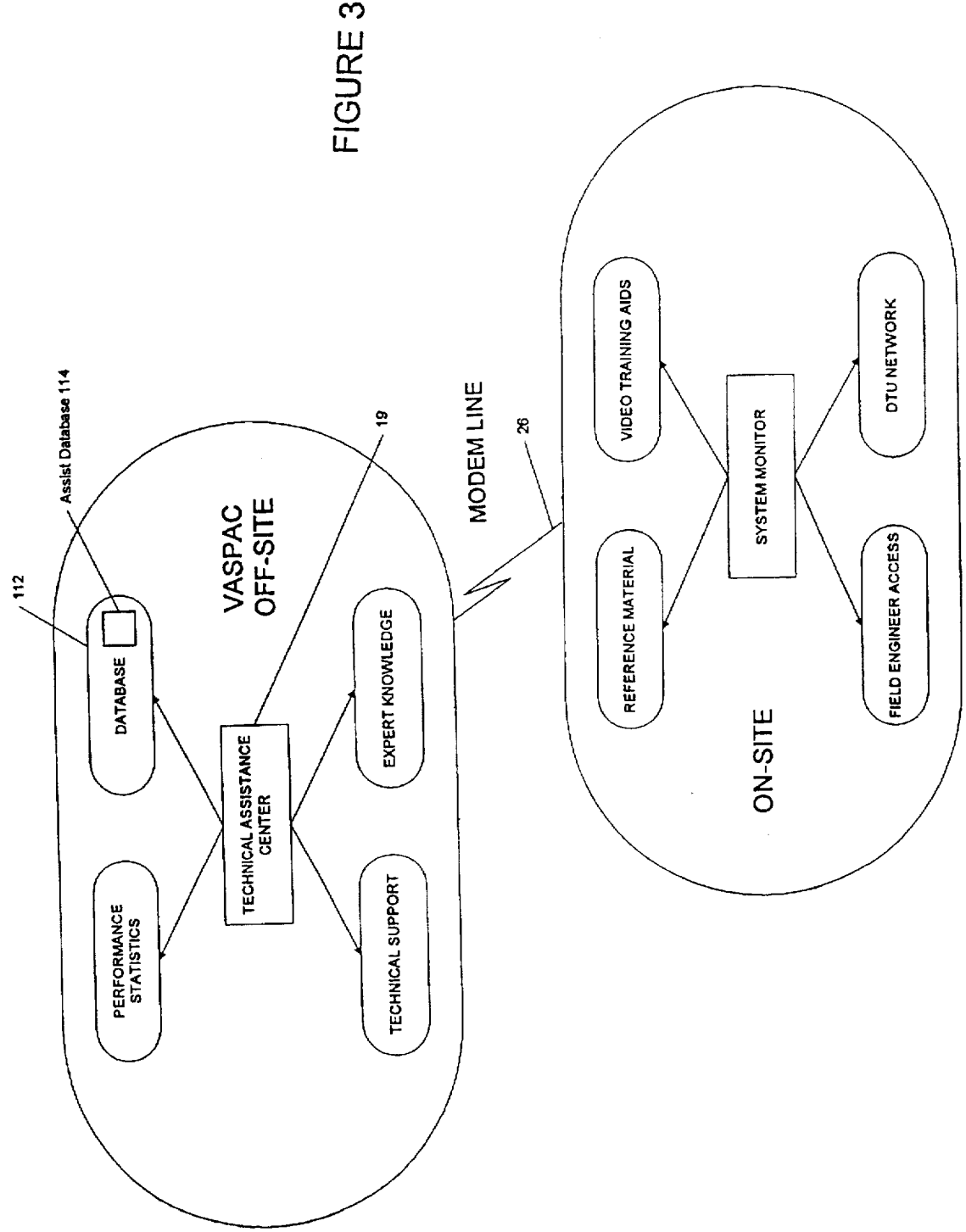
FIG. 3 is a conceptual diagram of the on-site portion of the diagnostic system of the present invention, depicted in the lower circle, and the off-site support provided by the TAC, depicted in the upper circle.

As conceptually shown in FIG. 3 additional technical support, performance statistics, expert knowledge, and external data is available off-site in the TAC 19 by way of a modem link 26, or other suitable data line. The offsite support is available to the on-site field service engineer, and assists in the effective functioning of the diagnostic system of the present invention.

Referring to FIGS. 1 and 2, the ability to sample system data is made possible by DTUs 12 positioned at predetermined test points of the vascular system. For example, DTUs 12 are positioned on the components of the vascular system 14 such as a dosimeter 28, the console 30; the control cabinet 32, and the high tension transformer 34. Each test point has a different DTU which is adapted to monitor particular parameters of the associated component. For instance, the dosimeter 28 has a dosimeter DTU 38 since x-ray dosage information is being gathered. The DTU Network 13 is connected to a master DTU 34 which is connected to the system monitor 16 by a multi-pin cable 36, such as a conventional 25-pin cable.

The DTUs 12 are serially connected in a closed loop with the loop beginning and ending at the master DTU 34. A star combination, shown in FIG. 4, may also be used, which eliminates some of the conceivable shortcomings of a series connection.

In the hardware configuration of FIG. 2 the master DTU 34 has a parallel port 40A, through which it is connected to the system monitor's 16 LPT port 40. The LPT port 40A uses four bits for input and another four bits for output data. The master DTU 34 has an optical receiver & transmitter 54 for communication with the fiber optic network 24. The master DTU 34 converts the digital signals it receives from the system monitor 16 into the optical signals for the DTU network 13. As data is received back from individual DTUs 12, the master DTU 34 converts the signals from optical to digital form and passes them to the system monitor 16 for analysis.

In operation, the master DTU 34 sends data to the first DTU 12 in the loop, the first DTU 12 retransmits the data to the second DTU 12 and so on until the last DTU 12 sends the data back to the master DTU 34 to complete the loop. Cost is the primary advantage of a serial DTU 12 network since only one fiber optic network 24 is required to connect all of the DTUs 12 in the loop.

The disadvantages of this approach are: a) one powered-down DTU can disable an entire network loop; and b) when transmitting, some distortion to the optical pulses may occur which can degrade high speed optical communication to a slower mode. These disadvantages can be addressed by using a combination of star/loop network configurations as shown in FIG. 4.

Figure 4:
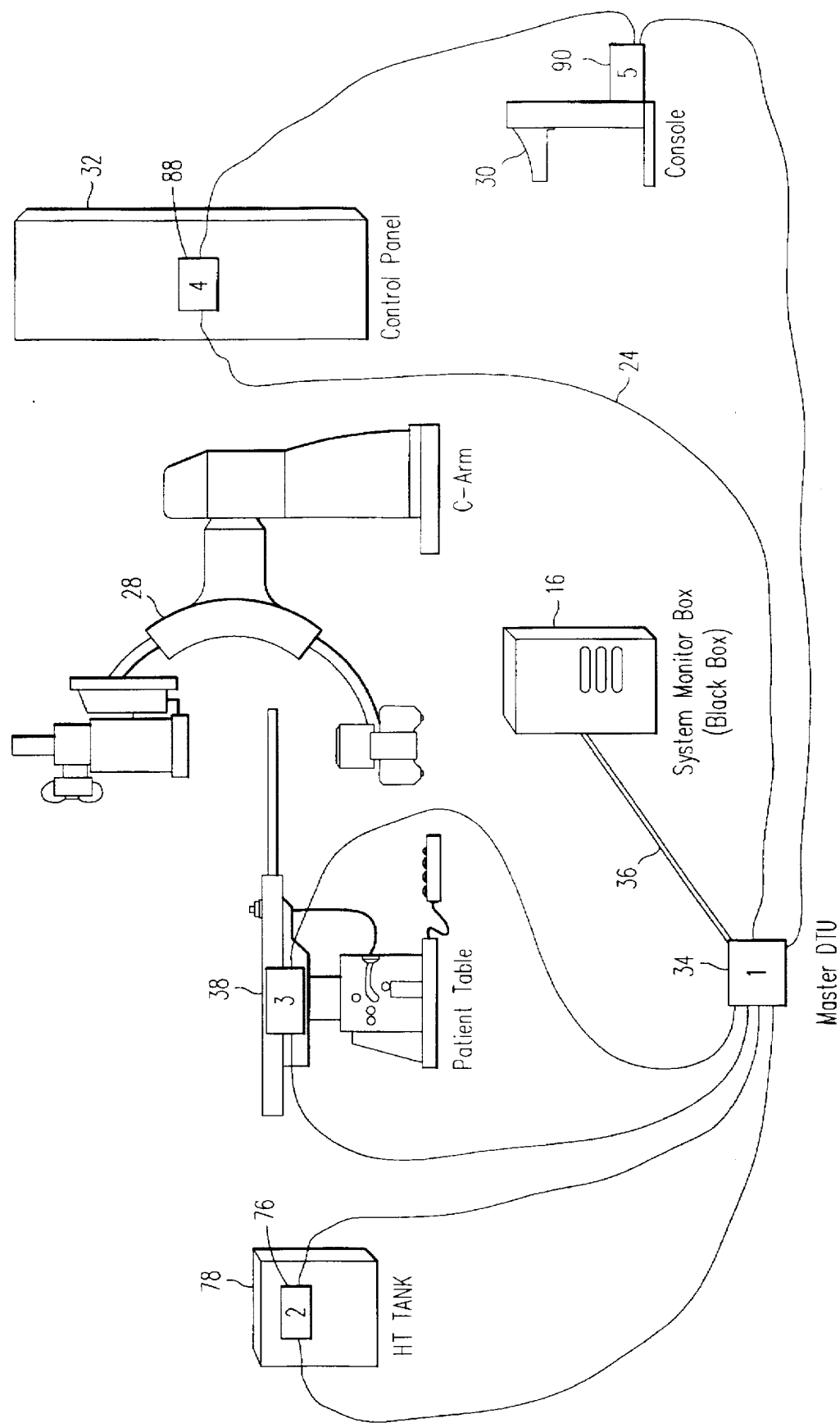
FIG. 4 is a diagram of the diagnostic system of the present invention, configured in a star arrangement.

A star/loop optical network is shown in FIG. 4. This embodiment uses four or more optical input/output channels to allow all DTUs 12 vital to the diagnostic system to be accessed by individual links of the fiber optic cable network 24. Secondary DTUs 12 can also be connected in a loop. Direct access to the primary DTUs 12 prevents one malfunctioning 12 DTU from disabling the entire network. A disadvantage of the star configuration is the additional optical cable required for the separate connections. Each loop can have a dedicated master DTU circuitry assigned to it similar to the master DTU 34 described in connection with the closed loop embodiment of FIG. 2. Alternatively, a multiplex arrangement can be employed in which one set of master DTU circuitry is shared by the various loops.

Distributed Test Units

The DTUs 12 will now be discussed in greater detail with reference to FIGS. 5–11. DTUs 12 are portable data collection units which are designed to be connected to predetermined points on the vascular system 14 without affecting the system's normal operation or the quality of the images produced in the system. DTUs 12 are the "senses" of the diagnostic system of the present invention, which collect data and pass it back to the system monitor 16.

Figure 5:
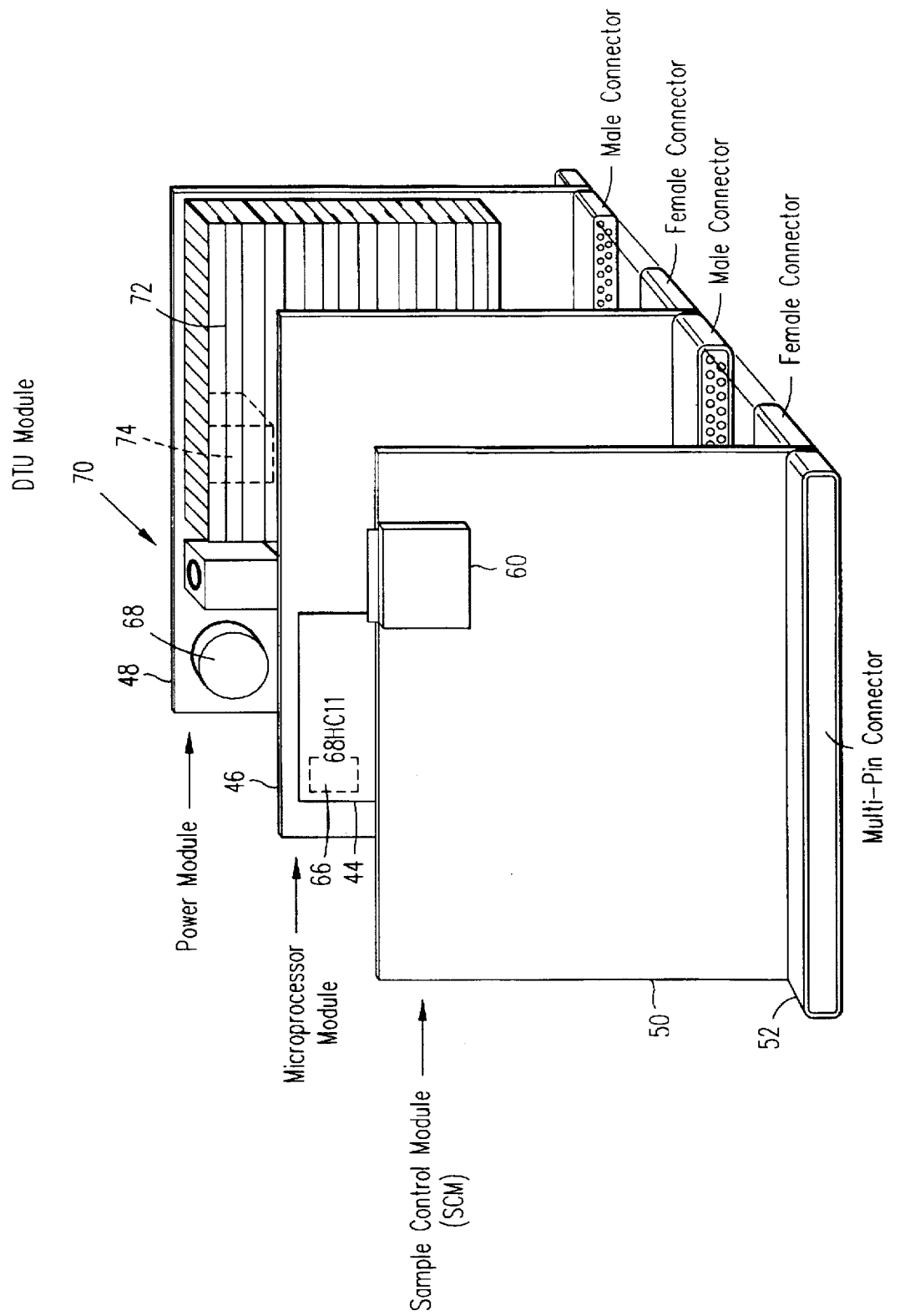
FIG. 5 is a perspective and cross-sectional view of a generalized DTU module.

As shown in FIG. 5, three basic modules are piggy-backed to make up a DTU: 1) a microprocessor module 46 (MM); 2) a power module 48 (PM); and 3) a sample control module (SCM) 50. The modules are preferably connected by stackable multi-pin connectors 52, shown in FIG. 5. A DTU 12 can be tailored to a specific test point by selecting and stacking the appropriate SCM module 50 together with a microprocessor module 46 and a power module 48. The microprocessor 46 and power modules 48 preferably remain constant for each DTU 12. Also included are LEDs 104 (shown in FIG. 1) built into the DTUs 12 which provide status information and indicate whether the DTU 12 is operating after power-up.

The microprocessor module 46 can include a Toshiba 68HC11A0 microprocessor 44, operable off of battery power, with memory and optical input and output capability for connection within the network. The DTU 12 has analog or digital inputs and outputs for connection to a component of the vascular system 12, such as a Dosimeter, at least one pair of which is optical.

Each of the test points of the vascular system 14 at which DTUs 12 are located serve different functions; therefore, different types of SCMs 50 are used. However, the power modules 48 and microprocessor modules 46 are common to each DTU 12. Although the general functions of all DTUs 12 are similar, input requirements and levels of operation (voltages and values) may vary.

The pre-determined test points at which the DTUs 12 are installed, are the points that are deemed most important in achieving the best possible image quality. Each DTU 12 serves several functions, including: 1) listening for commands from the system monitor 16 received through the fiber optic network 24; 2) monitoring input to the test point; and/or 3) controlling a test point so as to maintain a given value. For instance, the DTU 12 can act as a positive feedback control system where the output is fed back as an input until a certain predetermined value is reached. Thus, for example, if the user wants to increase the radiation of the dosimeter 28 to a certain value, the dosimeter DTU 38 increases radiation incrementally until the specified output value is reached.

The microprocessor module 46 is integrated with the power module 48 and a test-point-specific SCM 50. The multi-pin connector 52 provides the necessary signals to control the SCM 50 from the microprocessor 44. The preferred architecture of the microprocessor module 46, shown in FIG. 6, includes: an optical receiver & transmitter 54, a microprocessor 44 such as Toshiba model 68HC11A1 or equivalent, an EPROM 58, a bank of RAM 2000 memory 56A, a bank of RAM 6000 memory 56B, a bank of RAM 8000 memory 56C, and a field programmable gate array (FPGA) 64. The microprocessor 44 communicates over the data/address bus which is connected to the multi-pin connector 52. FIG. 9 provides an example of the multi-pin connector assignments for each of the DTUs 12.

Figure 6:
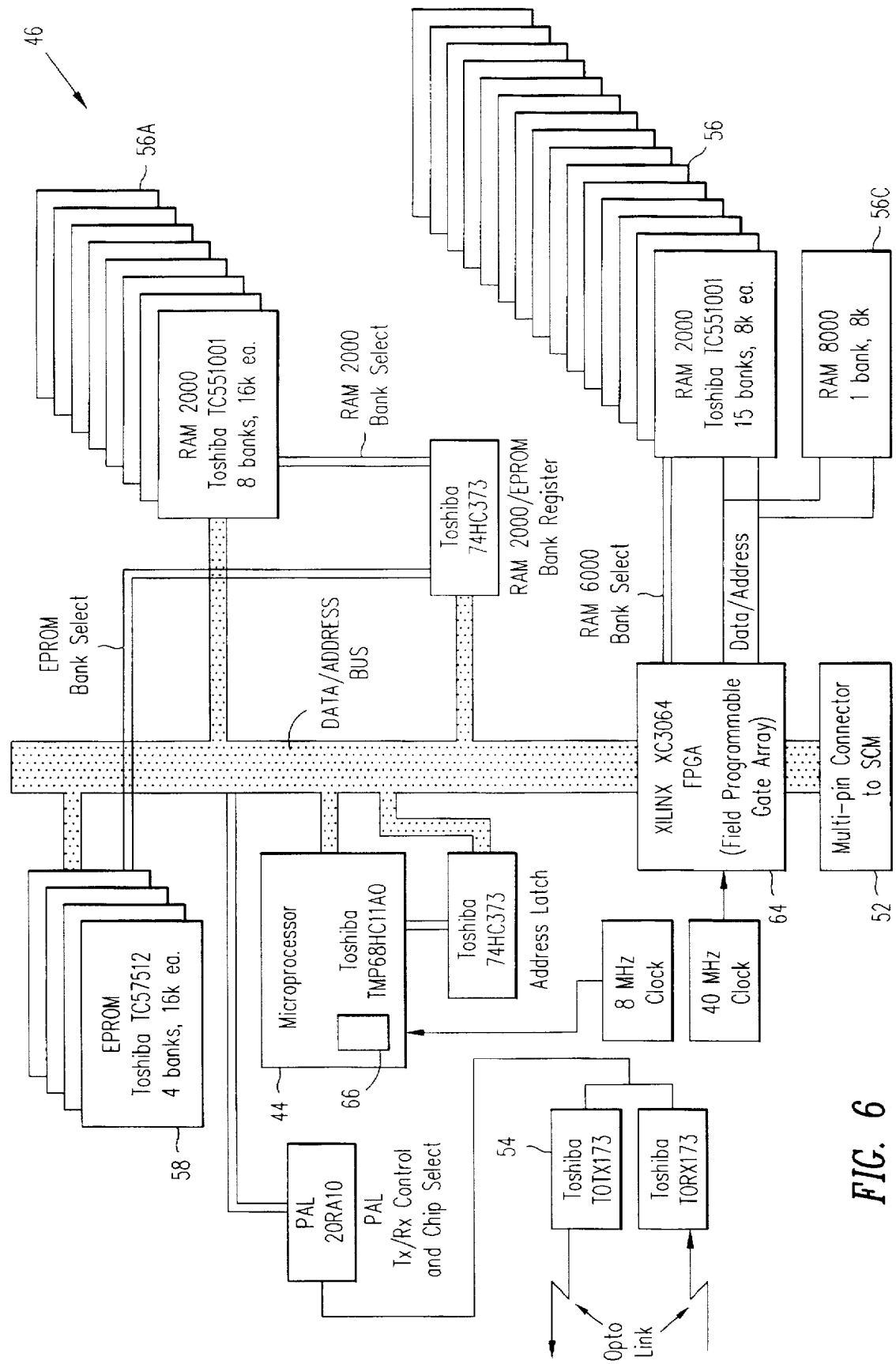
FIG. 6 is functional block diagram of the microprocessor module common to each DTU module.

The optical receiver & transmitter 54 converts light pulses received from the fiber optic network 24 into electrical signals recognized by the microprocessor 44 communication ports. As shown in FIG. 6, microprocessor 44, operating in the expanded multiplexed mode, provides access to external RAM, 56A, 56B, 56C and EPROM 58, and I/Os. A typical microprocessor memory map is illustrated in FIG. 10.

Figure 11:
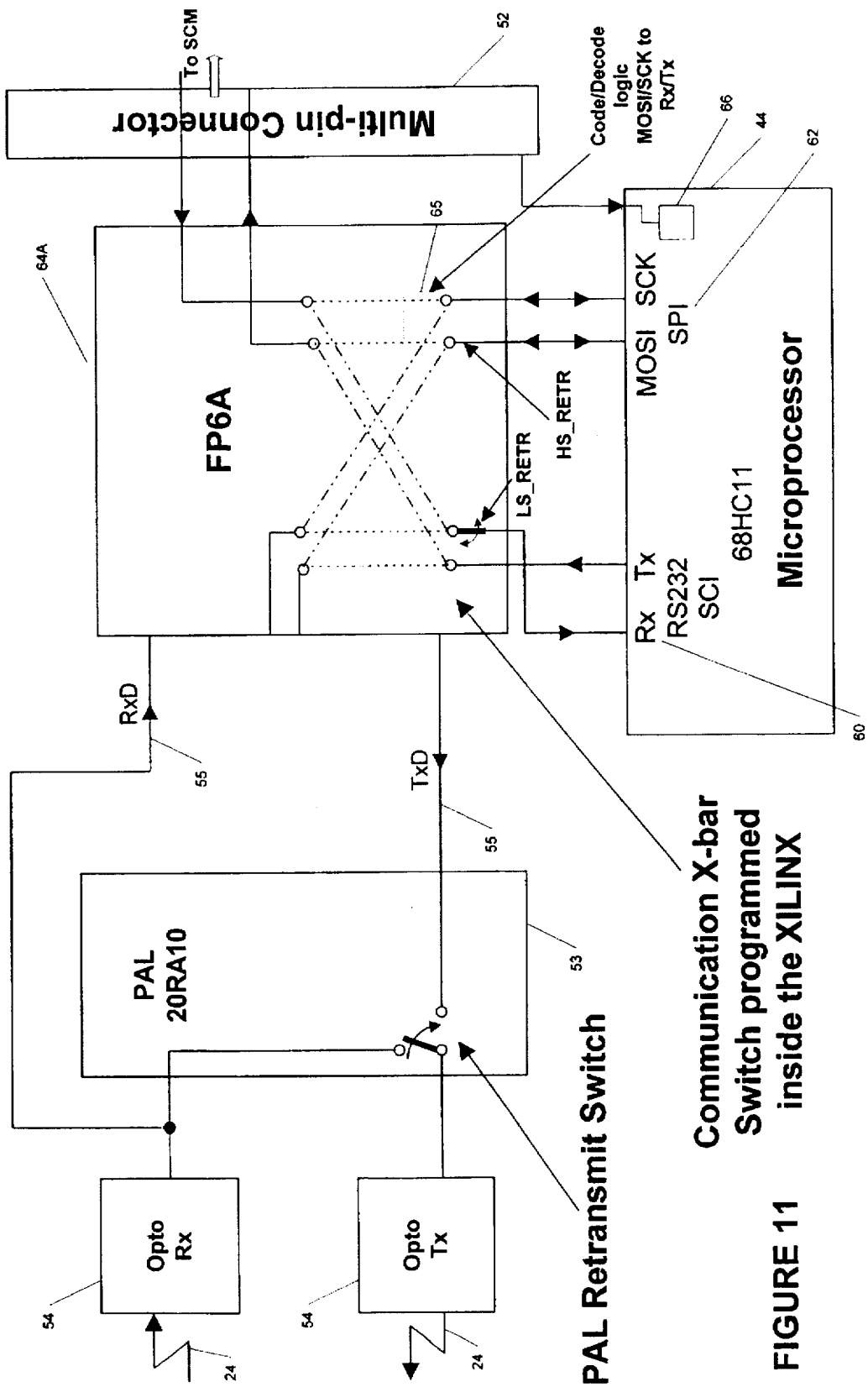
FIG. 11 is a diagram of the communication data flow between the network and a sample control module as controlled by the DTU microprocessor.

Each DTU 12 sends and receives data using two 68HC11A0 serial links in the microprocessor 44: the Serial Communication Interface (SCI or RS232) 60 and the Serial Peripheral Interface (SPI) 62 as shown in FIG. 11. A cross-bar switch 64 is used to connect the optical link, and the electrical link to the test points, to the RS232 60 ports or the SPI 62 ports as dictated by the format of the information being exchanged between the system monitor and the test points. Cross bar switch 64A is implemented as part of the FPGA 64 as shown in FIG. 11. Code/decode Logic 65 converts signals in MOSI/SCK format into Rx/Tx format and vice versa.

Instead of permitting all traffic on the network to pass through microprocessor 44, the SPI 62 receives information from the optical receiver and retransmits the signal to the optical transmitter 54. The retransmitted signal is modulated again to compensate for optical pulse width distortion. (See PAL retransmit switch 53.) In this way, a number of DTUs 12 can be connected in series without accumulating pulse width distortion.

A generic DTU 12, can sample eight analog signals (0 to 2.5V range). Microprocessor 44 is equipped with an internal A/D converter 66. Analog data coming from the test points, travels through the multi-pin connector 52 to the microprocessor 44 which is coupled directly to the multi-pin connector. Analog data is then converted into digital format via the analog/digital convertor 66 within the microprocessor 44. The SCM 50 uses the External Data/Address Bus with Chip Select Logic from the DTU 12 (address range 0800–0FFF, FIG. 7A) to interface with another DTU. The first four ($A_0$–+5V, $A_1$–BATT.1, $A_2$–BATT.2, $A_3$–+12V) input channels monitor the power module 48 (FIG. 5). The first monitors the +5V power supply voltage. The second and third monitor two batteries utilized within the DTU 12. The fourth monitors the internal DC/DC converter voltage. The last four analog channels can sample data from any of the test points.

Figure 7A:
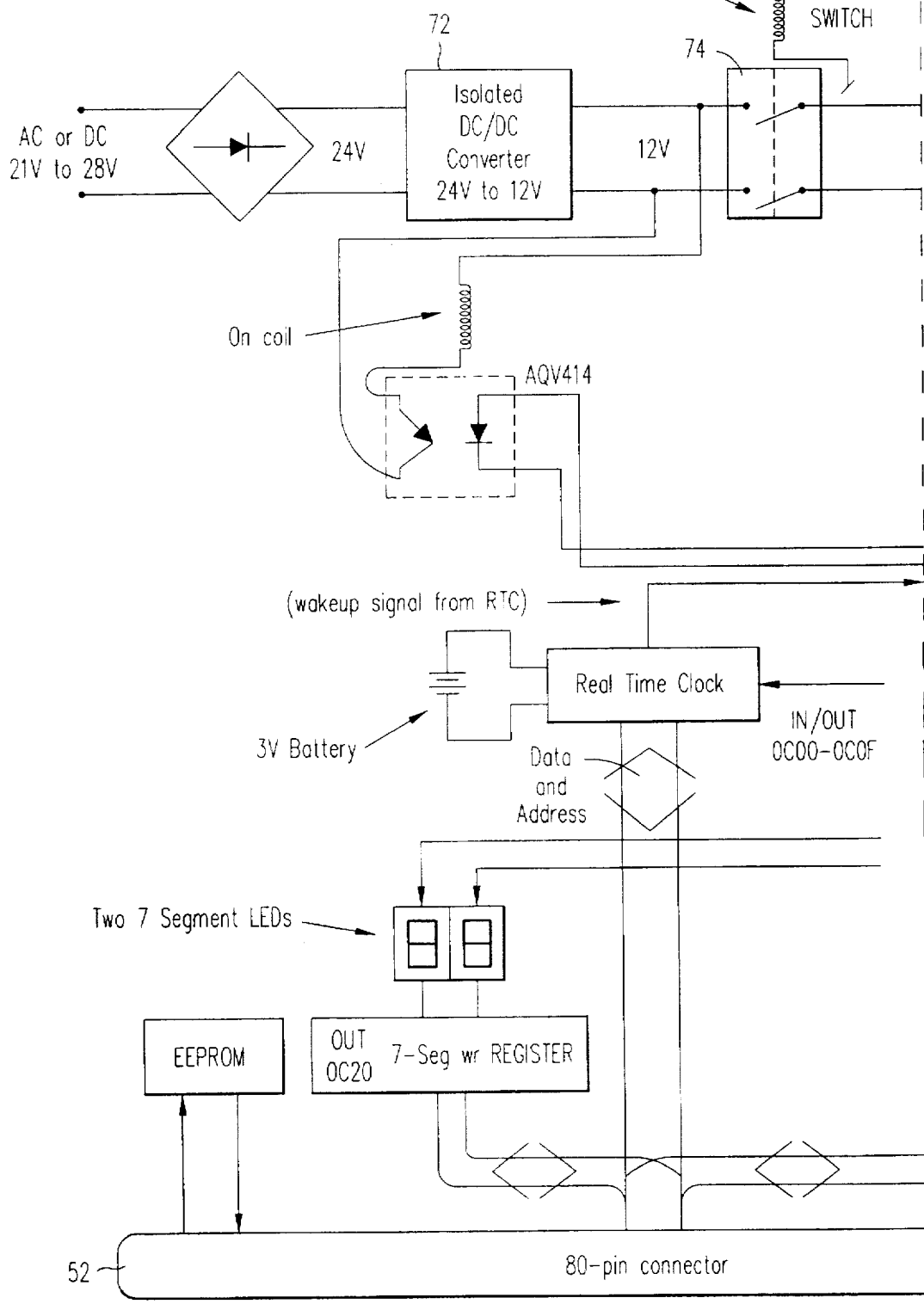
FIG. 7 is functional block diagram of the power module common to each DTU module.
Figure 7B:
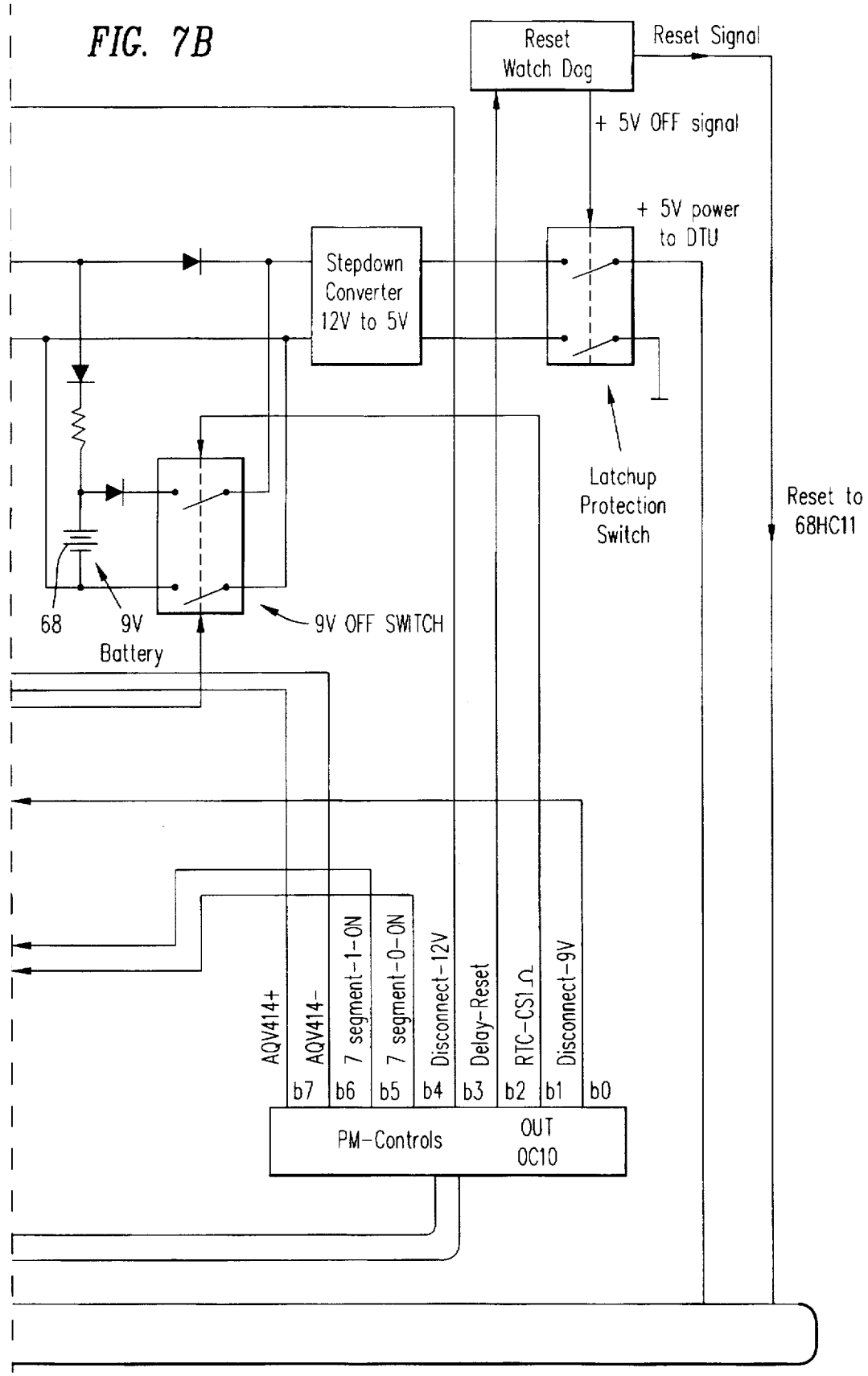

Each DTU 12 is preferably equipped with its own power module 48 having a battery 68 to provide necessary data retention for up to an hour, and a 24v DC input 70 (FIG. 5). The battery is charged from an internal DC/DC converter 72. During "power on" of a DTU 12, the 24V power applied to input 70 can originate either from an external power supply or from one of the DC power lines inside the vascular system 14. The DC/DC converter 72 converts a 24V input voltage into a 12V output voltage with 500 mA maximum current. If a 24V power source is not accessible from the machine, an external wall-plug transformer with 24V DC output is used. The converter has a 500V 3000V IN/OUT isolation rating. A schematic of the power module 48, which is common to each DTU, is shown in FIG. 7.

The power module 48 is connected to the DC/DC converter 72 through a relay switch 74. If a high noise immunity is required, the power module 48 can be physically disconnected from the DC/DC converter 72 and powered from the internal battery 68 for the brief period needed to acquire data during an x-ray exposure.

Figure 8:
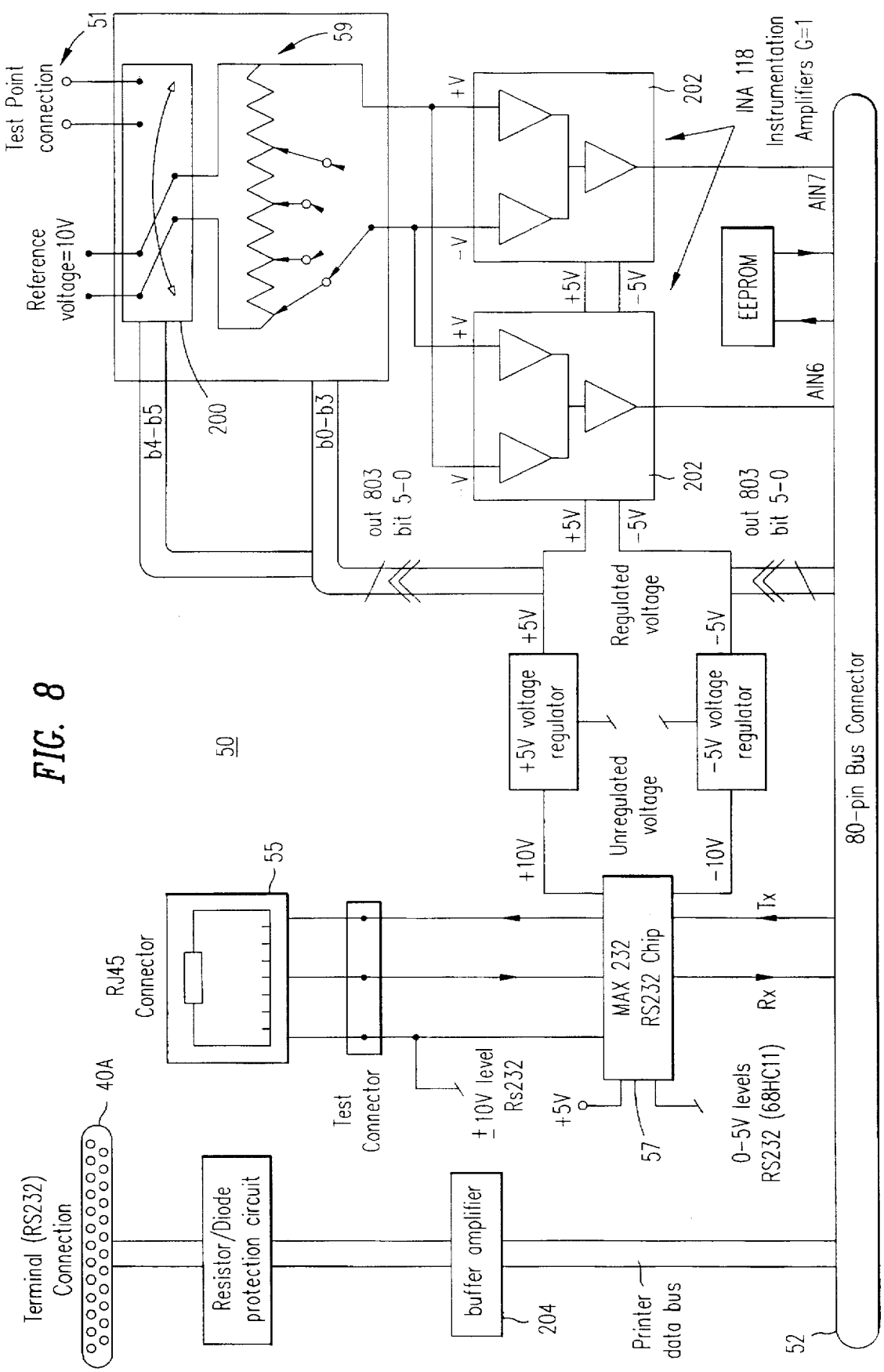
FIGS. 8 is a schematic diagram for the Sample Control Module common to the kV, mA DTU, PMT DTU, dosimeter DTU, and master DTU.

DTUs 12 assume their special qualities from the SCM 50 which they carry. A schematic of the SCM 50, as shown in FIG. 8, is common to the kV, mA DTU 76, the master DTU, the dosimeter DTU 38; and the PMT DTU 80.

As shown by way of example in FIGS. 12A and 12B, the selection of the appropriate SCM 50 allows the generic DTU 12 to function as a dosimeter DTU 38 or another specific DTU type such as a console DTU 88, depending upon its placement in the vascular system 14. (See FIG. 2). Data from the test point, such as from a Dosimeter 28 is received in the DTU 12 through the test point connection 51 on the SCM 50. Switch 200 is controlled by commands on lines B4 and B5 to switch between a reference voltage and the test point signal. Divider 59 provides full scale and scaled levels of the signal from switch 200 to instrumentation amplifiers 202.

Instrumentation amplifiers 202 then drive lines AIN6 and AIN7 on multipin connector 52. The data is then sent through pins AIN6 and AIN7 on the multi-pin connector 52 to the microprocessor module 46. The SCM 50 is equipped with a RS232 connection 55 for communication with a monitor or the field service engineer's laptop computer. A MAX 232 RS232 chip 57 converts the data signal to and from the RS232 format to a ±5V format used by the SCM 50. The following are examples of the types of DTUs 12 and their respective SCMs 50 used in the diagnostic system of the present invention:

kV, mA DTU

The SCM 50 on the kV, mA DTU 76 may be connected to the TERMINAL-A PWB located on a HV Generator Tank 78 (high tension transformer) or to the FEEDBACK PWB (See FIG. 2.) A kV, mA DTU 76 measures voltage and/or amperage at the test point 51. The SCM 50 provides an analog interface between the test points and the DTU 12. A set of operational amplifiers converts the mA signal to a voltage level which is proportional to the current level. Similar circuitry differentiates the +kV/−kV signal to provide an absolute kV signal. The mA amplifier must operate within a 4–1500 mA signal range (Fluoro/Radiography modes). Therefore, programmed amplification ratio is provided through a programmable register divider 59, FIG. 8, in order to accommodate the different ranges.

Photo Multiplier Tube DTU

The photo multiplier tube (PMT) DTU 80 measures the voltage that goes into the PMT 80A. A simple op amp circuit can convert the PMT voltage to the levels measured by the microprocessor module 46 (similar to the kV, mA SCM).

Dosimeter DTU

The Dosimeter DTU 38 (shown in FIG. 12A) is typically connected to the dosimeter 28 to measure the input radiation to the imaging tube. The Dosimeter DTU 38 uses an RS232 link to control the 35050A or equivalent dosimeter 28, set the proper range and mode, request data and transmit that data to the system monitor 16 via the fiber optic network 24. The SCM 50 (shown in FIG. 8) for the Dosimeter DTU 38 is designed for a Keithley dosimeter but can be modified if another type of dosimeter is used. This SCM 50 uses a device similar to a MAXIM MAX 232 to convert 0–5V RS232 levels from the microprocessor 44 to the 9V levels required for the dosimeter 28. The dosimeter 28 is powered only from an internal battery and can not be turned on remotely. An operator must press the POWER ON/OFF button to activate it. However, the dosimeter turns itself off after a user-selected "unattended operation" period of 1 to 255 minutes.

Technique Selector/Console DTU

The Technique Selector (TS/console) DTU 88 (shown in FIG. 2), connected to the operator console 30, queries the operator's console 33 to determine the technique selected by the operator. In addition, it monitors and reports all actions taken by the user. For example, it monitors and records technique selections such as the kV, mA settings, focal spot selections and x-ray tube selections, etc. The kV, mA stations or techniques can be selected and verified remotely from the TS DTU 88 without operator intervention, allowing full automation of numerous procedures. As discussed later, calibration of the vascular system 14 can be verified by comparing the DTU 12 measurements with the operator console 33 settings.

The TS/Console DTU 88 also drives auto-testing of the operator's console 33. Using the test point measurements reported by the DTUs 12 the diagnostic system of the present invention can then compare these measurements with the settings recorded at the operator console 88 by the Technique Selector DTU 88 to assure accuracy.

Master DTU

The master DTU 34, shown in FIG. 2, is the first and last DTU 12 in the loop. The master DTU 34 provides protocol conversion/data buffering between the system monitor 16 and the fiber optic network 24. The SCM 50, schematically shown in FIG. 8, for the master DTU 34 provides the necessary signals to link the master DTU 34 with the LPT port 40 of the system monitor 16 via a parallel port 40A. Standard Lap-LINK or Interlink protocols are used for this communication. The SCM 50 for the master DTU 34 utilizes a buffer 204 for the digital signals between the multi-pin connector 52 and the LPT port 40 of the system monitor 16.

Eight (8) data lines and one (1) strobe line are used to send input signals from the system monitor LPT 40 to the master DTU 34 parallel port SELECT, PAPER END, ACKNOWLEDGE, BUSY, and ERROR signals are used as the output signals from the master DTU 34 to the system monitor 16. The master DTU 34 uses an RS232-like protocol to gather 4-bit (+1 strobe) nibbles and pack them into blocks acceptable to the network protocol. This allows a standard LPT port 40 to be used to simplify communication between the system monitor 16 and the fiber optic network 24.

The diagnostic system of the present invention can be configured without the master DTU 34 by replacing it with circuitry inside the system monitor which provides high speed optical communication between the system monitor 16 and the DTU Network 13.

System Monitor

The system monitor 16 (shown in FIGS. 1–2 and 13), through a master DTU 34 controls all of the other DTUs, 12 and queries the DTUs 12 for information and processes the data they send back to it. The system monitor 16 can communicate individually with any of the DTUs 12. The system monitor 16 sends requests/commands to the DTUs 12; in response, the DTUs 12 gather sample data from the equipment to which they are assigned, respectively. The system monitor 16 can determine when changes are occurring in the vascular system 14 by analyzing the data provided by the DTUs 12. The system monitor 16 can also command a DTU 12 to reconfigure itself to another type of DTU 12.

Figure 13:
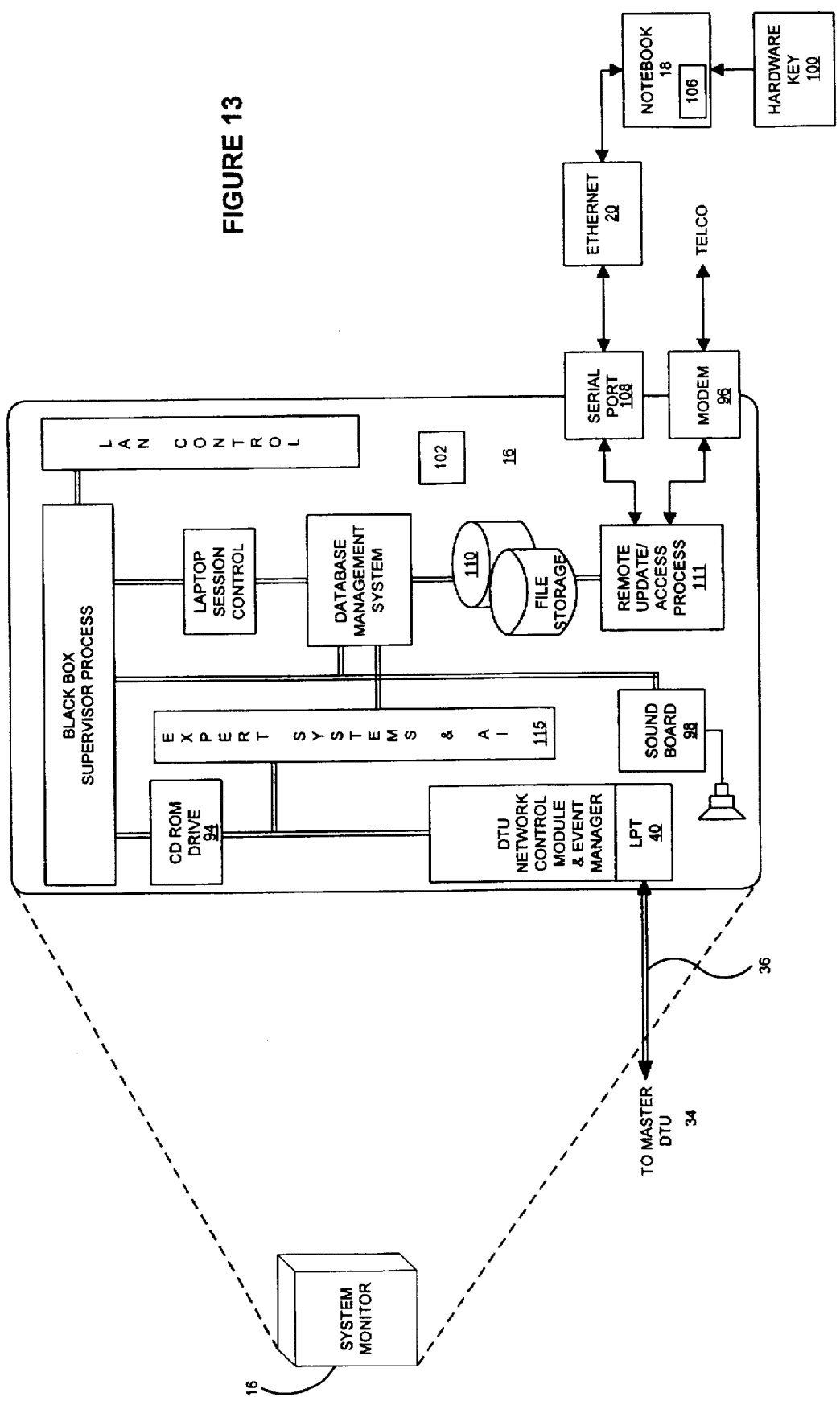
FIG. 13 is a conceptual diagram of the functions performed by the system monitor.

The system monitor 16, shown conceptually in FIG. 13, is a computer having a parallel port interface (LPT) port 40 for connection to the master DTU 34 via a multipin cable connector 36, and an ethernet connection 20 for connection to the field service notebook 18. The system monitor 16 hardware includes a CD-ROM storage 94 or equivalent; multimedia capability; a modem 96; an Ethernet connection 20; a sound board with speakers 98; graphics capability; a hardware key 100; and a bar code reader 102. The system monitor 16 may also boot from the CD-ROM 94. The system monitor 16 preferably operates on a "Microsoft" Windows-based software. It may also operate on next generation software platforms such as WINDOWS '95 or UNIX.

As shown in FIG. 13; the system monitor 16 controls all of the major system functions of the diagnostic system. All of the information and functions necessary to run the diagnostic system of the present invention 10 with the exception of the software graphical user interface (GUI) 22, shown in FIGS. 29A; 29B, 29C, 29D; and 29E, are contained within the system monitor 16. Current and past performance information files for this system are stored in the on-site database 110. The remote access capability 111 that allows this site to talk to and be monitored by the TAC 19 is contained in the system monitor 16. The CD-ROM 94 contains documentation (manuals and procedures), equipment specifications and video support necessary to perform site service activities.

The remote access function 111 also enables remote users to transfer files from the system monitor 16, e.g., error logs, site history information, access the system monitor 16 database, execute remote functions such as diagnostics or DTU 12 control, receive software revision information, schedule execution of DTU 12 control functions (i.e. a remote command to the system monitor 16 such as "sample DTU #2 every ten seconds), and schedule system performance execution. The system monitor 16 also runs self-diagnostics, and diagnostics on CD-ROM access, the DTU 12 network, the LPT port 40, the serial port 108, and the ethernet connection 20.

When the field service engineer connects the field service notebook 18 to the system monitor 16 via the ethernet connection 20, network data can be accessed. Diagnostics are provided through the system monitor 16 for troubleshooting and maintaining the DTUs 12. The system monitor 16 also assists the field service engineer with diagnostic procedures. Both the field service engineer and the TAC 19, can contact the system monitor 16 remotely via modem 96 to access the DTU 12 network and check system operations. The system monitor 16 may also initiate contact with the TAC 19. The TAC 19 may also send electronic mail or technical bulletins to the system monitor 16 to be read by the field service engineer.

After the system monitor 16 has analyzed data sent to it from the DTUs 12, it can automatically send the results via modem 96 to the TAC 19. If, for some reason, the TAC 19 line is busy, the system monitor 16 spools (queues) the data for later transmission. The system monitor 16 also allows users to schedule the sending of data logs and files from the system monitor 16 to the TAC 19. For example, the system monitor error log and activity log may be scheduled to transmit every eight hours.

The system monitor 16 can analyze test point data such as dose, signal amplitudes, resolution, and field uniformity sent to it from the DTUs 12. At installation or calibration, the field service engineers enter acceptable values for each of the parameters (test points). Acceptable dose values, for example, could be between 0.08–0.09. These values, once entered, are stored in the system monitor database 110. When directed to do so, the system monitor 16 reads current values from the corresponding DTU, such as the Dosimeter DTU 38 then passes the value read to an expert system residing in the system monitor 16. The expert system 115 compares the values read to the values set and determines whether the values are within the acceptable range. Decisions made by the expert system 115 then determine what procedures or actions the user is next prompted to take during repair and maintenance of the vascular system.

Figure 14:
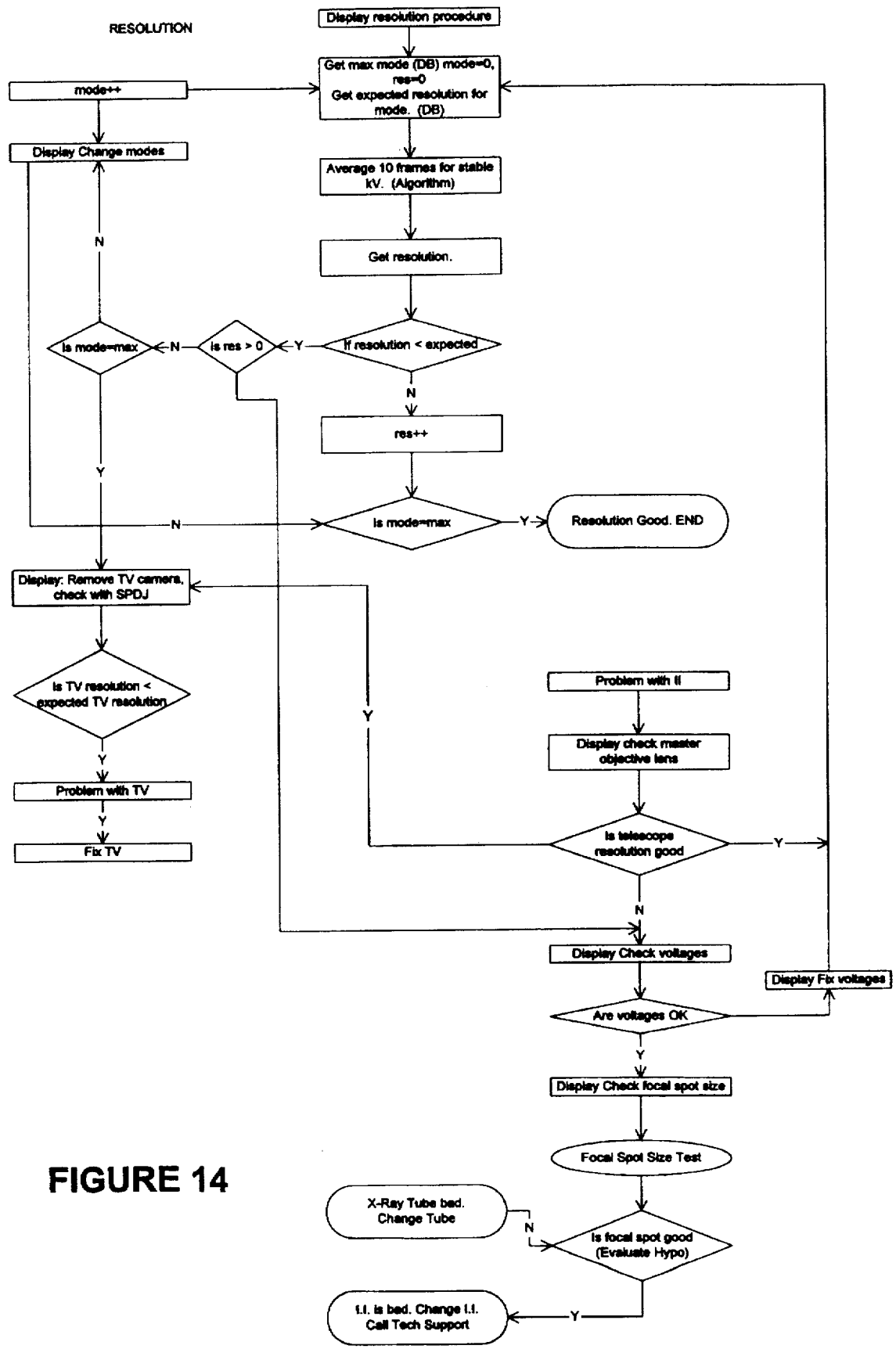
FIG. 14 is a flow diagram of the Resolution procedure.

The system monitor 16 can run a multitude of diagnostic procedures which reduce the guess-work of system repair. As shown by the way of example in FIG. 14, the "Resolution Procedure" guides the field service engineer through an analysis process to correct the resolution of images. Video images, from an x-ray, such as of small arteries are displayed on screen for a physician's review. Sometimes the quality of the image is poor such that it is of little or no value to the physician. In such a case, the poor image could be caused by a bad image tube, which costs about $40,000 to replace, or it could be a bad x-ray tube, which costs significantly less.

Figure 16A:
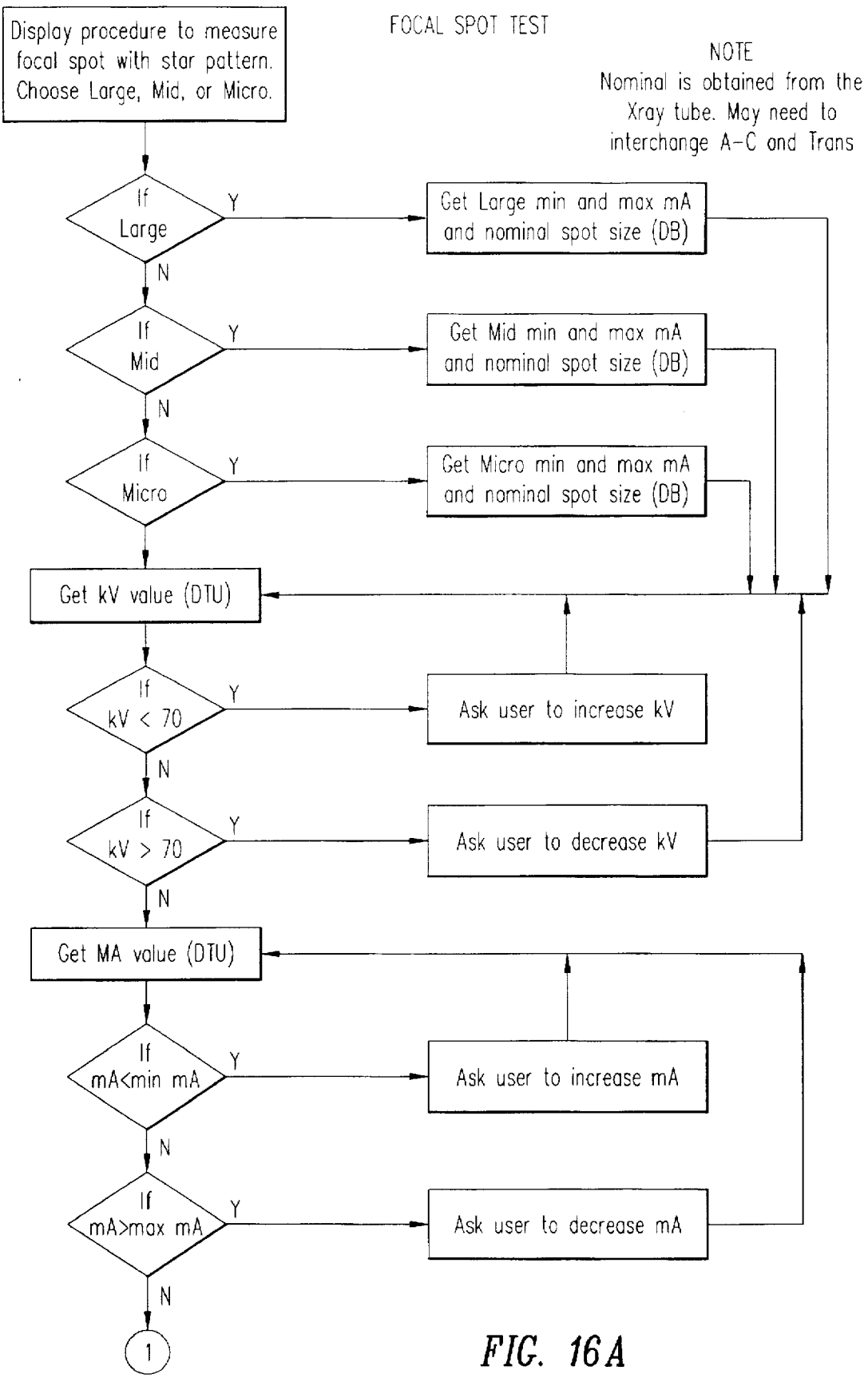
FIG. 16A and 16B are flow diagrams showing the Focal Spot Test procedure.
Figure 16B:
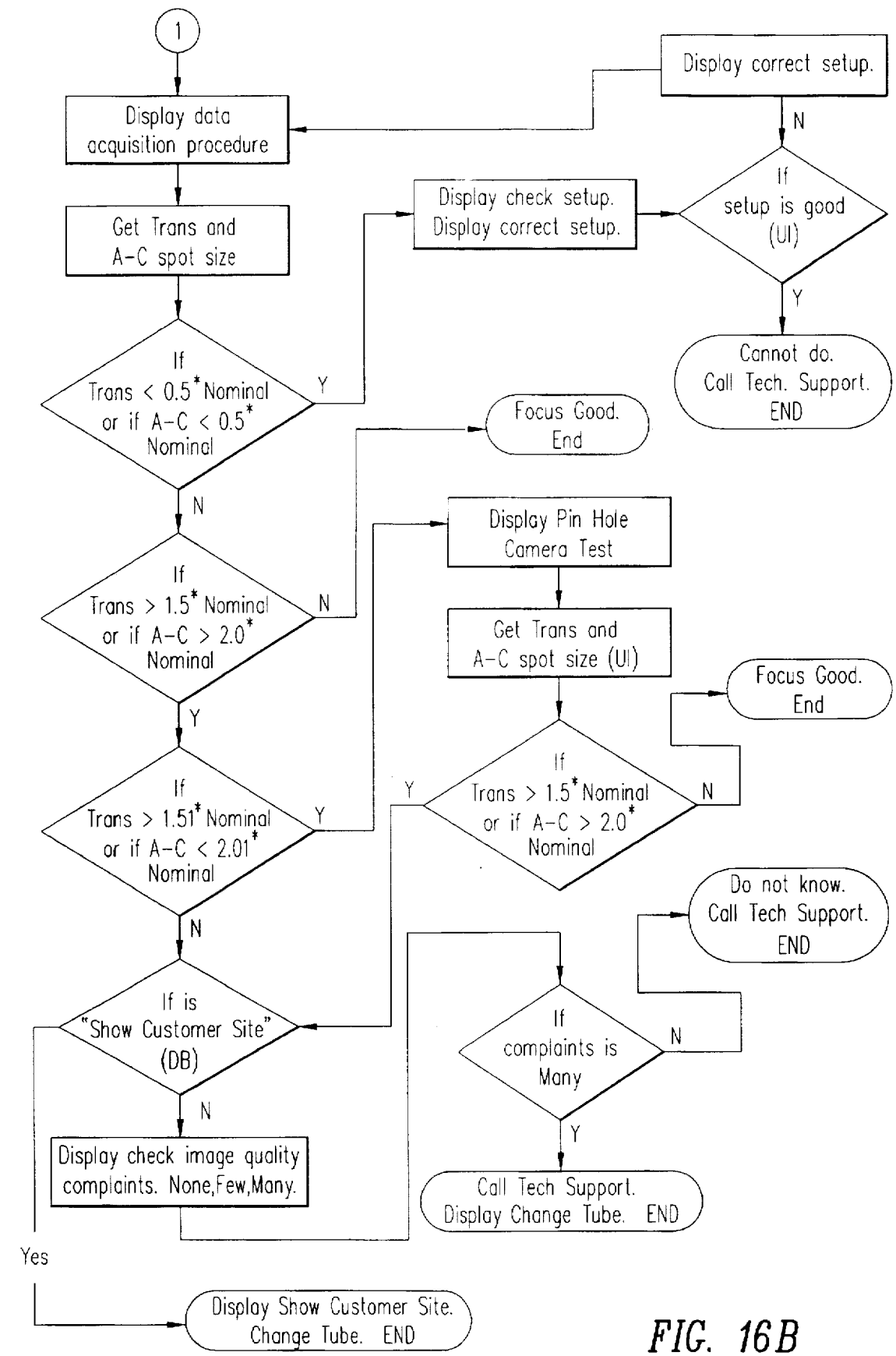
Figure 17A:
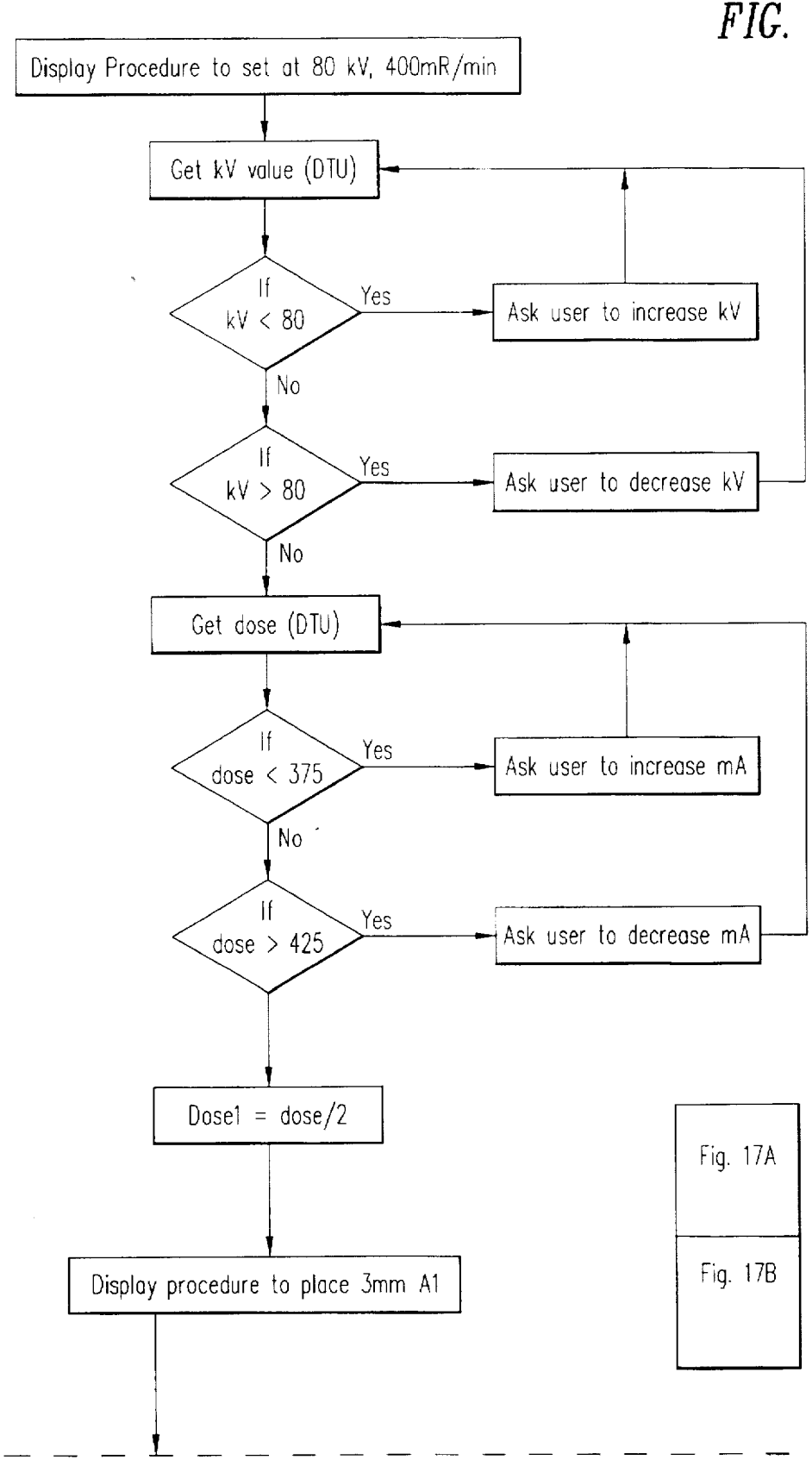
FIG. 17 is a flow diagram showing the Half Value Test procedure.
Figure 17B:
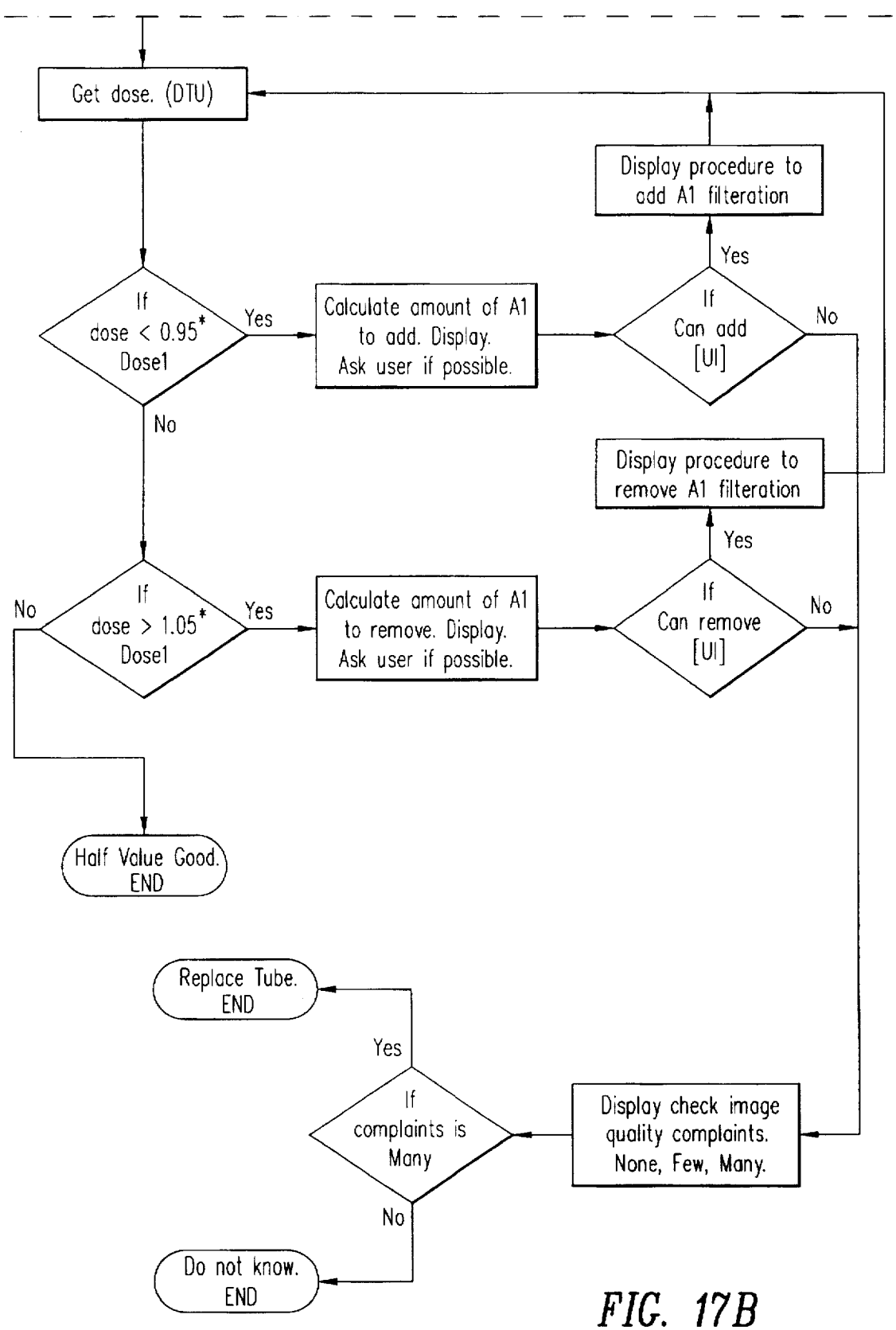
Figures 2, 18A:
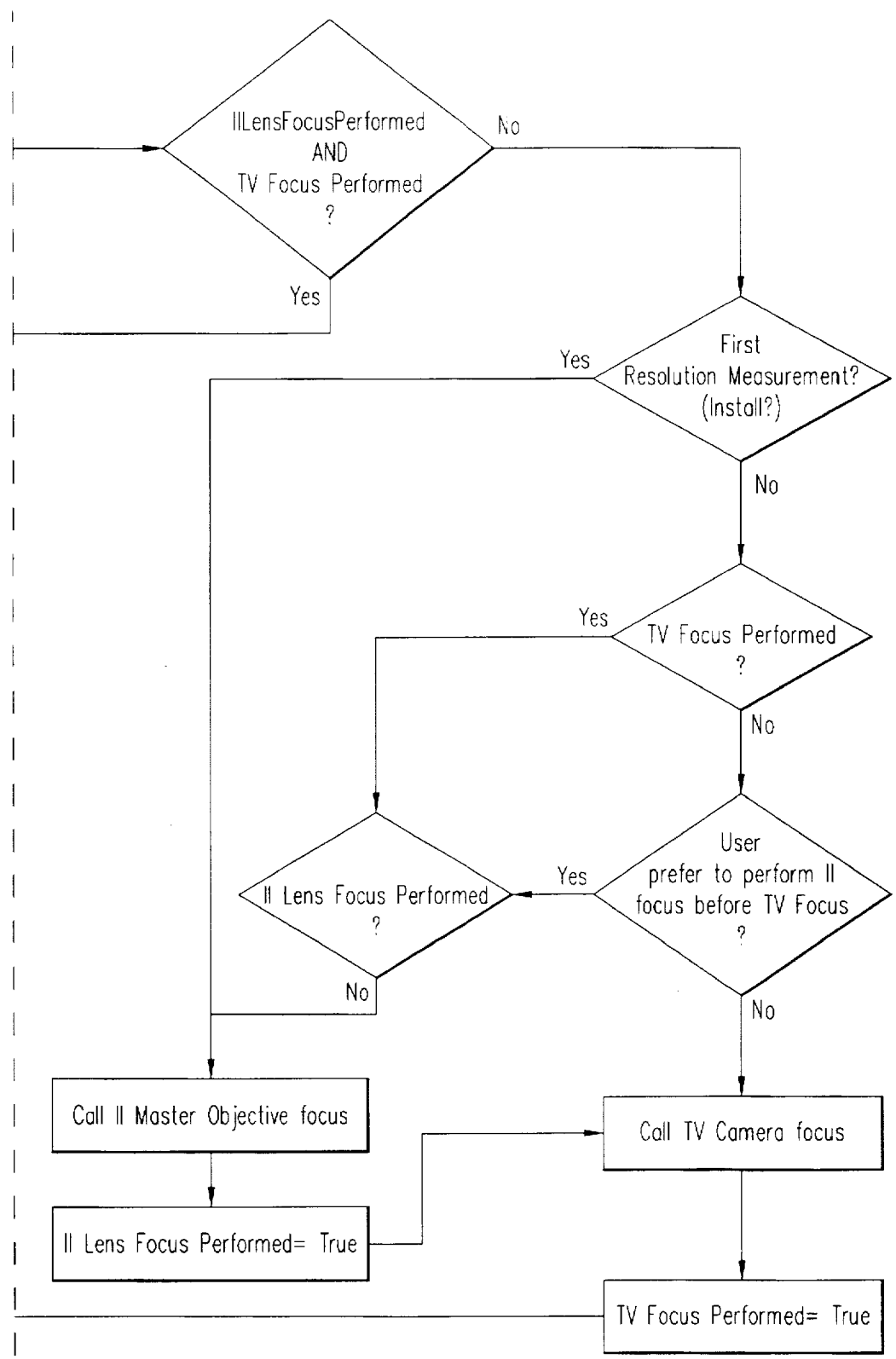
FIG. 18A and 18B are flow diagrams showing the Quick Tube Calibration Check procedure.
Figure 18B:
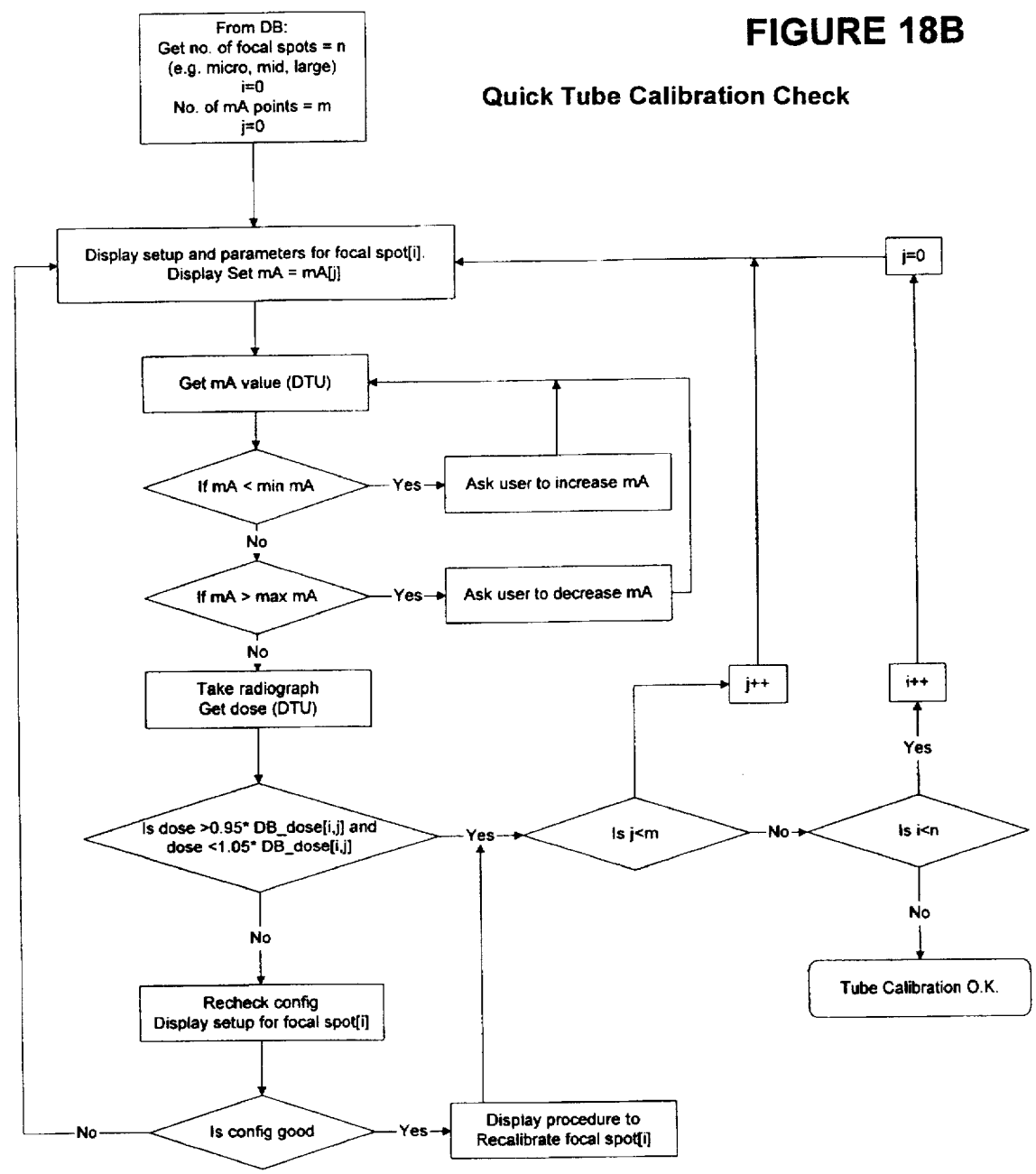
Figure 19:
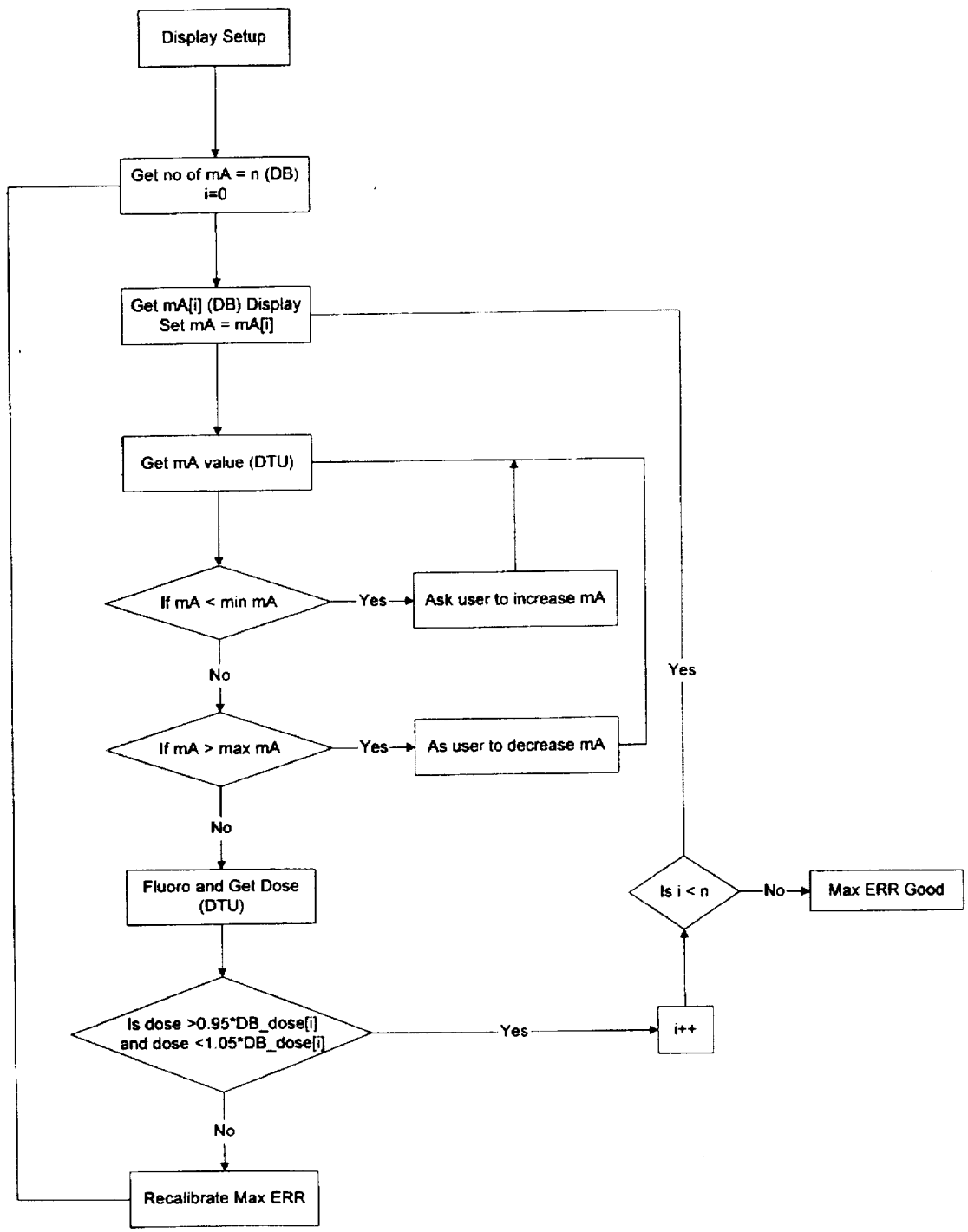
FIG. 19 is a flow diagram showing the Check Max ERR procedure.
Figures 2, 20A:
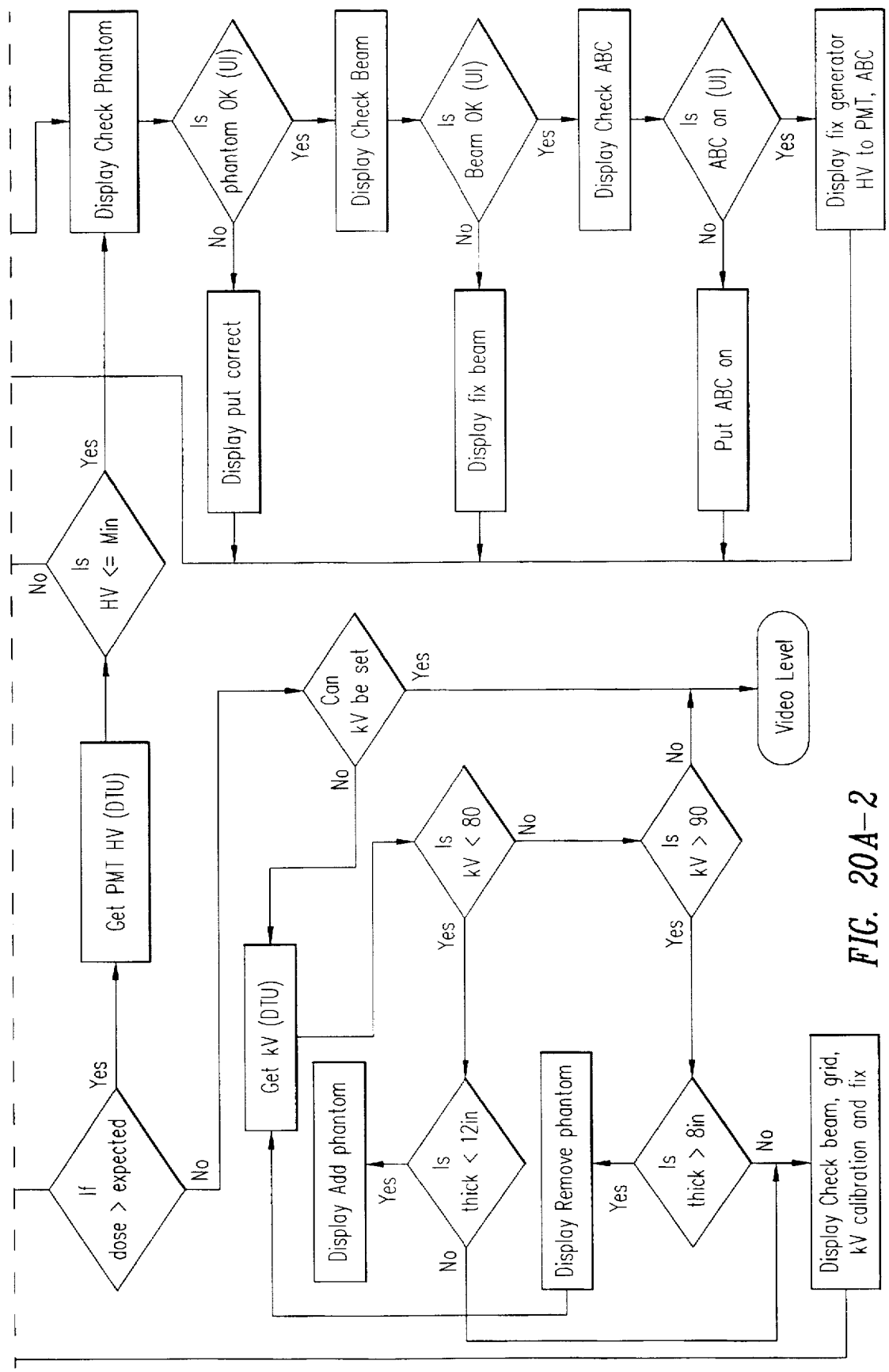
FIGS. 20A, 20B, and 20C are flow diagrams showing the Flouro Dose Data procedure.
Figures 2, 20B:
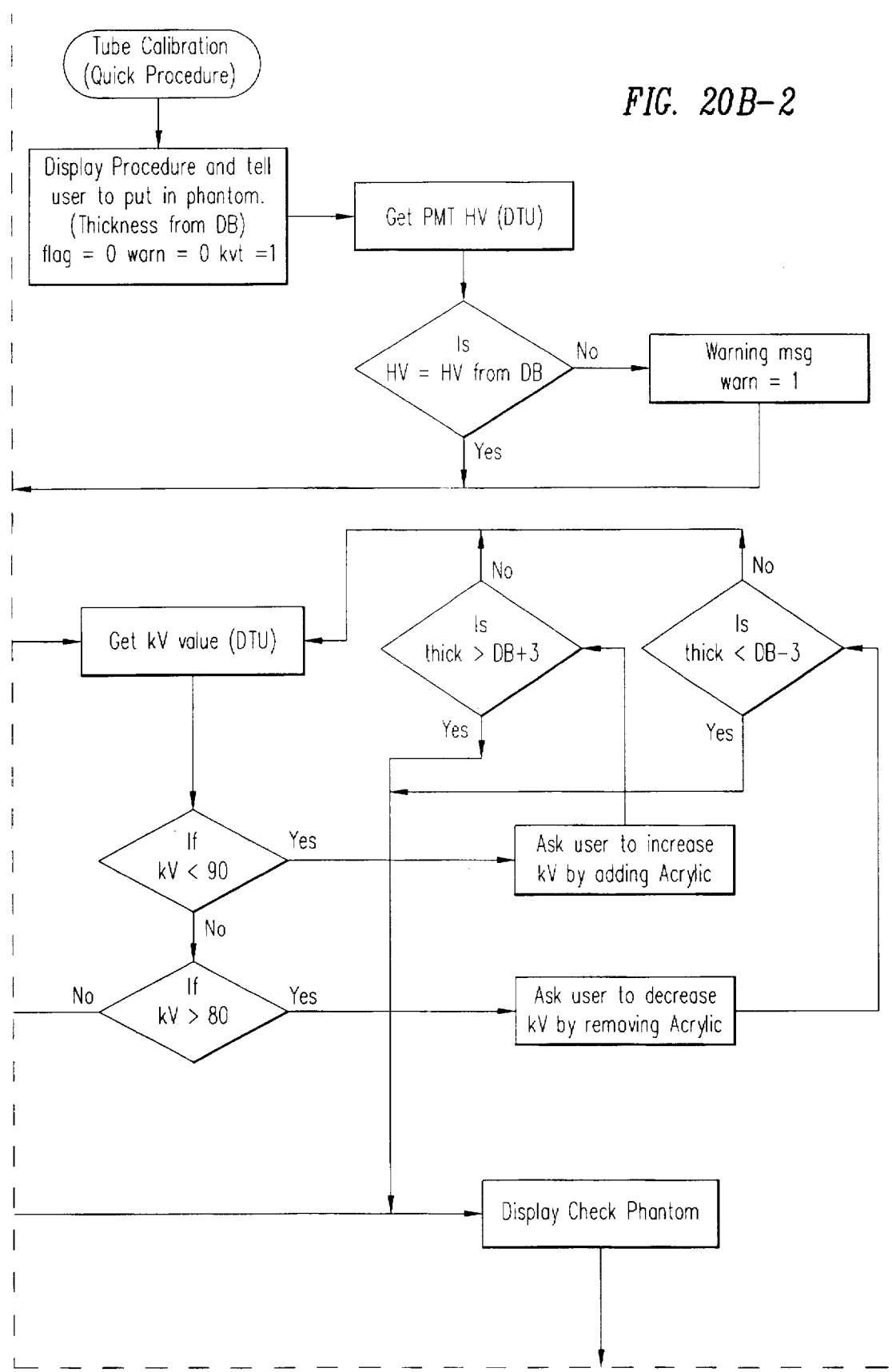
Figures 3, 20B:
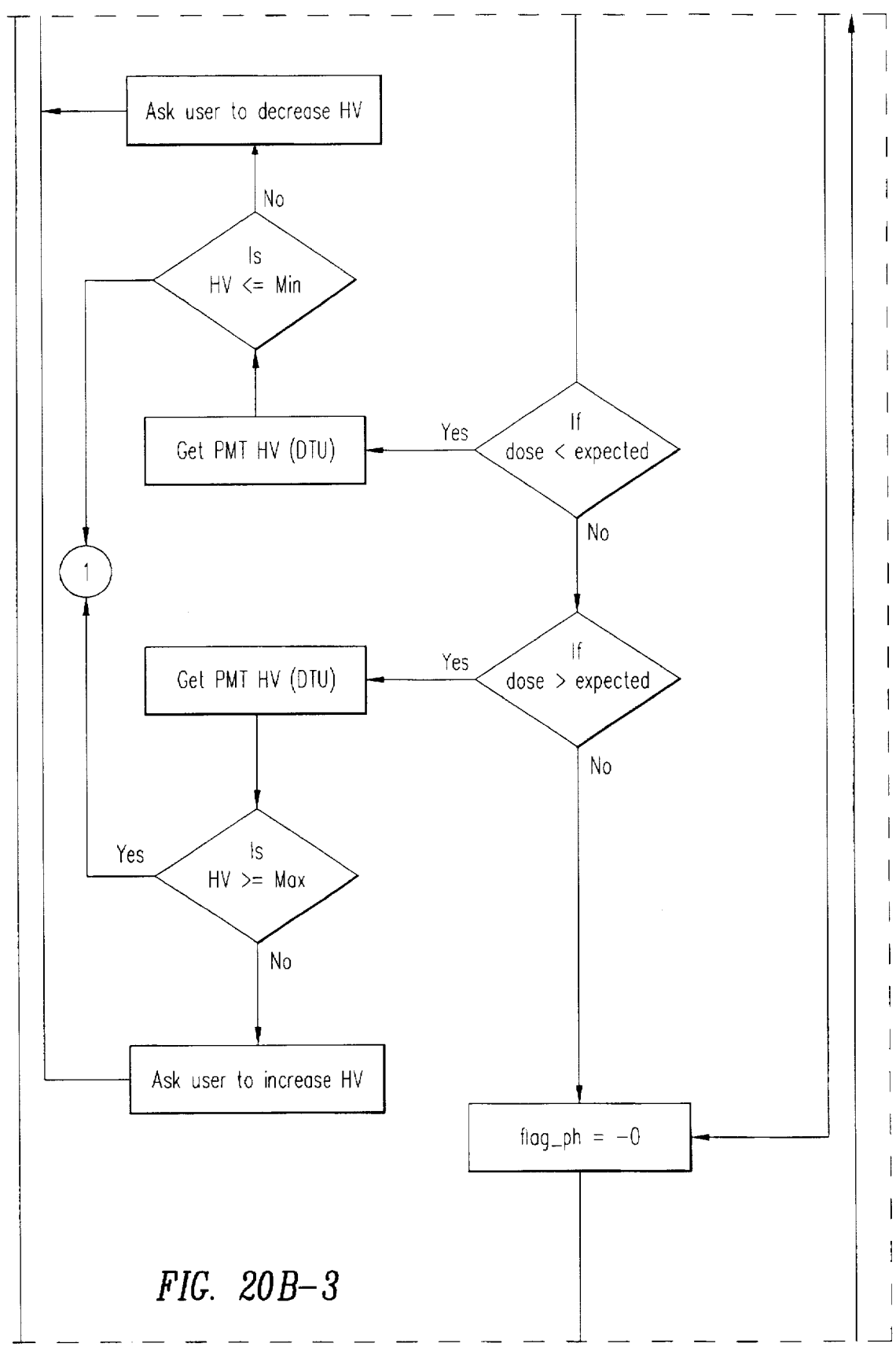
Figures 4, 20B:
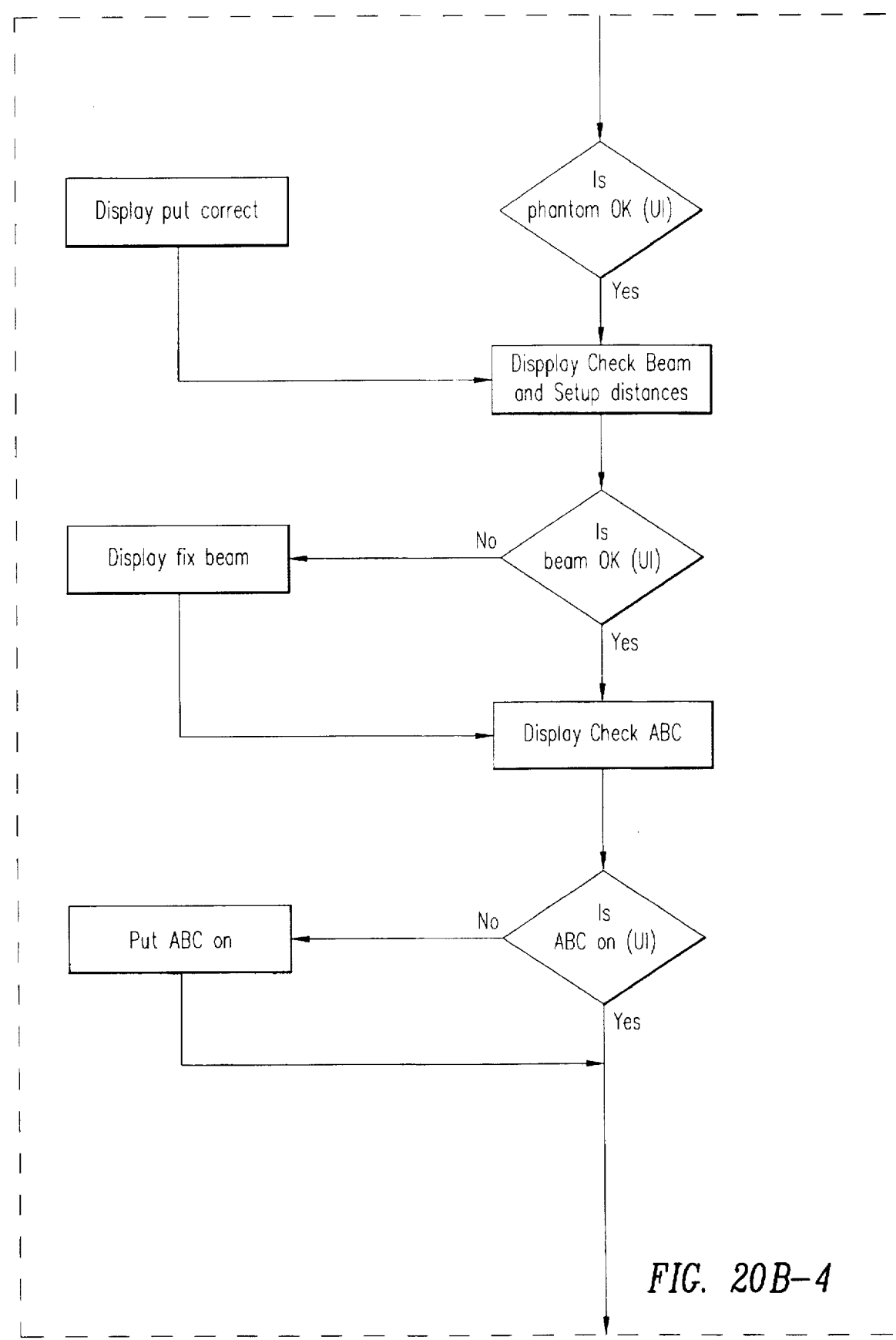
Figures 5, 20B:
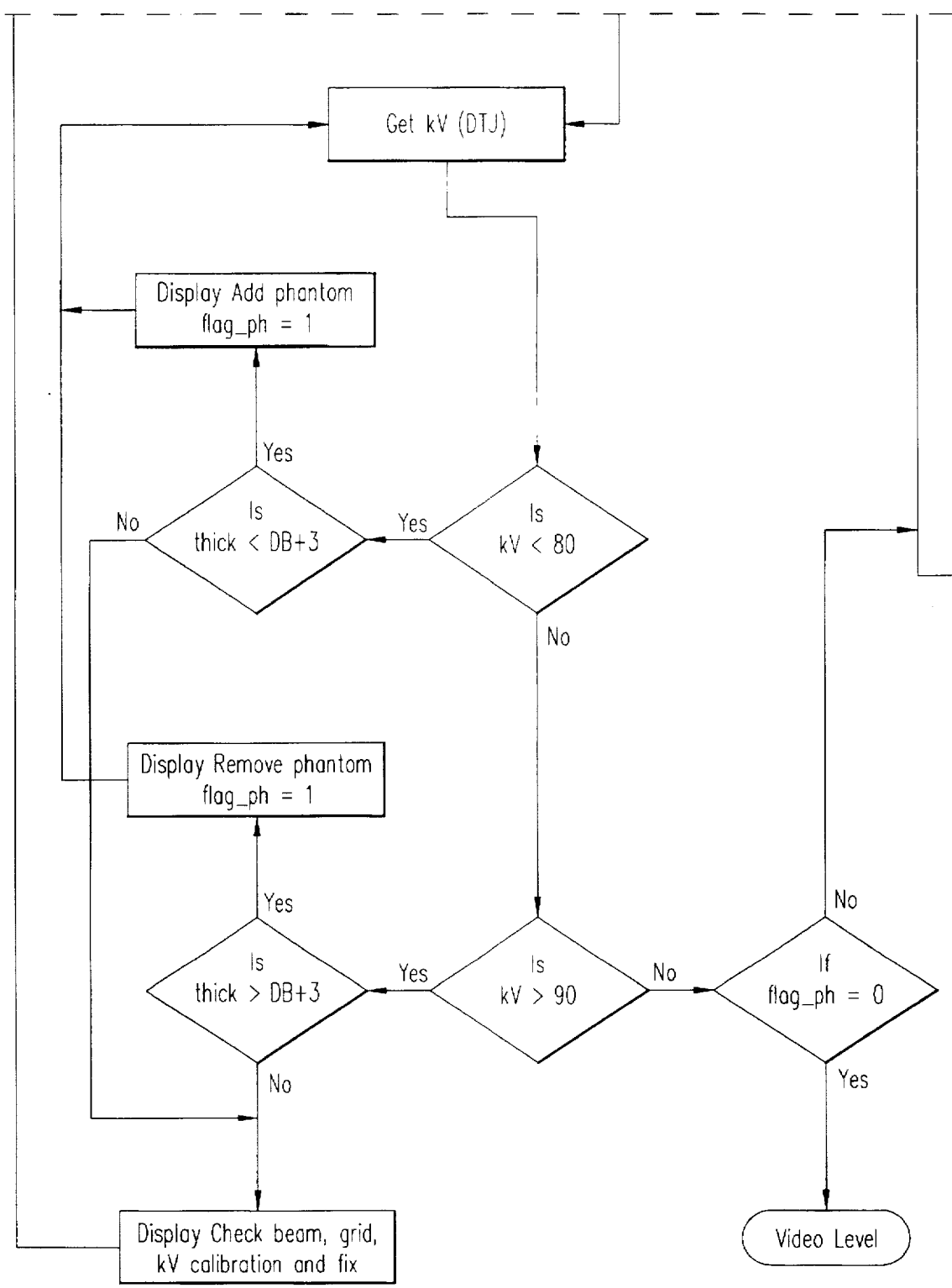
Figure 20B:
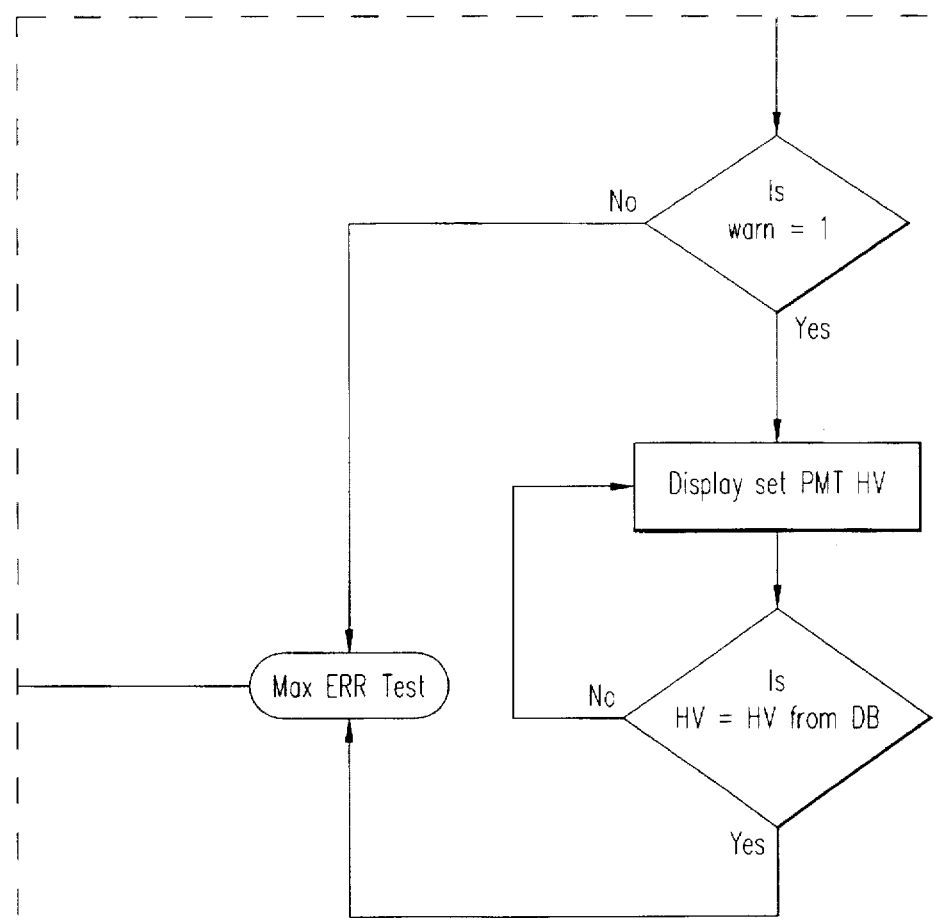
Figure 6:
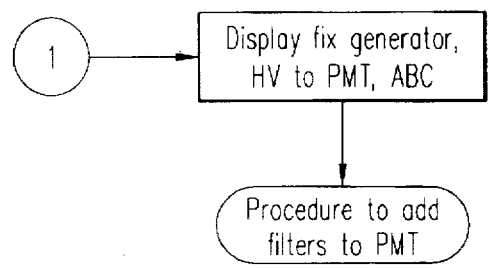
Figures 1, 20C:
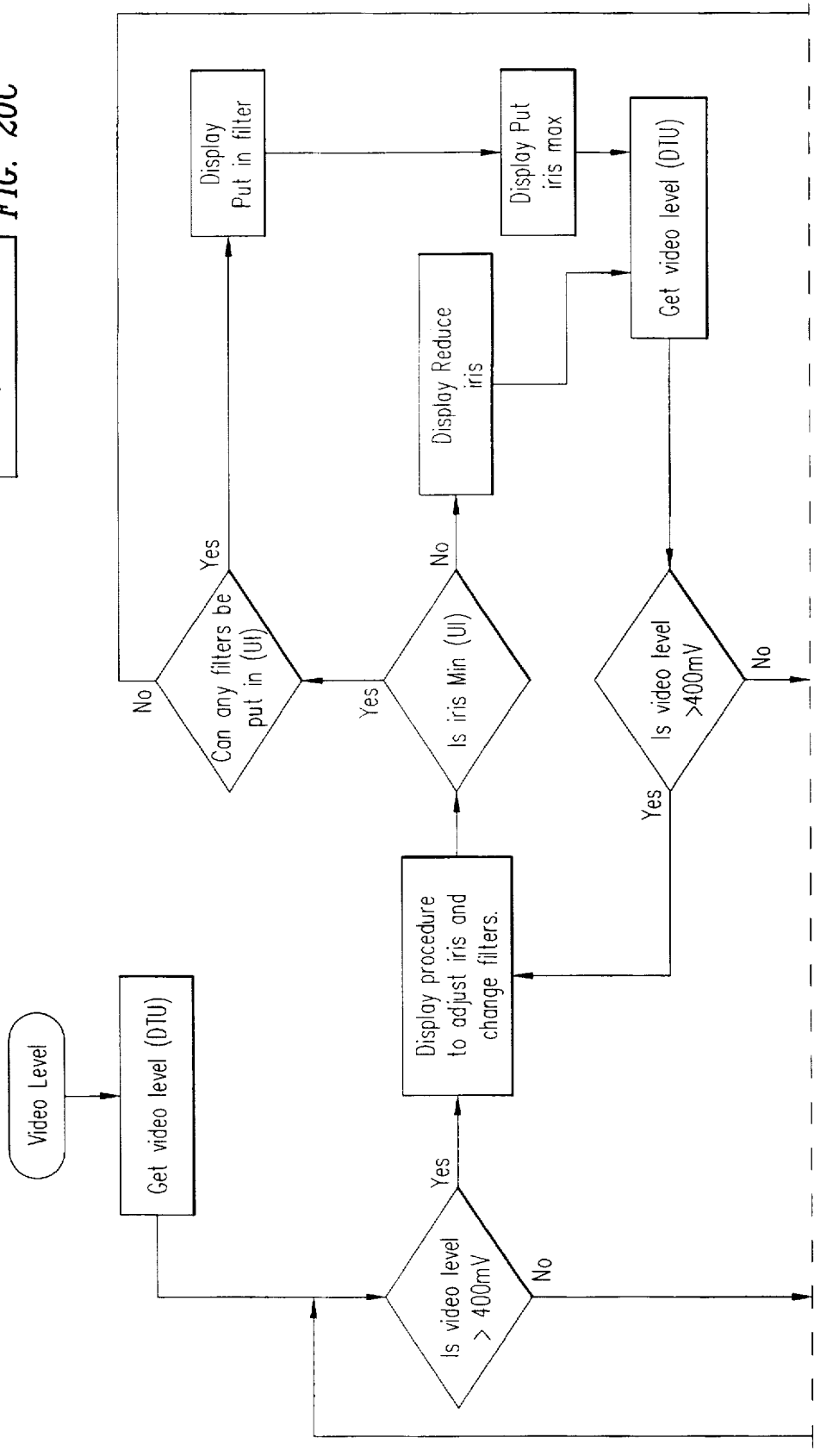
Figures 2, 20C:
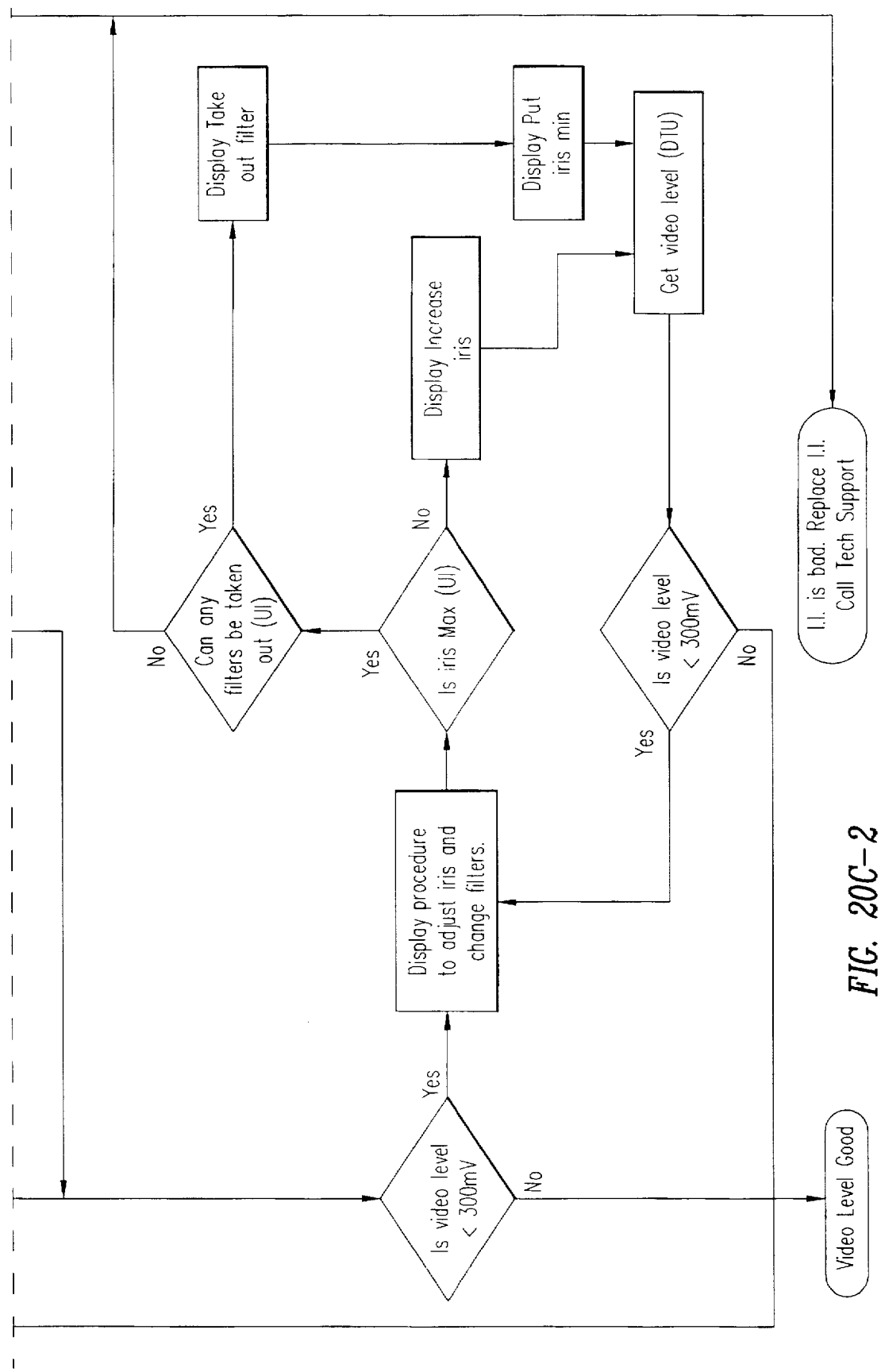

The resolution procedure performs a series of isolation techniques to determine the true cause of the problem. The procedure displays instructions on the field service engineer notebook computer. The field service engineer inserts a phantom object in the x-ray image area. The phantom object is a lead screen with wires having predetermined spacing and predetermined thicknesses. Using an algorithm written in C and C++ language, shown in FIGS. 15A and 15B, the resolution procedure determines at which point the resolution of an image can be measured (normal mode, magnified I mode, or magnified II mode). If the resolution can be measured at any of the three modes, then the image tube is good. The resolution procedure then executes other procedures such as "Display Master Objective Lens." If the master objective lens is good, then a "Check Focal Spot Size" procedure shown in FIGS. 16A and 16B is executed.

In an effort to correct the resolution problem, a field service engineer may have thought the image tube was bad, and erroneously replaced it, when in fact the filament of the x-ray tube was defective. The present invention 10 avoids such errors by anticipating the possible causes of a given problem, and automatically excluding/eliminating incorrect solutions.

Other procedures run by the expert system, such as Half Value Test, which, e.g., determines the hardness of the x-ray beam, Quick Tube Calibration Check, Check Max Entrance Exposure Rate, and Flouro Dose Data procedures, are shown in FIGS. 17, 18A, 18B, 19, 20A, 20B, and 20C, respectively.

Those skilled in the art will readily recognize that these procedures are merely examples of the many such procedures which can be stored on the system monitor 16 and executed by the expert system 115. These procedures are run on a commercially available software package, entitled NexPert, produced by Neuron Data Corp. located in Palo Alto, Calif. A sample of the source code (using NexPert's own code language) for the expert system 115 is included in microfiche form in Appendix A.

The system monitor 16 also has security functions. Remote users, e.g. the TAC 19, and users connecting to the system monitor 16 via the field service notebook 18, are authenticated via a user login and user password in conjunction with a hardware key 100 attached to the parallel port 106 on the field service notebook 18. This authentication information is kept in the system monitor database 110. A temporary hardware key is provided for installation and testing of the diagnostic system 10. Upon installation, the field service engineer makes a confirming call to the TAC 19 which, in turn, makes the key site-specific.

The expert system 115 also utilizes the performance and history information in the system monitor database 110. The system monitor database 110 stores an error log, an activity log, a problem resolution log, a results log, providing results from system evaluation tests, hardware key information, a remote connection log, a site history log, and system monitor module version information, containing version and revision information on each process and software release. Collectively, this information is used to support expert system diagnostics.

Field Service Notebook

The field service notebook 18 completes the diagnostic system 10 of the present invention. As shown in FIGS. 1–2 and 13, when the field service engineer arrives on site the field service notebook 18 is connected to the system monitor 16 with an ethernet connection 20. Then, using a graphical user interface software tool 22, the user can communicate with the system monitor 16 and access all of its diagnostic and maintenance functions, including the individual DTUs 12. The field service engineer notebook 18 includes: a microprocessor such as an "Intel 386" or "486" or equivalent portable computer; graphics capability; "Windows"; and a windows-based Graphic User interface (GUI). In the preferred embodiment of this invention, a GUI such as "SmartBook" from Toshiba America Medical Systems in Tustin, Calif. is used.

Technical Assistance Center

The Technical Assistance Center 19 ("TAC") is the central information source for the diagnostic system 10 of the present invention. See FIG. 3. Tools are available to the TAC engineers from a common user interface which allows the TAC engineers to upload and view images as well as to upload log files from the on-site system monitor 16 to review system performance. Complete site history as well as an on-line expert system is also available at the TAC 19. The technical experts at TAC 19 are available to assist the field service engineers with immediate diagnostic system questions.

The hardware for the TAC 19 includes: conventional personal computers (PCs) with internal modems, ethernet cards, 200 megabyte or more hard drives, CD-ROM drives (these can be attached to the file server to be used as a shareable resource), ethernet connections between work stations, a file server, a backup system, an uninterruptable power supply (UPS), and a laser printer. The TAC 19 preferably uses a commercially available Novell network, an Oracle Database Server, a Neuron Data Expert System, and Windows 3.1 software on all PCs. The TAC 19 workstations are connected via ethernet and operate on the Novell network.

The following functions are available to the TAC user when connecting to a site: 1) "Get Images"; 2) "Display Images"; 3) "HW Key information"; 4) "Error Log"; and 5) "Site History". All of these functions, represented by on-screen buttons or icons, are accessible from the displayed screen. Wherever possible, accelerator keys are provided for the functions. (The term "Accelerator keys" is used here to mean a keystroke or a combination of keystrokes that can be used in place of pull down menu commands or click-on buttons.)

"Get images" enables a TAC engineer to connect to a site and retrieve images. There is an option of looking at the image as an icon before retrieving it, but this icon may be somewhat less detailed than the original because of its smaller size. (The smaller image size allows faster transfer). The TAC engineer can also retrieve just the image header instead of the full image. "Display Images" enables the TAC engineer to display the images retrieved from the site. Once displayed, "windows level" controls to adjust image parameters become available. "HW Key Information" enables the TAC engineer to connect to a site and call up an on-screen snapshot of the site's key contents. "Error Log" allows the TAC engineer to browse through the site's error log. "Site History" provides site history from data stored on site, from site information stored in a TAC database 112, and, in the future, from site history stored in the ASSIST database 114.

"Site History" stored on site includes process history/ status, key update information, key status, error messages, system performance parameters, DTU records, etc. Site history from the TAC database 112 includes problems encountered, their fixes, etc. When the TAC engineer selects this option, the display area differentiates between the three sources of information either by color or by fonts. From "Site History" users may connect directly to a site to update file logs if necessary.

Through a series of database server functions the TAC database 112 maintains complete information about all sites. All of the following functions have graphing capabilities so that the user can plot displayed information on a variety of graphs (pie, line, bar). Through the database server functions, the TAC engineer can browse the "Site History" logs, browse through previous site results log from a site, see a history of hardware key updates for a site, and see when the field service engineer has upgraded a selected site and the upgrade software version installed.

Network Protocol and Communication

Figure 21:
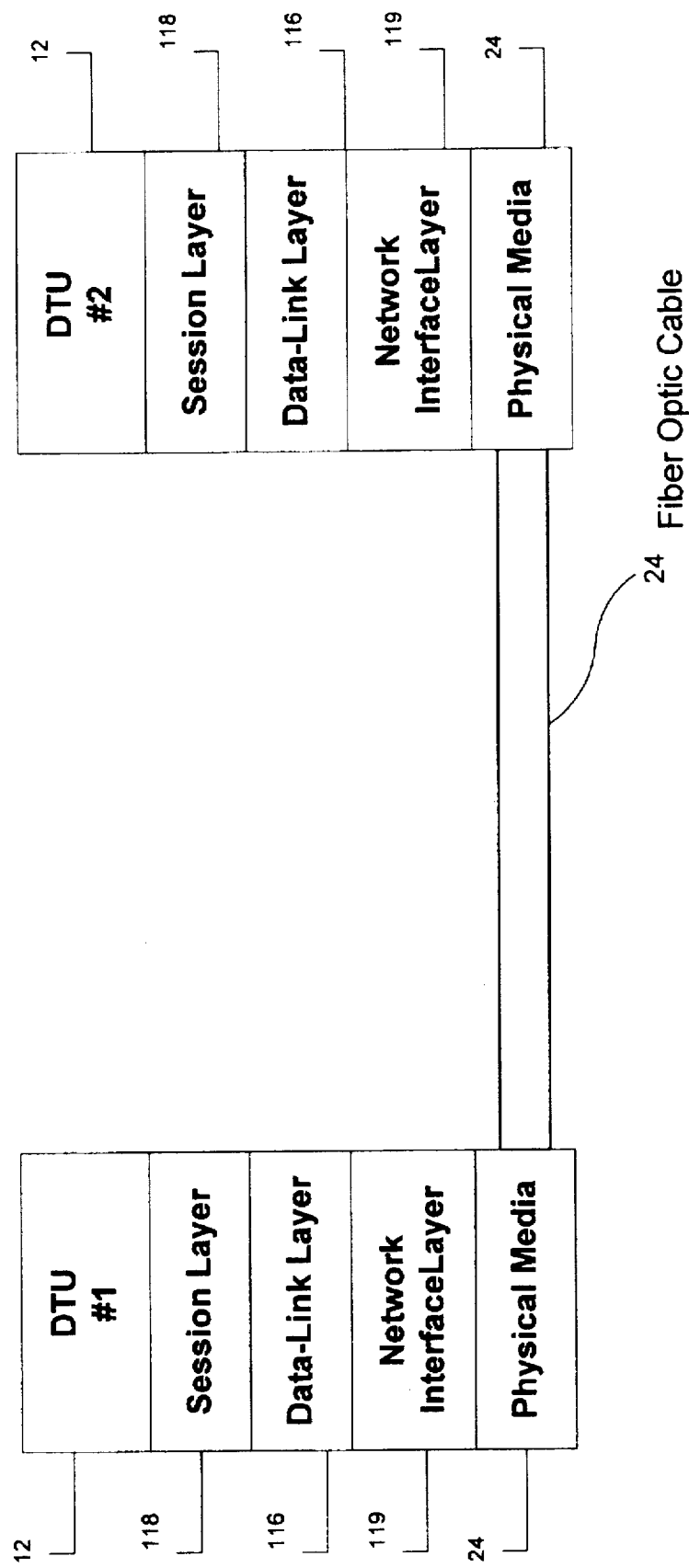
FIG. 21 is a conceptual diagram showing the session layer, data link layer, and physical media connections involved in communication between two DTUs of the present invention.

As shown in FIG. 21, the DTU 12 network protocol consists of three logical layers, a data link layer, 116, a session layer 118, and a network interface layer 119, operating over a physical media layer, the fiber optic network 24.

After power-on the RS232 port 60 of the microprocessor 44, FIG. 11, is programmed to 9600,N,8,1 data format and the optical lines 55 are connected to the RS232 RxD and TxD pins. Thus, each DTU 12 can be accessed by the fiber optic network 24 using a standard RS232 protocol. Switching between RS232 and SPI 62 interface formats can be controlled by software. Communication between the DTUs 12 is done in data packets 120 such as those illustrated in FIGS. 22–24.

Figure 22:
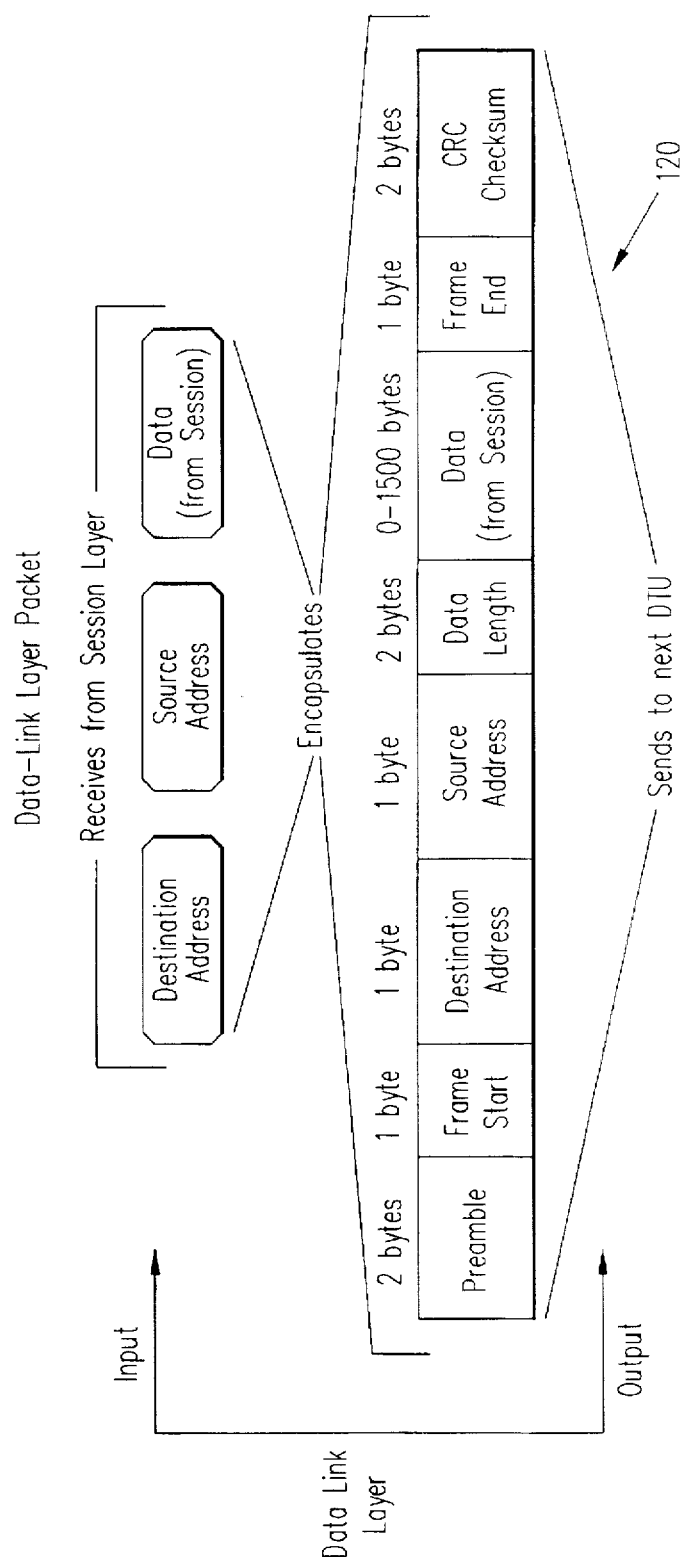
FIG. 22 is a diagram showing the components of a data link layer packet of FIG. 21.
Figure 23:
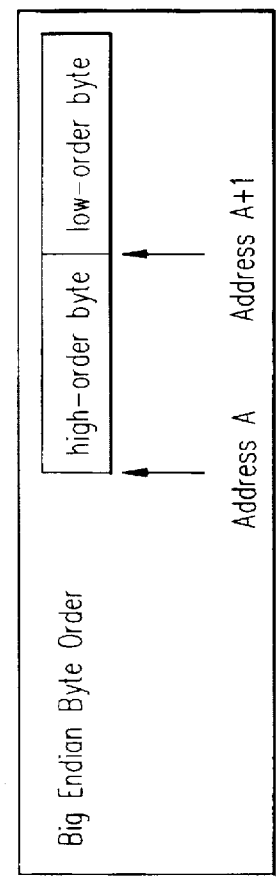
FIG. 23 is a diagram of the DTU network protocol datalink frame composition of FIG. 21.

A data packet 120 arrives at the DTU 12 to which it is addressed by way of physical media (e.g. fiber optic network 24) and is initially handled by the network interface layer 119. Thereafter the Data-Link layer 116 of the receiving DTU 12 checks the checksum, checks for the correct address, and receives the packet. Once that is completed, it sends the packet to its session layer. The data packet 120 consists of a preamble, start of frame delimiter, destination address, source address, data length field, data field, end of frame delimiter and two bytes for cyclic redundancy checksum (CRC) as illustrated in FIGS. 22 and 23. The packet length is determined by examining the data length field. Validation is then done by examining the frame start, frame end and the CRC fields. The frame start and frame end are known values. The CRC validation consists of calculating the CRC on the frame excluding the CRC fields and then comparing it with the embedded CRC. The CRC algorithm used for the data packets 120 is based on the "classical" CRC hardware circuit, conventionally known as "CRC-CCITT" polynomial (1021H). It is important to note that the CRC calculations for data packets 120 are done by software or hardware depending on the network interface selected. The CRC for the RS232 SCI 60 interface and the parallel port 40 is calculated by software, while the CRC for the SPI 62 interface is calculated by the hardware circuitry residing in the FPGA 64.

A DTU network protocol data link frame (DNP) uses the big endian as its network byte order. Thus the high-order byte is at the starting address. As an example, FIG. 23 shows the byte order used for data length and the CRC fields. It is important to note that this layer only uses the data portion of the frame to calculate the CRC.

Data Link Layer

The data link layer 116 is the lowest logical layer of the protocol. It performs the actual transfer of the data packets 120. The data link layer 116 functions by receiving and encapsulating data from the session layer 118. As illustrated in FIG. 22, encapsulation includes attaching the address and calculating and attaching the checksum to the session layer data. The data link layer 116 then sends a data packet 120 shown in FIG. 22, to the next DTU 12.

The data link layer 116 provides three different data transfer options depending on a particular application's needs. The three data transfer methods are: reliable transmissions with positive acknowledgement, transmission without acknowledgement, and reliable transmission with sliding window.

Reliable transmission is based on the fundamental technique of "positive acknowledgment with retransmission." This technique requires the recipient to communicate with the source, sending back an acknowledgement message as it receives data. The sender keeps a record of every data packet 120 it sends and waits for an acknowledgement before sending the next data packet 120. The sender also starts a user-defined timer when it sends a data packet 120 and retransmits the data packet 120 if the timer expires before an acknowledgement arrives. Up to three retransmissions will be attempted. For performance reasons, the received message is delivered to the session layer 118 which can send the acknowledgment and reply in one message thus saving half the time necessary to accomplish the work. The sender data link layer 116 always passes the acknowledgment (embedded reply) to the session layer 118 for further processing. In this mode, no buffering is used on the DTU 12 nodes. A handle to the received message is passed to the application. The length of the message can not exceed the "DNP Maximum Transfer Unit" constant. The Open Network, Close Network, Annotate, Invoke Address, invoke Name, Download, Upload and Memfill modules are implemented using the Reliable Transmission Service.

Transmission Without Acknowledgement allows applications to transmit messages without waiting for an acknowledgement. No retransmission of messages is done. The data link layer 116 provides a simple transmission service which transmits the message without waiting for an acknowledgement. It is the responsibility of the application program to confirm that the data packet 120 was received without errors at the destination.

Figure 25B:
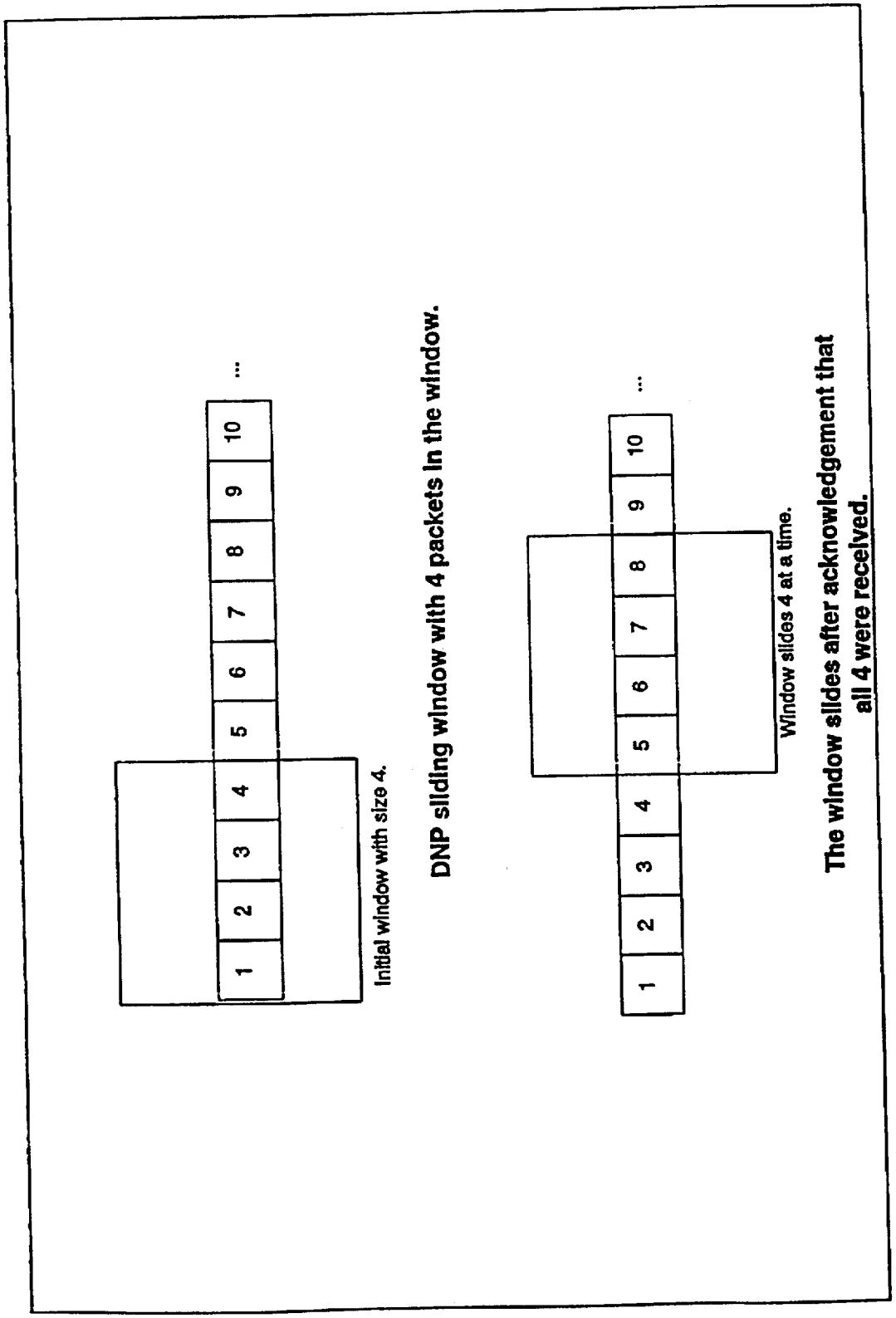

The Reliable Transmission/Sliding Window Technique is used for larger transmissions than is possible with the other transfer methods. The "sliding window" technique is a form of positive acknowledgement and retransmission in which multiple data packets 120 are transmitted before waiting for an acknowledgement. As shown in FIG. 25A, instead of acknowledging receipt of each individual data packet 120, packets 1–4 respectively, the receiver site waits until four (4) data packets 120 have been received, spools each acknowledgement and then sends one (1) acknowledgement to the sender site. The number of unacknowledged data packets 120 at any given time is constrained by the window size and is limited to a small, fixed number. Once the sender receives the acknowledgement for the first four data packets 120, as shown in FIG. 25B, the window slides four at a time and the next series of data packets 120 are sent.

Lost data packets 120 are retransmitted and acknowledged before the window slides. The sender encodes sufficient information in the data packet 120 indicating when the acknowledgement should be sent. When the sender retransmits lost data packets 120, it requests the receiver to send the acknowledgement immediately for every data packet 120.

Unlike both the Reliable Transmission with Positive Acknowledgement and Transmission without Acknowledgement methods, with the Sliding Window method, all acknowledgements are done by the data link layer 116. The sender data link layer 116 accepts a large message from the session layer 118 and the receiver's data link layer 116 delivers a large message to the receiver's session layer 118. If requests are too large, the data link layer 116 can break them up into data packets 120.

Session Layer

The Session layer 118 is the higher logical layer on the DTU network 13 protocol layer. It provides protocols for the two types of services needed in the DTU network 13: 1) DTU network 13 protocol services standard for every DTU 12; and 2) specific services which are defined by the type of DTU 12, e.g. kV, mA or dosimeter, etc.

Figure 24:
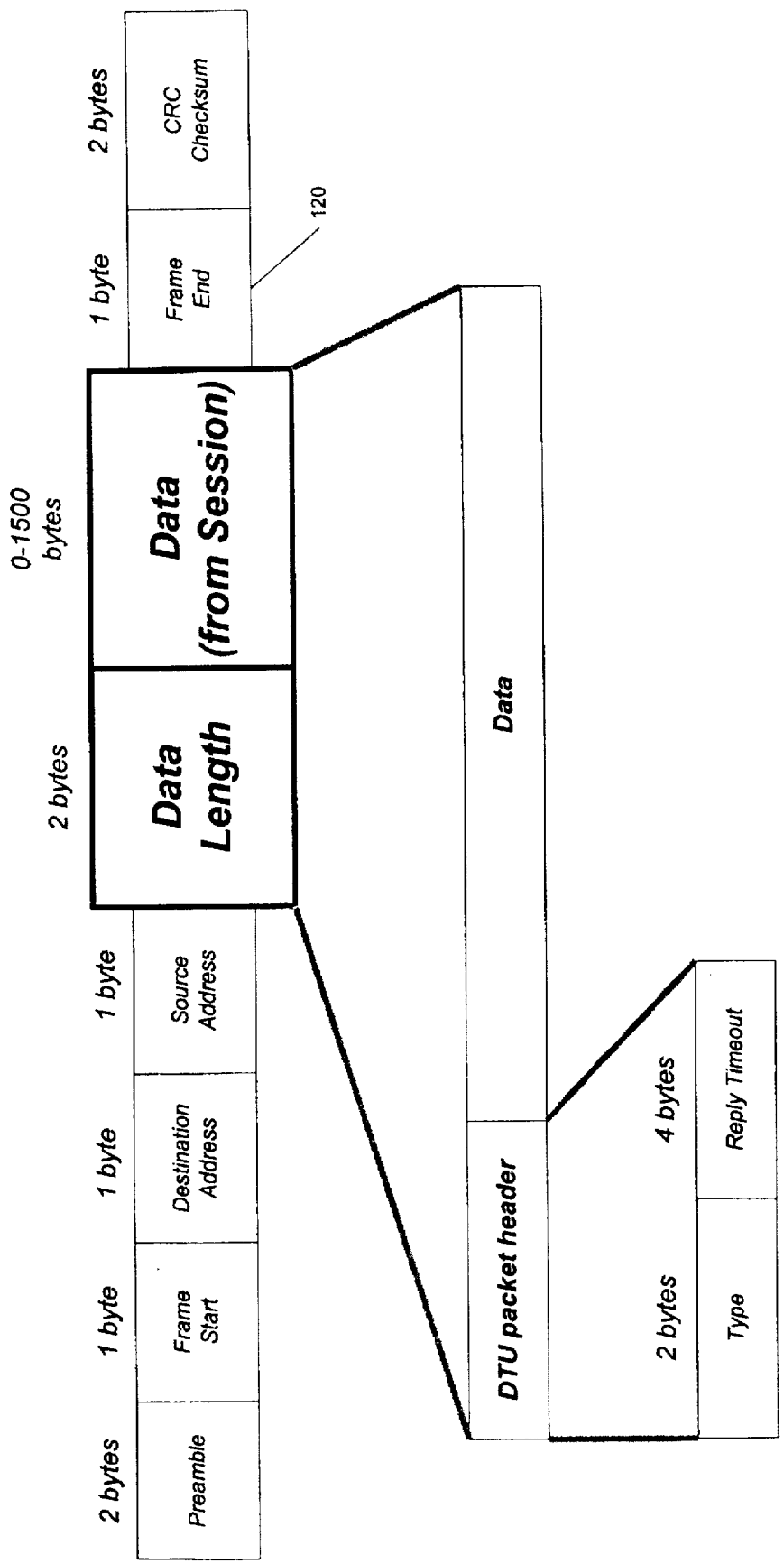
FIG. 24 is a diagram showing the composition of the session layer packet of FIG. 21.

Data that the session layer 118 sends to the data link layer 116 consists of two parts, data length and Data (which contains the header in addition to the data). The session layer 118 uses only the data portion of the data packet 120. As shown in FIG. 24, based on the first two bytes of the header, the session layer 118 is able to determine the type of service requested of or by the DTU 12. The services include annotation, network check diagnostics, programs and modules download, module invocation, memory dump, and DTU 12 time setting and debug sessions.

Network Interface Layer

The network interface layer 119, responsible for the data communication at the lowest level of the network, consists of device drivers and modules necessary to transmit and receive data packets 120. CRC calculations and validation are performed at this level such as the SCI 60 (RS232), SPI 62, parallel port interface 40, and packet drivers.

All data packets 120 with valid CRC and destined for the DNP address assigned to the local node, are accepted and passed to the data link layer 116. "Broadcast" data packets 120 are also accepted. All other data packets 120 require no further processing and are dropped. The notable exception is the master DTU 34 which accepts data packets 120 that are destined to itself as well as to the system monitor 16. Data packets 120 destined to or from the system monitor 16 are routed over the parallel port 40 interface on the system monitor 16.

DTU Software

DTU software is broadly categorized into "Start Up" software which executes when the DTU 12 is powered on, and "Services" software which executes when the system monitor 16 requests a service. Sample source code, using a combination of C and 68HC11 Assembly language, for a kV, mA DTU 38 is included in Appendix A.

After Power On/Reset the 68HC11A0 microprocessor 44 begins executing instructions (code). (See Microprocessor Memory Map, FIG. 10). This software code: selects the EPROM 58 bank that contains code for the FPGA 64 such as model No. XC3064, manufactured by XILINX, of San Jose, Calif., copies the FPGA code to the FPGA chip 64, and runs self-diagnostics. Self-diagnostics begins with a memory test on the two RAM chips, 56A and 56B, in the DTU 12. If no network-disabling faults are encountered during diagnostics, the software initializes the serial port 54 and waits in a continuous loop for any data packets 120 on its serial port 54. The software selects bank 0 from the memory 2000 chip 56A and sets up the necessary communication buffers. These buffers are used to receive data packets 120. The startup pseudocode is described in FIG. 26.

The FPGA 64 performs logical functions according to programs loaded to it after power on. Programs may be downloaded from the system monitor 16 to the RAM memory banks, 56A–56C of the microprocessor module 44. The FPGA 64 is memory mapped from address 0800 to 0FFF (hex). Port A of the 68HC11A0 microprocessor 44 is connected to various FPGA 64 control pins. The FPGA 64 is RAM configurable, the FPGA 64 configuration must be downloaded after power on. The configuration program resides in the EPROM 58. The initialization process involves resetting the FPGA 64 and then copying the configuration from EPROM 58 to address 0800 (hex).

To reset the FPGA 64 the RESET (Port A bit 6) and PROGRAM_DONE (Port A bit 5) pins of the FPGA 64 are set to "LOW" for 6 microseconds, then restored to "HIGH". The reset is successful when a LOW to HIGH edge is detected on the INIT (Port A bit 0) pin. The configuration program is downloaded by writing one byte at a time to address 0800. The FPGA 64 uses one pin to accept the data. In order to properly download the program, the READY/BUSY pin (PORT A bit 1) must be checked to make sure it is "ready" before writing the next byte to the FPGA 64.

DTU Self-diagnostics

The present invention has an error reporting mechanism to indicate any equipment or network failures. If an inconsistency occurs in the DTU 12 read/write processor the system detects an unacceptable voltage level, a signal is sent to the LED 104 on the corresponding DTU 12 to indicate a problem condition. The field service notebook 18 may also be connected directly to the RS232 terminal 55 on the DTU 12 for local diagnostics.

When FPGA 64 initialization has been completed, DTU 12 self-diagnostics are performed. First the RAM memory test is performed by writing a unique pattern to each bank of the RAM chips 56A, 56B and 56C, on the DTU 12. The pattern is read back and compared. The pattern used for the test is the bank number. Because all of the banks are written to and then read, the bank switching feature is tested simultaneously. If an inconsistency occurs in the read/write process, the startup is halted and the error is reported to the LED 104.

Next the battery voltage level and power supply level are checked. If there is an unacceptable voltage level, the startup halts and the error is reported by the LED 104. A low but acceptable one which still permits the electronics to function within spec. voltage is reported to the system monitor 16, but does not halt the startup.

The SCI interface 60 is initialized with the following setting: Baud Rate: 9600; Parity: None; Stop Bits: (1); and Data Bits: (8). Next, the network buffers are initialized. Two buffers are required to receive and send data packets 120. The buffers are allocated from BANK 0 RAM2000, 23A.

DTU Operation

Figure 27:
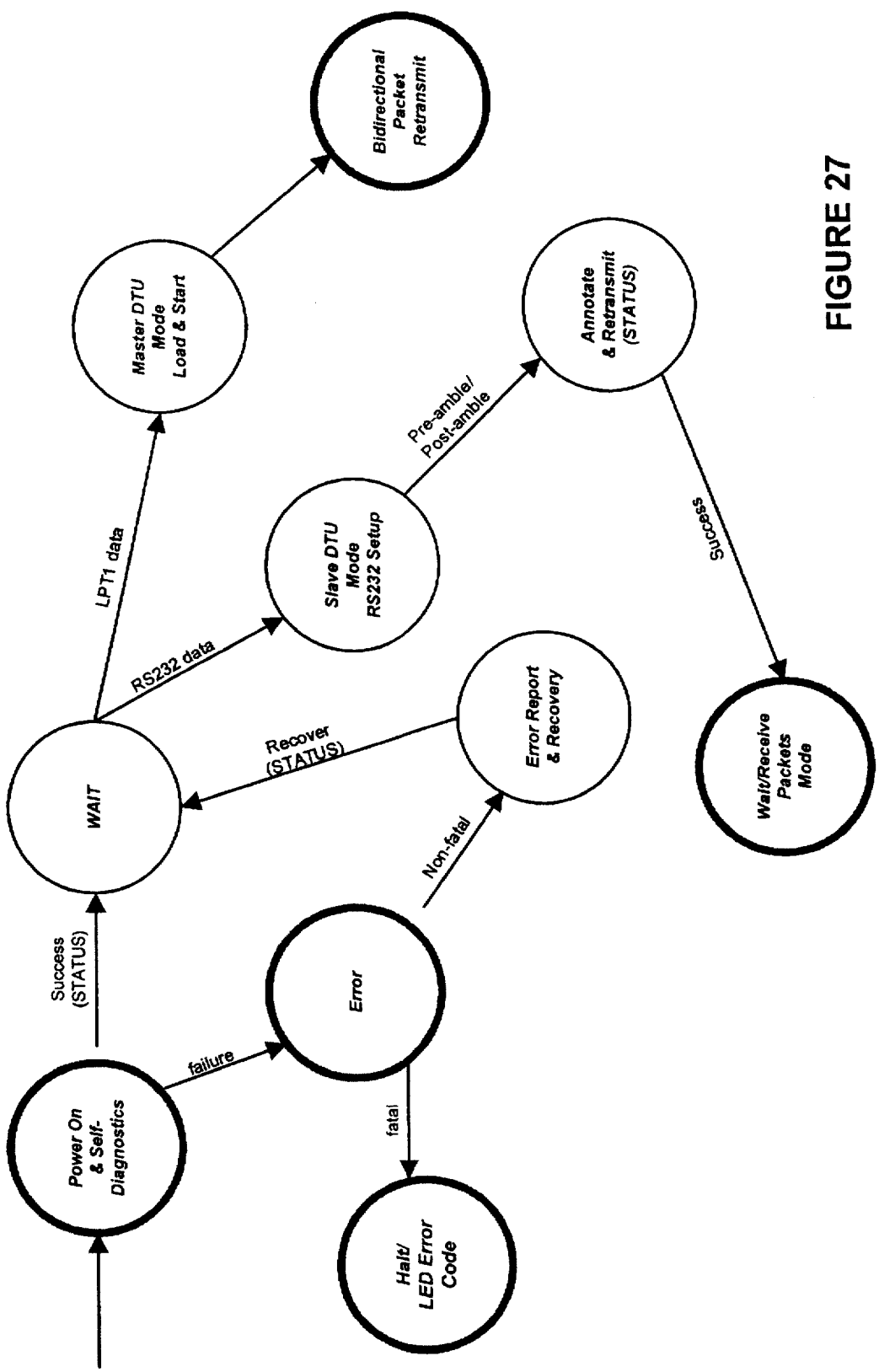
FIG. 27 is a diagram showing a generic start-up sequence for a generic DTU.

The "Start-up" sequence, shown in FIG. 27, is the process of initializing the DTUs 12. Each DTU 12 as directed by the system monitor 16 through the master DTU 34, runs self-diagnostics and annotation. A portion of the "power on" process is the annotation of the DTUs 12 in which they identify themselves as they pass a command packet 122 through the DTU network 13, returning it back to the master DTU 34.

The annotation command enables configuration of the DTU network 13. At startup all DTUs 12 determine their status and their SCM's 50 status. At annotation time, the status and identification numbers are encapsulated and sent as part of an annotation packet 124. The identification number for the DTU 12 and the SCM 50 is assigned at EPROM 58 programming time and is kept in the EPROM 58. Both numbers are available for the software to read at startup time. A sequence number for the DTU 12 is also added to the annotation packet 124.

Figure 28:
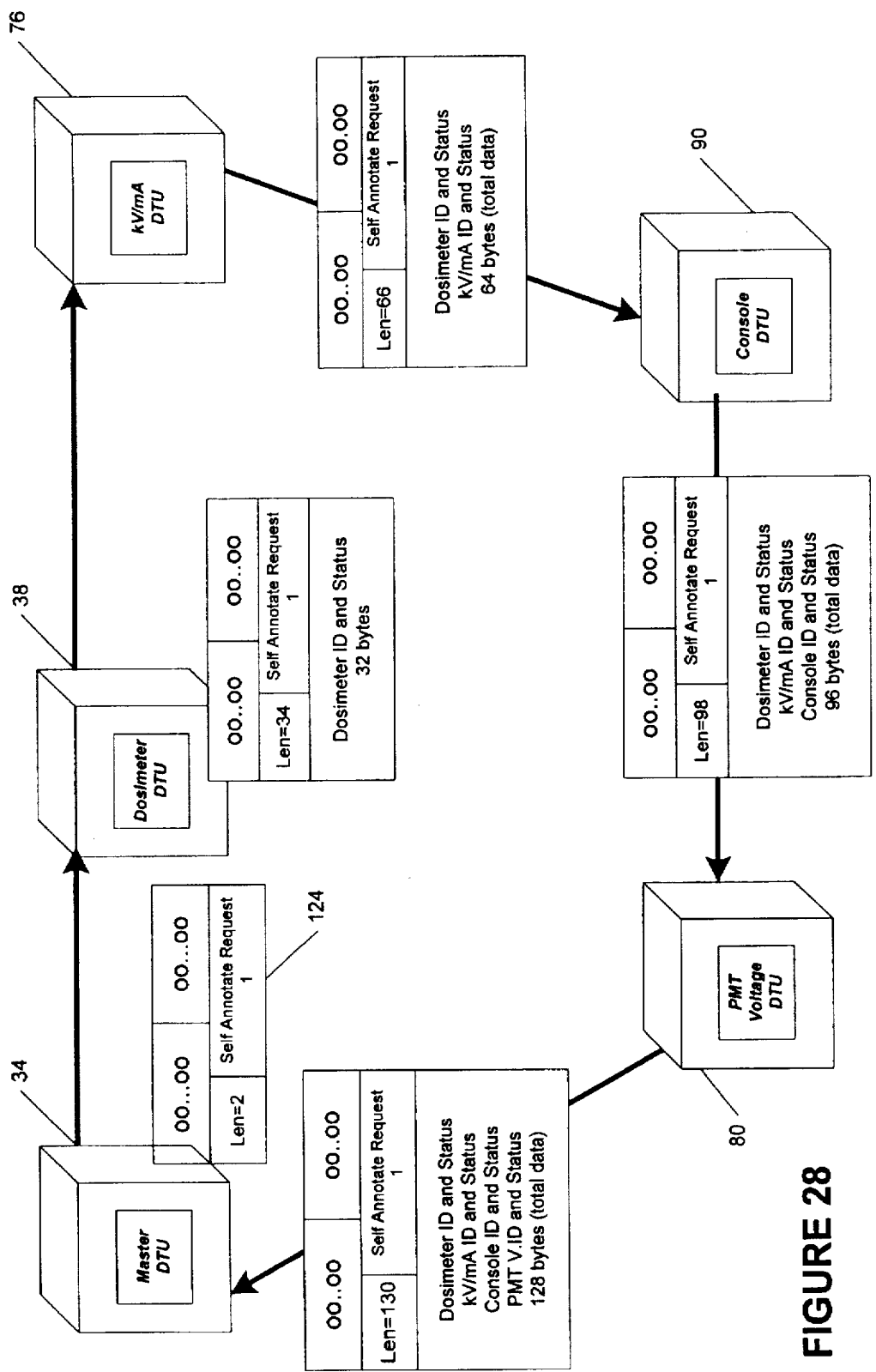
FIG. 28 is a diagram showing a DTU network annotation session in accordance with the present invention.

As shown in FIG. 28, the annotation packet 124 travels from the master DTU 34, through the DTU network 13, while the annotation information from each of the DTUs 12 is added to the annotation packet 124. Also, when the DTU 12 examines the annotation packet 124, it determines its sequence number in the DTU 12 network and binds that sequence number as its network number.

The annotation session assumes that the fiber optic network 24 is in the open configuration and that the DTUs 12 understand that the annotation packet 124 must be retransmitted after they add their annotation information. A DTU Memory Dump command provides the capability of requesting a memory dump of the DTU 12 memory. The system monitor 16 initiates a memory dump request to the DTU 12 indicating the bank, starting address and the total number of bytes to dump. The DTU 12 then replies with an image of the memory. A sample of the EPROM 58 boot-up source code, using a combination of C and 68HC11 Assembly, is included in Appendix A.

The system monitor 16 can download additional modules to the DTU 12. A download command provides the capability of downloading a program module to any bank of the RAM chips on the DTU 12. The bank, starting address and the number of bytes are specified. A module-invoke command is the way the system monitor 16 instructs a DTU 12 to execute a module that was downloaded to RAM memory. This command sets the DTU 12 time to the system monitor 16 time in seconds since 1970.

Each DTU 12 performs and provides specific services based on the SCM 50 it contains. The general network services (such as check, open, close, annotation, DTU memory dump, download, module invoke and set-time commands) are provided by all DTUs 12 regardless of their specific purpose. These general services are accomplished through DTU 12 network commands. The maximum number of DTUs 12 in the network is 255; however, twelve is the preferable arrangement.

A network-check is initiated by the system monitor 16 (via the master DTU 34). Since the fiber optic network 24 is normally closed (retransmit enabled) any data packet 120 sent from the master DTU 34 should be received back by the master DTU 34. The type of data packet 120 is set to indicate that this is a "pass through" data packet requiring no processing or replies. If the data packet 120 transmitted is received back by the master DTU 34, the fiber optic network 24 is operational.

A network open command instructs all the DTUs 12 to disable their auto retransmit feature. Thus, the DTU 12 retransmits any data packet 120 that is not addressed to it. The annotation packet 124 is an exception, as described above. The network close command instructs all the DTUs 12 to enable the auto retransmit feature.

Depending on the service requested from a specific DTU 12 the system monitor 16 dynamically downloads the appropriate software module to the DTU 12 after annotation of the network to set the DTU 12 function. Thus, each DTU 12 connected to a different piece of equipment has a specific software package, executive module, tailored for its function.

For example, the executive module in the kV, mA DTU 76 waits for a request from the system monitor 16 to sample either kV or mA. Once the request is received the analog port (Pin 0 for kV and Pin 1 for mA) is sampled and the values are returned in the reply data packet 120. Similarly, the executive module in the PMT DTU 80 waits for a request from the system monitor 16 to sample the PMT voltage. Once the request is received the analog port (Pin 0) is sampled and the value is returned in the reply data packet 120.

The master DTU 34 software module has a parallel port 40A through which the master DTU 34 communicates with the system monitor 16. The master DTU 34 waits for the strobe signal from the system monitor 16 received through the system monitor LPT port 40 and then reads eight bits (1 BYTE). Once the bytes read make up a frame, the frame is routed to the fiber optic network 24. The reverse is similar except that half a byte is transferred at a time.

System Operation

The user interface between the field service notebook 18 and the system monitor 16 is accomplished by the GUI 22, preferably the Toshiba in-house software program Smart-Book from Toshiba America Medical Systems, Inc. in Tustin, Calif. SmartBook is developed on a commercially available software package known as Multi Media Toolbook ("Toolbook") produced by Asymetrix in Belvue, Wash. A sample of the SmartBook source code, in Toolbook's own language, is included in Appendix A. SmartBook allows the field service engineer access from his field service notebook 18 to the diagnostic system 10 of the present invention once his authorization has been checked. Through pull-down menu options available through SmartBook, samples of which are shown in FIGS. 29A–29E, the field service engineer has access to a variety of options.

Figure 30B:
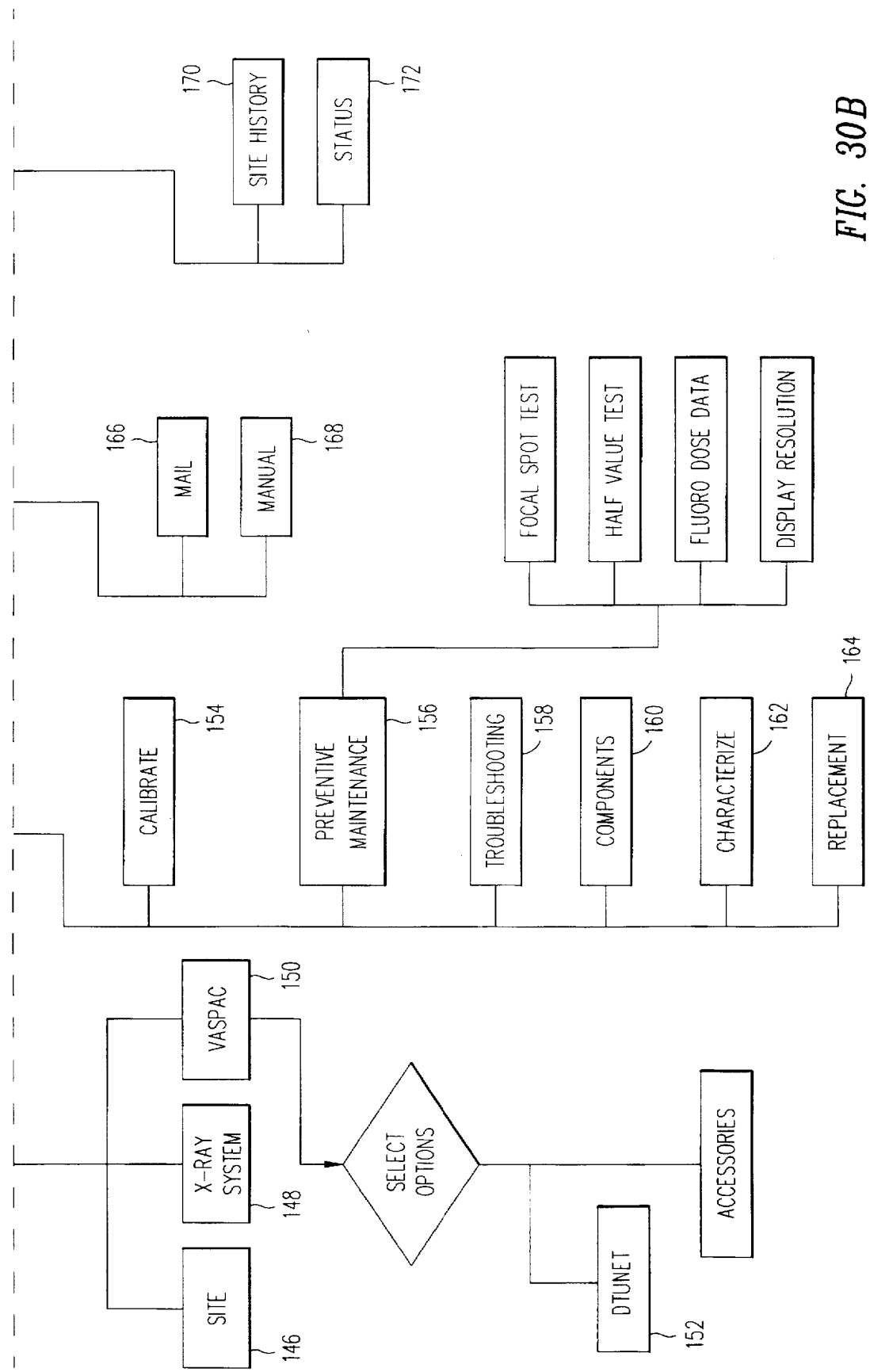
FIG. 30 is a flow chart diagram showing the menu options available to the field service engineer in the system of the present invention.
Figure 31:
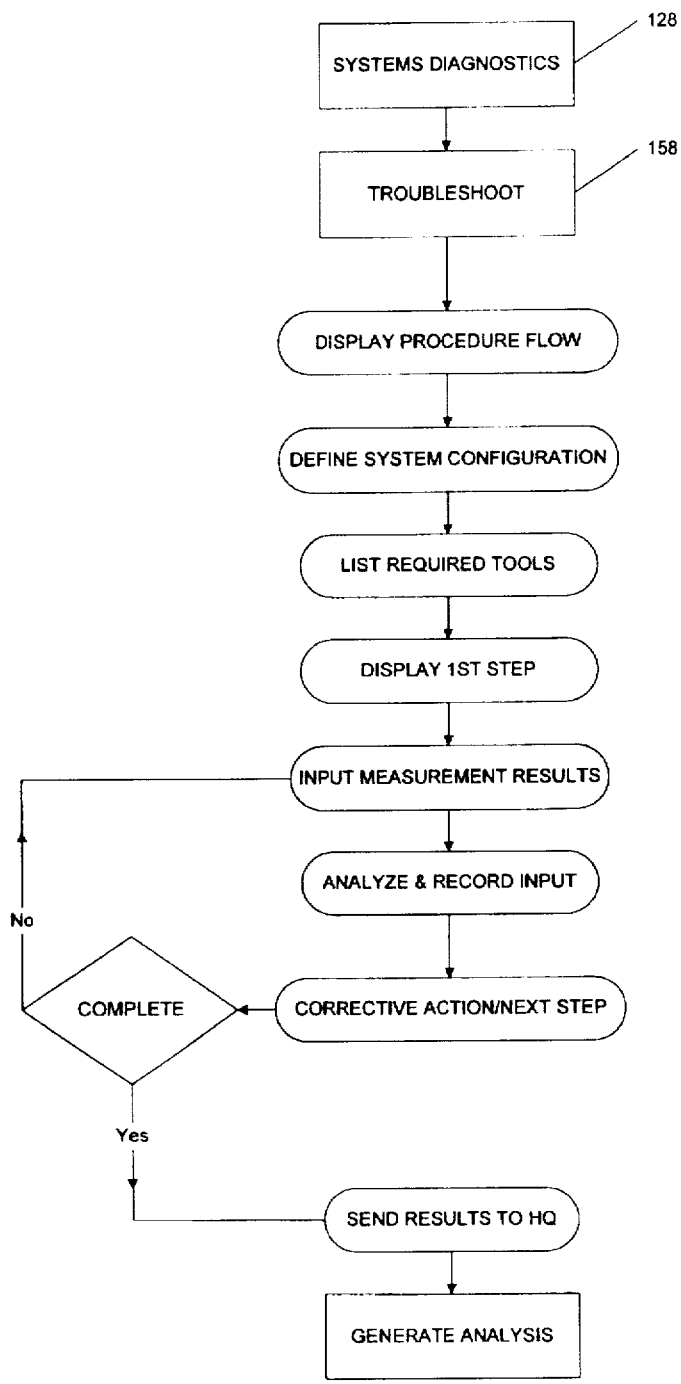
FIG. 31 is an operational sequence diagram of the "Troubleshoot" process of FIG. 30.
Figure 32A:
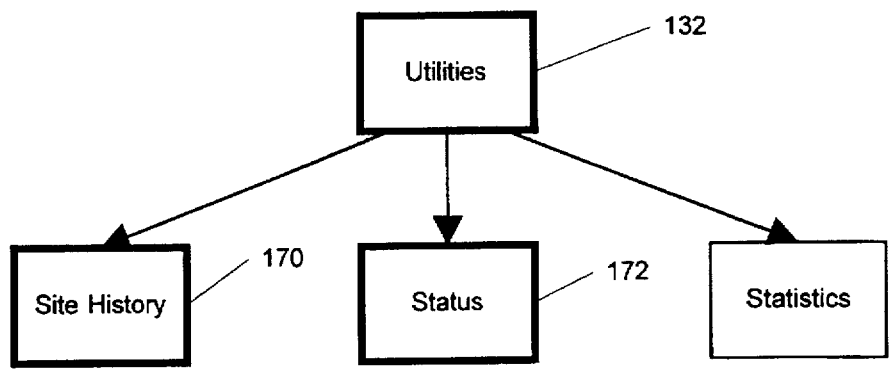
FIGS. 32A, 32B and 32C are flow diagrams for the "Utilities" option of the diagnostic software of the present invention of FIG. 30.
Figure 32B:
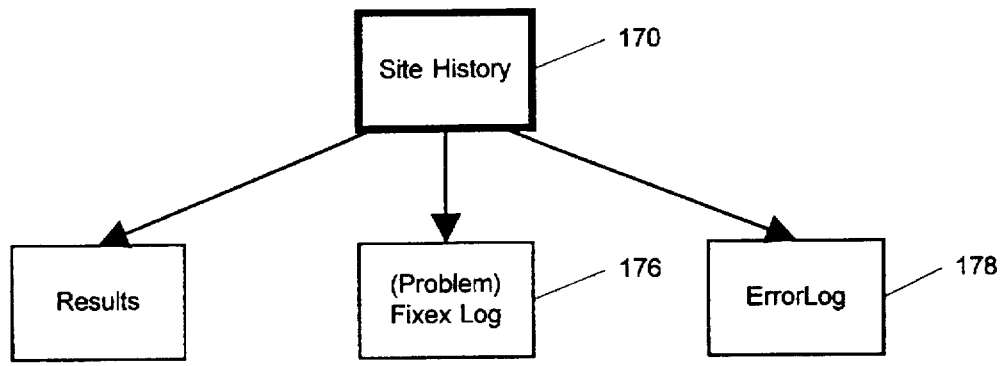
Figure 32C:
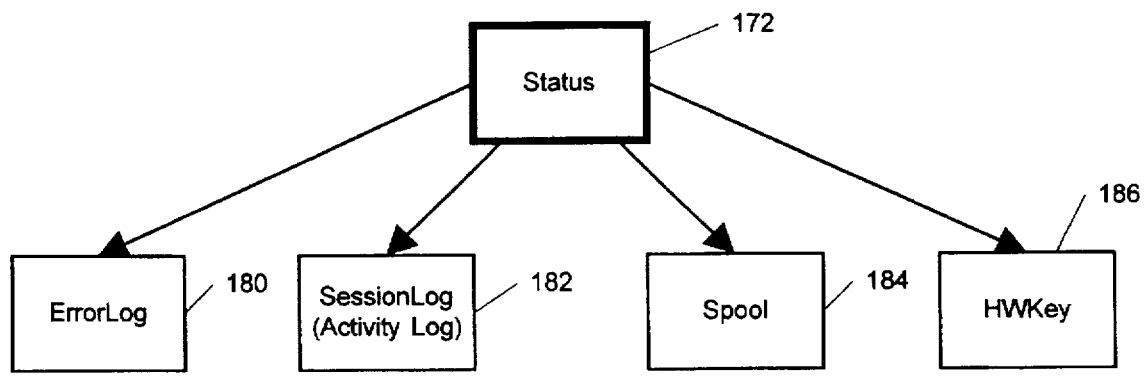

The field service engineer can immediately connect the field service notebook 18 to the system monitor 16 and, using SmartBook software, gather data and operate the expert system 115 residing on the system monitor 16 through the serial port 108. FIG. 30 illustrates the sign on sequence, and the options thereafter available to the field service engineer. First the ethernet link is established between the field service notebook 18 and the system monitor 16, step 140.

To bring up the SmartBook tool the field service engineer plugs in a customized hardware key 100 to the parallel port 106 of his notebook, step 142. This hardware key 100 authorizes the user access to the diagnostic system 10, and has an expiration time built into it. If the key has not expired SmartBook brings up a login screen (not shown) with prompts for a user name and a password.

Figure 29A:
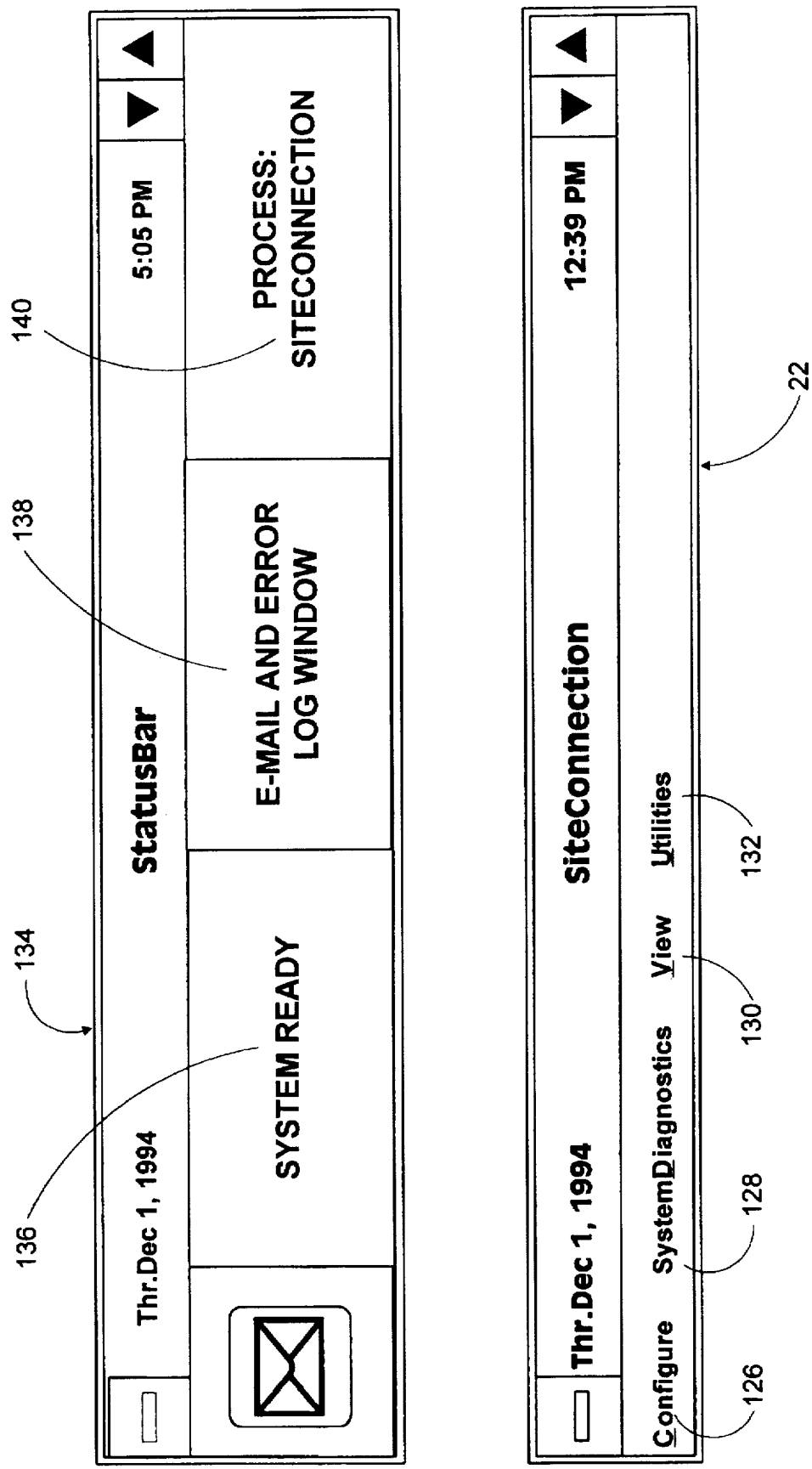
FIGS. 29A, 29B, 29C, 29D, 29E are sample screens from SmartBook, the graphical user interface software presented to the field engineer upon logging onto the system.
Figure 29B:
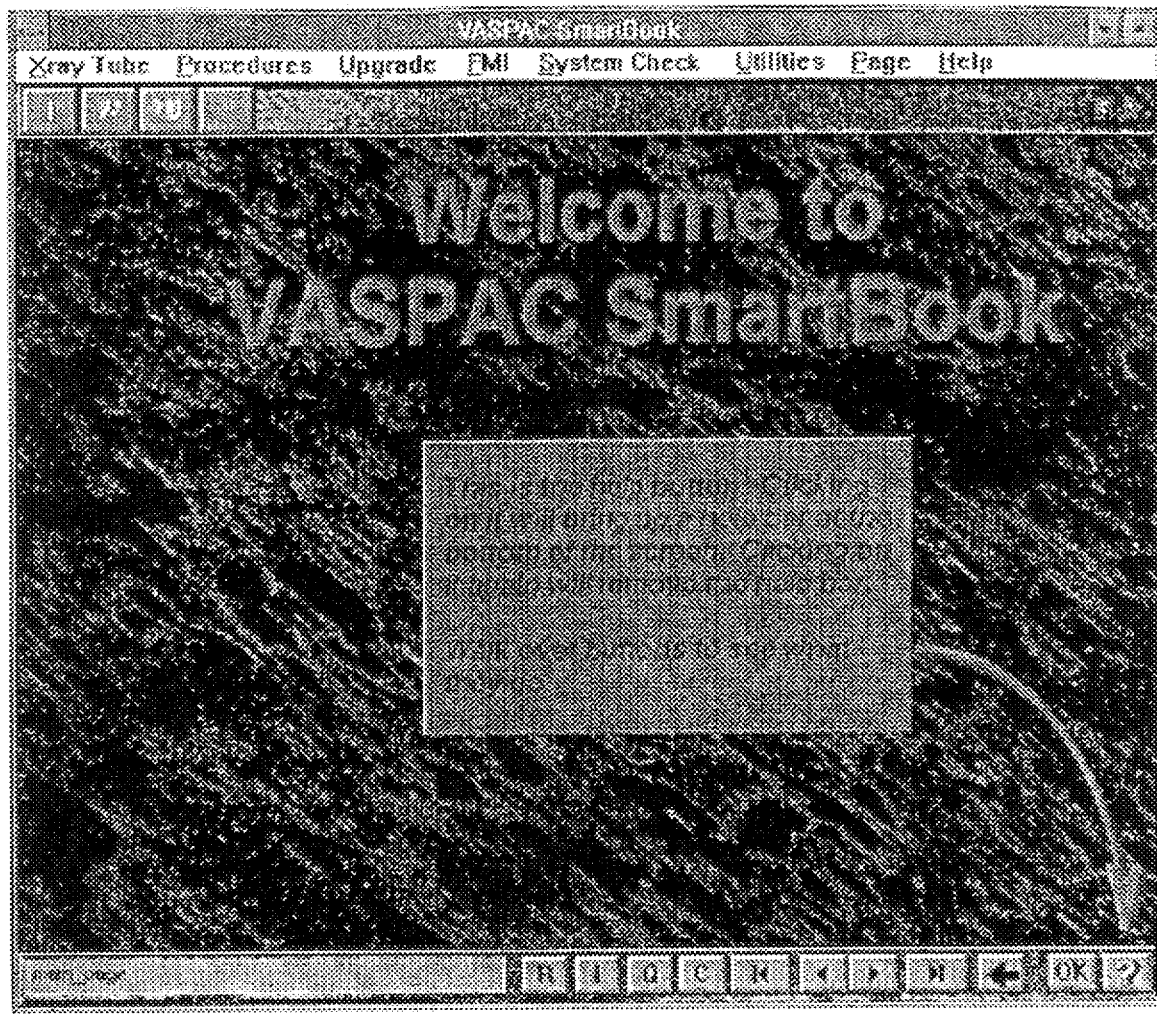

Once connected, and security access validated, the field service engineer signs on to the diagnostic system 10 of the present invention which resides in the system monitor 16, step 144. FIG. 29A illustrates a typical screen image initially presented to the field engineer, including a graphical user interface main menu 22 and a status bar 134. The main menu 22, presents several menu options on a menu bar including: Configure 126; System Diagnostics 128; View 130; and Utilities 132.

A Status Bar 134 (FIG. 29A) above each screen displays whether the site has received any new mail since the last time the user logged in, a system status area 136 showing the current status of the vascular system, a Warning or Emergency Error area 138 that shows messages requiring user attention, and a Process area 140 displaying the process that is currently running. Once the user is logged in, the Status Bar 134 is displayed with all subsequent screens. This provides the user access to key information irrespective of activity. It also provides consistency between screens and eases the process of user familiarization.

The various other options of the main menu 22 will now be described in greater detail. Referring to FIG. 30, the configure option 126 allows the user to do the initial configuration and then any re-configuration necessary at a later stage. During installation the user must configure the Site 146, the X-ray system 148, and the DTU network 13, step 150. After installation only the DTU network 13 may require re-configuration, see step 152. This is necessary each time a DTU 12 is moved to a different test point.

For "Site Configurations" step 146, the user enters site specific information that is stored both in the system monitor database 110 and the TAC 19. The X-ray configuration option, step 148, allows the user to enter information about any system component that needs to be replaced. Selecting the X-ray configuration option causes a still picture of the X-ray room to be presented on the field service notebook screen, showing the various components making up the vascular system 14. A tool bar display of various x-ray system components is also available. With this display, the user is able to select the specific components that make up the vascular system 14 on this site. Those selections are positioned in pre-determined places on the display screen of the file service notebook 18 forming a system configuration unique to this site. This specific configuration can be saved in the system monitor database 110.

Replaceable components have "hot" areas so that when selected (clicked on) the picture, the current part number, model number and serial number of the component are displayed. If that particular component is not in the system monitor database 110 the serial number field is blank and the user is prompted to type in the serial number of the new component being installed. A bar code reader 102, FIG. 13, to scan serial numbers and further reduce the possibility of error may also be used. Once the serial number is entered, the serial number, model number and part number are automatically cross-checked to ensure that the combination exists in the TAC database 112. Any discrepancy is communicated to the field service engineer via a TAC-initiated e-mail message to the site and displayed in area 138 of the Status Bar. Henceforth, whenever the field service engineer logs in to this site, notification of any mismatches is provided through the Status Bar "working and e-mail" area 138. The component part descriptions and their associated model/ serial numbers are automatically updated in the system monitor database 110 and the TAC database 112.

Selecting the "VASPAC Configuration" option from the Configure 126 menu bar, brings up another sub-menu (See FIG. 30). This menu lists the most common post-installation configurations for the specific site and offers a menu of accessory tools. A Configuration screen is presented on the field service notebook which shows both a picture of the x-ray room with test points marked and a tool bar on which various types of DTUs 12 are shown. The user can then drag and drop DTUs 12 to the various test points on the picture corresponding to the placement of DTUs on the system. If a non-compatible DTU is dragged to a test point, the mismatch is flagged as an error and the match disallowed. For example, a kV, mA DTU 76 cannot be used in place of a Dosimeter DTU 38. The user has the capability to customize, add and delete DTUs 12 from this tool bar to allow the software configuration to conform to the actual physical configuration of the vascular system 14.

The multimedia accessories connected to the diagnostic system through the Accessories selection allows the user to notify the system of available hardware such as a camera; sound board, or video connected to the vascular system 14. Functions which depend on hardware that has not been identified as "available" are turned off. Hardware that is crucial to the operation of the vascular system is not selectable. In other words, if the vascular system won't operate without it, the function cannot be turned off.

The "Systems Diagnostics" option 128 on the main menu (shown in FIG. 30) provides the user with the most common troubleshooting tools associated with an vascular system 14. The "System Diagnostics" option 128 allows the field service engineer to calibrate; do preventive maintenance; troubleshoot; view a system-specific component list; replace a part on the system; or develop "optimum" characteristics standards to allow the diagnostic system 10 to be returned to settings that the customer feels provide the best image. Through the "System Diagnostics" option 128, procedures such as those shown in FIGS. 14 and 16–20 may be executed. Sample menu screens from SmartBook showing access to representative procedures, such as "Resolution" and "Half Value Layer" are shown in FIGS. 29D and 29E.

Figure 29C:
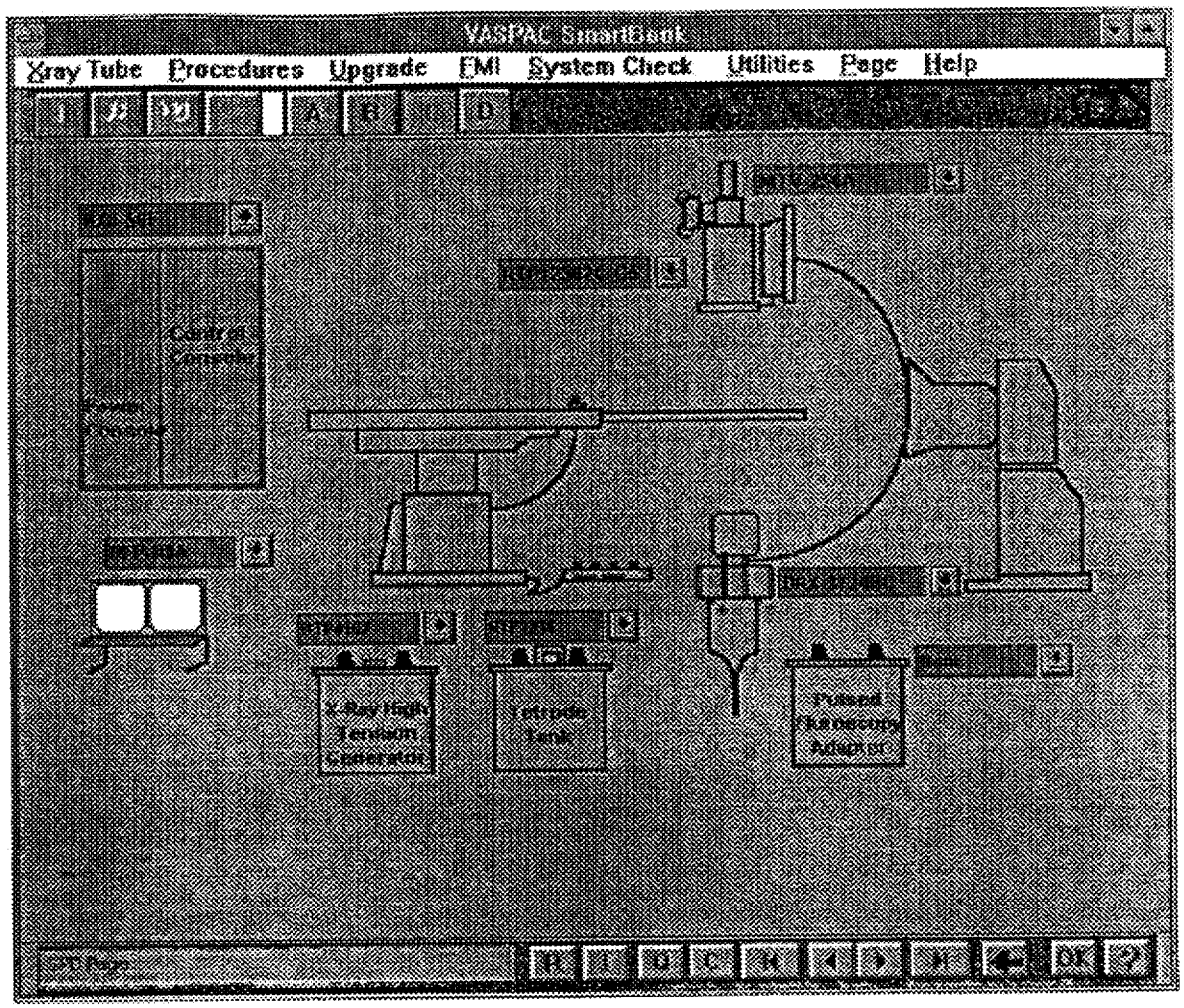
Figure 29D:
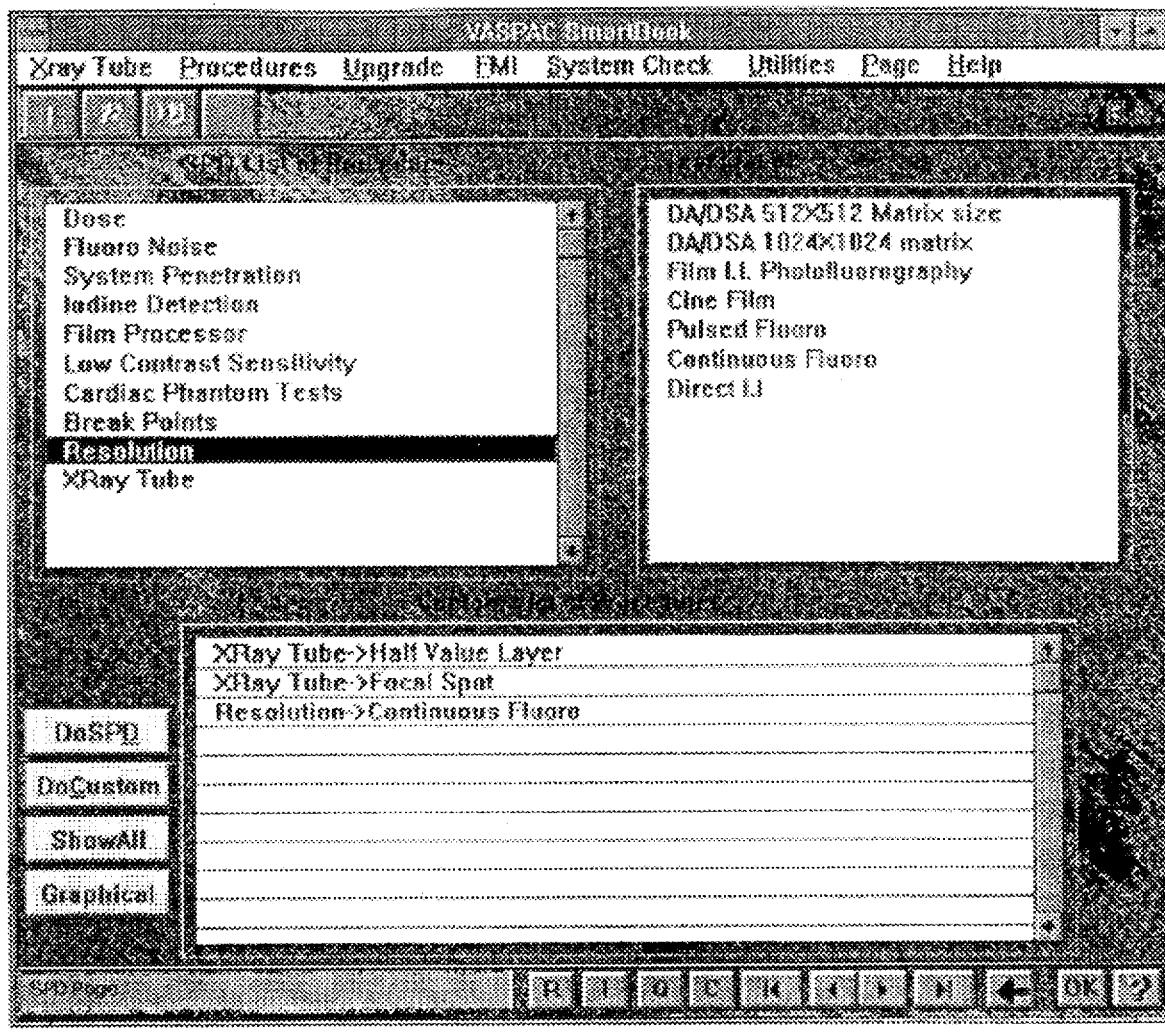
Figure 29E:
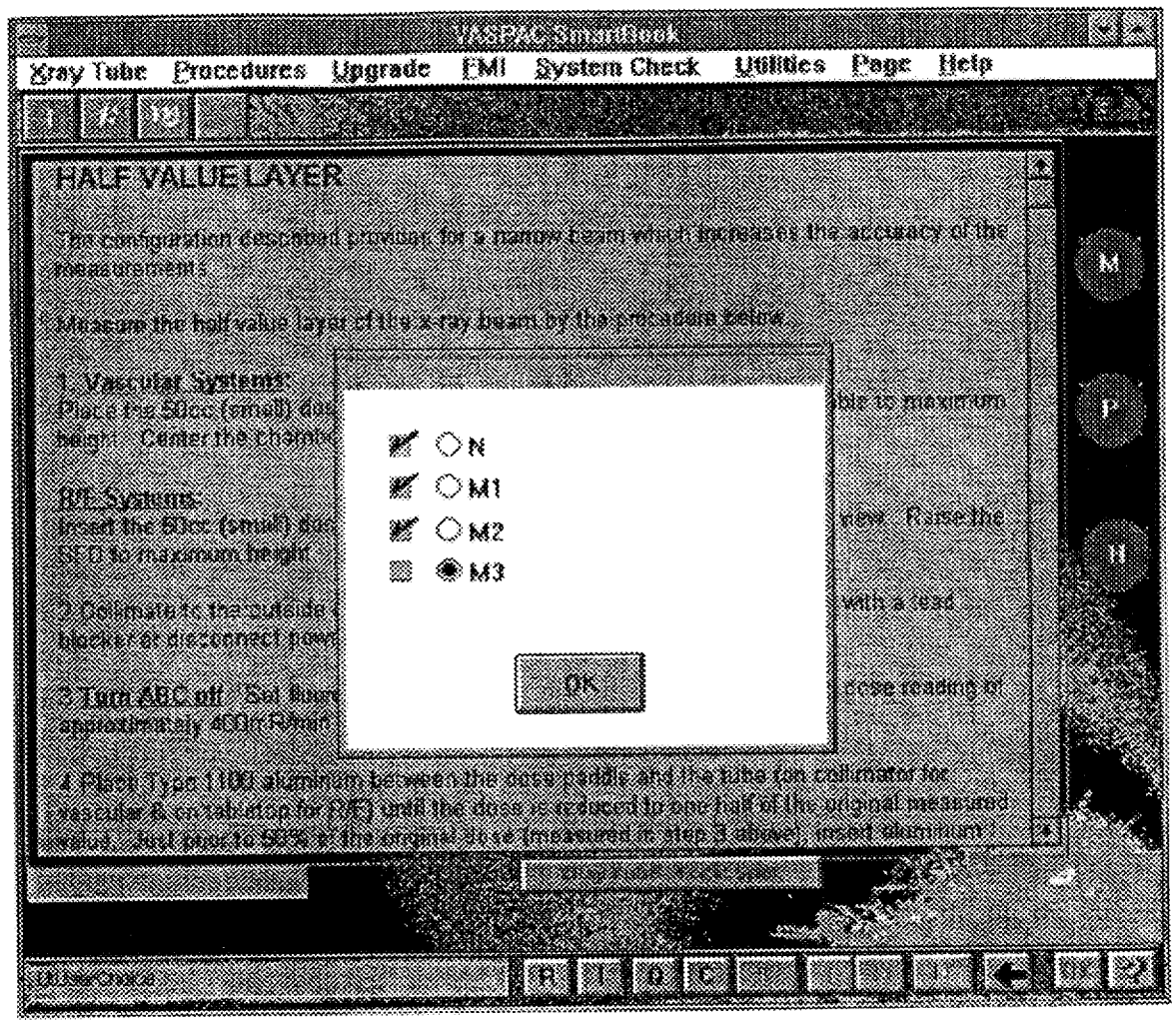

When the user selects "System Diagnostics," 128 a picture of the Vascular system 14 is displayed on the screen of the field service notebook 18, such as is shown in FIG. 29C. All selectable components of that Vascular system 14 are identified as buttons, and action buttons are placed underneath the Status Bar 134 for Calibrate 194, Preventive Maintenance 156, Trouble Shooting 158, Components 160, SnapShot 162, and Replacement 164. Thus, if the user wants to calibrate an X-ray tube the X-ray tube button and the calibrate button are selected. On-screen instructions consisting of text, flowcharts, and/or video clips to assist the user in completing the calibration process are then presented on the screen.

If, for example, the field service engineer selects "troubleshoot" the diagnostic system 10 of the present invention guides him through the evaluation process, providing on-line displays, information and suggestions as shown generically 31 (see also FIGS. 14, and 16–20).

The "View" 130 option (FIG. 30) allows the field service engineer to access either "Mail" 166 or the on-line X-ray "Manuals" 168. Selecting "Mail" 166 allows the field service engineer to view and respond to new and saved messages to the site, or view TAC 19 documentation updates. Selecting the "Manuals" 168 option allows the field service engineer access to X-ray technical manuals stored in the CD-ROM storage 94. These on-screen manuals contain text, flow charts, and both still and animated video clip illustrations. The field service engineer can browse through the technical data, view relevant video clips and even zoom in on a component seen in a still picture to get a list of sub-components, and be guided step-by-step through the repair or maintenance process. The text, still and video segments of the screen, are inter-related.

Through the "Utilities" 132 option shown in FIGS. 30 and 32A, 32B and 32C, the field service engineer can look at Site History 170 which enables viewing of past and current site results, past system problems and how they were fixed, and an Error Log 178. An analysis log of past results is stored in the system monitor database 110 in a configurable Results Log, with any overflow automatically sent to the TAC database 112. This information allows faster repair time if the field service engineer can refer to fixes for a similar problem which has occurred previously. The current system status such as errors logged, current activities, and any files that were spooled to be sent to the TAC 19 may also be viewed.

The Fixes Log 176 contains a history of all problems that have been encountered at the site and how the problems were fixed. The entire log is stored in the system monitor database 110, with a copy of the log also being stored in the TAC database 112. Updates to the on-site database are automatically sent electronically to the TAC database 112.

The Error Log 178 contains a list of errors in the vascular system 14 that have been logged at this site. The error log size is configurable, and error log overflows are sent automatically to the TAC database 112. The user is able to display errors: within a certain Range of time, of a certain level, with a certain number/string, and logged by a specific process. The user is also able to turn certain fields OFF while displaying all or a subset of the Error Log 178. For example; once all the errors associated with a certain level have been extracted, that field can be turned off to allow more information per line to be displayed. An error can be one of three levels Operator, Service and Debugging. The level displayed corresponds to the user. For instance, when a field service engineer displays the error log 178, all errors at the Operator and Service levels but not the Debugging level are displayed. When a super user is logged in, errors at ALL levels are displayed.

Via the "Status" utility 172, the user can view the current status of the diagnostic system 10 including errors logged 180 by the current session, a log 182 of activities that happened in the current session, any files that were spooled (queued) 184 to be sent to the TAC 19, and the status 186 of the Hardware Key 100. The Status Error Log 180 has the same Operator, Service, and Debugging viewing capabilities as the Error Site History log 178. The Activity Log 182 has a "Date" and "Time" stamp, logging process name, and a message string. The user is able to search through the log and extract activities logged by a specific process. The Activity log 182 size is configurable. Overflows are automatically sent to the TAC database 112. Selecting the spool 184 displays files that have been queued to be sent to the TAC database 112. Information displayed with each entry includes: name of the process that put the file in the queue, date and time the entry was spooled, date and time entry is to be sent, destination (where the file is being sent to), predicted transfer time, current status of the entry (Active or Pending), and size of the file. The user is able to edit the spool (queue) by Adding and/or Deleting entries. Added entries have a user configurable "Send immediately" option or a "Schedule to be sent at <time>" option. Default schedules the added entry at the end of the current list.

The field service engineer, through SmartBook, also has options to run various self-diagnostic tests to check the following key functions: the ethernet connection 20 between the field service notebook 18 and system monitor 16, the system monitor 16 and master DTU 34 connection, the fiber optic network 24, and system monitor 16 self-diagnostics. Therefore, one tool provides multiple service and repair functions.

Thus, through the elements described and arranged as shown herein, the present invention provides for simpler, more cost effective, and more reliable repair and analysis of a vascular system.

The terms and expressions which have been employed herein are used as terms of description and not of limitation, and there is no intention in the use of such terms and expressions of excluding equivalence of the features shown and described, or portions thereof, it being recognized that various modifications are possible within the scope of the invention claimed.

What is claimed is:

1. An apparatus for communicating with a plurality of devices, each device containing one or more electrical components, the apparatus comprising
   a plurality of distributed test units each communicating with the one or more electrical components of an associated one of the plurality of devices;
   a master distributed test unit;
   a network which permits communication of information among the master distributed test unit and plurality of distributed test units; and
   a system monitor unit communicating with the plurality of distributed test units by way of the master distributed test unit, the system monitor unit including
   a control unit which gathers information from the plurality of distributed test units;
   a data base compiled from the information gathered from the plurality of distributed test units; and
   a diagnostic unit which analyzes the gathered information and identifies conditions in one or more of the plurality of devices which may require servicing.

2. The apparatus of claim 1 wherein the network comprises an optical network interconnecting the plurality of distributed test units.

3. The apparatus of claim 1 wherein the network comprises an optical network in which the plurality of distributed test units are connected in series in a loop.

4. The apparatus of claim 1 wherein a sequence of communication of information on the network originates and ends with the master distributed test unit.

5. The apparatus of claim 1 further including a user interface unit which communicates with the system monitor unit and permits the user to communicate with each of the plurality of distributed test units.

6. The apparatus of claim 4 wherein each of the plurality of distributed test units includes means for receiving information from an upstream distributed test unit, and for relaying selected portions of the received information onto a downstream distributed test unit along with information originating with the distributed test unit.

7. The apparatus of claim 1 wherein the plurality of devices include test points and further wherein each of the plurality of distributed test units includes means for monitoring the test point.

8. The apparatus of claim 1 wherein the information communicated to a distributed test unit from the master distributed test unit includes device control instructions; and further wherein the controlling means control the device in accordance with the device control instructions to maintain the test point at a value designated by the device control instructions.

9. The apparatus of claim 1 wherein the system monitor unit maintains optimum performance data for the plurality of devices which optimum performance data is customized to a user of the plurality of devices as a system.

10. The apparatus of claim 5 wherein the data base includes a predefined operating specification for selected operating parameters of the plurality of devices and the diagnostic unit includes means for continuously analyzing data received from the devices while tests are being conducted by the user on the devices and for alerting the user when an out of specification occurs.

11. The apparatus of claim 1 wherein the data base includes a history of prior device problems and resolutions of the prior device problems; and further wherein the diagnostic unit includes means for identifying from the data base a prior device problem similar to a current device problem, and for suggesting steps to the user for resolving the problem in light of the resolutions of the prior device problems.

12. The apparatus of claim 5 wherein the system monitor includes means communicating with the user interface unit for guiding the user through a procedure by which the plurality of devices are evaluated.

13. The apparatus of claim 5 wherein the system monitor includes means communicating with the user interface unit for indicating the tools needed for trouble shooting the plurality of devices.

14. The apparatus of claim 5 wherein the system monitor includes means communicating with the user interface unit for indicating servicing procedures which can be conducted on the plurality of devices.

15. The apparatus of claim 1 wherein the data base further includes substantially all documentation needed for servicing of the plurality of devices.

16. The apparatus of claim 8 wherein each of the plurality of data test unit includes means for receiving a signal from the network, and retransmitting the signal onto the network, wherein the retransmission of the signal includes remodulating the signal onto the network.

17. The apparatus of claim 1, wherein the distributed test units include a means for self-diagnostics during start-up.

18. The apparatus of claim 1, wherein the distributed test units include a means for error reporting of voltage or memory inconsistencies.

19. The apparatus of claim 1 further including a remote interface unit which communicates with the system monitor unit and permits remote users to communicate with each of the plurality of distributed test units.

20. The apparatus of claim 1 wherein the network comprises an optical network in which the plurality of distributed test units are connected in parallel to the master distributed test unit.

21. An apparatus for communicating with a plurality of devices, each device having a test point and containing one or more electrical components, the apparatus comprising:

a plurality of distributed test units each communicating with the one or more electrical components of an associated one of the plurality of devices, each test unit including means for communicating with the associated device for controlling the test point to maintain a desired value at the test point;

a network which permits communication of information among the plurality of distributed test units;

a system monitor unit communicating with the plurality of distributed test units by way of an integrated circuit board, the system monitor unit including a control unit which gathers information from the plurality of distributed test units;

a data base compiled from the information gathered from the plurality of distributed test units; and a diagnostic unit which analyzes the gathered information and identifies conditions in one or more of the plurality of devices which may require servicing.

an integrated circuit board for communication with and between the distributed test units.

22. An apparatus for communicating with a plurality of devices, each device having a test point and containing one or more electrical components, the plurality of devices collectively implement a diagnostic system, the apparatus comprising a plurality of distributed test units each capable of issuing instructions to and receiving information from an associated one of the plurality of devices, with each test unit including means for communicating with the associated device for controlling the test point to maintain a desired value at the test point;

a master distributed test unit which directs instructions to the plurality of distributed test units and receives from the plurality of distributed test units information relating to the plurality of devices;

an optical network which permits communication of information among the master distributed test unit and plurality of distributed test units;

a system monitor unit communicating with the plurality of distributed test units by way of the master distributed test unit, the system monitor unit including a control unit which gathers information from the plurality of distributed test units;

a data base compiled from the information gathered from the plurality of distributed test units; and a diagnostic unit which analyzes the gathered information and identifies conditions in one or more of the plurality of devices which may require servicing.

* * * * *